United States Patent
Schaffer

(10) Patent No.: US 10,041,151 B2
(45) Date of Patent: *Aug. 7, 2018

(54) METHOD FOR IMPARTING IMPROVED FATIGUE STRENGTH TO WIRE MADE OF SHAPE MEMORY ALLOYS, AND MEDICAL DEVICES MADE FROM SUCH WIRE

(71) Applicant: W. L. Gore & Associates, Inc., Newark, DE (US)

(72) Inventor: Jeremy E. Schaffer, Leo, IN (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/056,514

(22) Filed: Feb. 29, 2016

(65) Prior Publication Data

US 2016/0177422 A1    Jun. 23, 2016

Related U.S. Application Data

(60) Continuation of application No. 13/780,238, filed on Feb. 28, 2013, now Pat. No. 9,272,323, which is a
(Continued)

(51) Int. Cl.
  *C22C 19/03*        (2006.01)
  *A61L 31/02*        (2006.01)
  (Continued)

(52) U.S. Cl.
  CPC .......... *C22C 19/007* (2013.01); *A61L 31/022* (2013.01); *A61L 31/14* (2013.01);
  (Continued)

(58) Field of Classification Search
  None
  See application file for complete search history.

(56) References Cited

U.S. PATENT DOCUMENTS 3,802,930 A    4/1974  Brook et al.
3,948,688 A    4/1976  Clark
(Continued)

FOREIGN PATENT DOCUMENTS

JP    61-183455    8/1986
JP    10-265919    10/1998
(Continued)

OTHER PUBLICATIONS

European Office Action dated Mar. 18, 2013 from the EPO in related European Application No. 09745260.1.
(Continued)

*Primary Examiner* — George Wyszomierski
(74) *Attorney, Agent, or Firm* — Paul J Fordenbacher, Esq.

(57) ABSTRACT

Wire products, such as round and flat wire, strands, cables, and tubing, are made from a shape memory material in which inherent defects within the material are isolated from the bulk material phase of the material within one or more stabilized material phases, such that the wire product demonstrates improved fatigue resistance. In one application, a method of mechanical conditioning in accordance with the present disclosure isolates inherent defects in nickel-titanium or NiTi materials in fields of a secondary material phase that are resistant to crack initiation and/or propagation, such as a martensite phase, while the remainder of the surrounding defect-free material remains in a primary or parent material phase, such as an austenite phase, whereby the overall superelastic nature of the material is preserved.

42 Claims, 24 Drawing Sheets

Related U.S. Application Data division of application No. 12/610,297, filed on Oct. 31, 2009, now Pat. No. 8,414,714.

(60) Provisional application No. 61/228,677, filed on Jul. 27, 2009, provisional application No. 61/179,558, filed on May 19, 2009, provisional application No. 61/110,084, filed on Oct. 31, 2008.

(51) Int. Cl.
| | |
|---|---|
| *C22C 19/00* | (2006.01) |
| *C22F 1/00* | (2006.01) |
| *A61L 31/14* | (2006.01) |
| *B21F 9/00* | (2006.01) |
| *A61N 1/05* | (2006.01) |

(52) U.S. Cl.
CPC ............... *B21F 9/00* (2013.01); *C22C 19/00* (2013.01); *C22F 1/006* (2013.01); *A61L 2400/16* (2013.01); *A61N 1/05* (2013.01)

(56) References Cited

U.S. PATENT DOCUMENTS

| | | | |
|---|---|---|---|
| 3,953,253 | A | 4/1976 | Clark |
| 4,019,925 | A | 4/1977 | Nenno et al. |
| 4,881,981 | A | 11/1989 | Thomas et al. |
| 4,935,068 | A | 6/1990 | Duerig |
| 4,943,326 | A | 7/1990 | Ozawa et al. |
| 5,080,727 | A | 1/1992 | Aihara et al. |
| 5,842,312 | A * | 12/1998 | Krumme ............... B63B 21/502 248/634 |
| 5,936,066 | A | 8/1999 | Gubler et al. |
| 6,068,623 | A | 5/2000 | Zadno-Azizi et al. |
| 6,106,642 | A | 8/2000 | DiCarlo |
| 6,165,292 | A | 12/2000 | Abrams et al. |
| 6,217,567 | B1 | 4/2001 | Zadno-Azizi et al. |
| 6,254,550 | B1 | 7/2001 | McNamara et al. |
| 6,325,824 | B2 | 12/2001 | Limon |
| 6,342,067 | B1 | 1/2002 | Mathis et al. |
| 6,422,010 | B1 | 7/2002 | Julien |
| 6,428,634 | B1 | 8/2002 | Besselink et al. |
| 6,540,849 | B2 | 4/2003 | DiCarlo et al. |
| 6,565,683 | B1 | 5/2003 | Utyashev et al. |
| 6,582,461 | B1 | 6/2003 | Burmeister et al. |
| 6,773,446 | B1 | 8/2004 | Dwyer et al. |
| 6,942,688 | B2 | 9/2005 | Bartholf et al. |
| 7,005,018 | B2 | 2/2006 | Julien |
| 7,455,738 | B2 | 11/2008 | Patel et al. |
| 7,473,275 | B2 * | 1/2009 | Marquez ............... A61F 2/2409 623/2.18 |
| 7,648,599 | B2 | 1/2010 | Berendt |
| 7,789,979 | B2 | 9/2010 | Dooley et al. |
| 7,811,393 | B2 | 10/2010 | Dooley et al. |
| 8,052,620 | B2 | 11/2011 | Ishida et al. |
| 8,177,927 | B2 | 5/2012 | Dooley et al. |
| 8,216,396 | B2 | 7/2012 | Dooley et al. |
| 8,414,714 | B2 * | 4/2013 | Schaffer ............... A61L 31/022 148/402 |
| 8,709,177 | B2 | 4/2014 | Dooley et al. |
| 2003/0199920 | A1 | 10/2003 | Boylan et al. |
| 2004/0149362 | A1 | 8/2004 | Kusinski et al. |
| 2004/0216814 | A1 | 11/2004 | Dooley et al. |
| 2005/0059994 | A1 | 3/2005 | Walak et al. |
| 2005/0090844 | A1 | 4/2005 | Patel et al. |
| 2006/0086440 | A1 | 4/2006 | Boylan et al. |
| 2007/0072147 | A1 | 3/2007 | Berendt |
| 2007/0204938 | A1 | 9/2007 | Noebe et al. |
| 2007/0239259 | A1 | 10/2007 | Boylan |
| 2009/0248105 | A1 * | 10/2009 | Keilman ............... H01Q 1/22 607/32 |
| 2009/0248130 | A1 | 10/2009 | Boylan |
| 2010/0319815 | A1 | 12/2010 | Dooley et al. |
| 2010/0331946 | A1 | 12/2010 | Dooley et al. |
| 2014/0207228 | A1 | 7/2014 | Dooley et al. |

FOREIGN PATENT DOCUMENTS

| | | |
|---|---|---|
| WO | 89/10421 | 11/1989 |
| WO | 2005/045087 | 5/2005 |
| WO | 2006/081011 | 8/2006 |
| WO | 2006/104823 | 10/2006 |

OTHER PUBLICATIONS

Pelton, AR., et al., "Optimisation of processing and properties of medical grade Nitinol wire", Minimally Invasive Therapy & Allied Technologies, (2000) Vo19, No. 2, pp. 107-118.

Wada et al.; Shape recovery of NiTi shape memory alloy under various pre-strain constraint conditions, Smart Materials and Structures 0964-1726, 2005.

Wu, Ming; Effects of phase transformations on fatigue endurance of a superelastic NiTi cloy, Journal of ASTM International, vol. 4, No. 3, 2007.

Sawaguchi, T.; Crack initiation and propagation in 50.9 At. pct Ni—Ti pseudoelastic shape-memory wires in bending-rotation fatigue, Mettalurgical and Materials Transactions A, vol. 34A, Dec. 2003.

Olbricht et al.; The influence of temperature on the evaluation of functional properties during psuedoelastic cycling of ultra fine grained NiTi, , Materials Science and Engineering 142-145, 2008.

Grossmann et al.; Processing and property assessment of NiTi and NiTiCu shape memory actuator springs, Jan. 1, 2008 Wiley-VCH Verlag GmbH & Co.

Duerig; Some unsolved aspects of Nitinol, Materials Science & Engineering A 438-440 (2006), pp. 69-74.

McKelvey et al.; Fatigue-Crack Growth Behavior in the Superelastic and Shape-Memory Alloy Nitinol, Metallurgical and Materials Transactions A, vol. 32A, Mar. 2001, pp. 731-743.

Robertson et al.; In vitro fatigue-crack growth and fracture toughness behavior of thin-walled superelastic Nitinol tube for endovascular stents: a basis for defining the effect of crack-like defects, Miomaterials 28 (2007), pp. 700-709.

Schaffer; Structure-Property Relationship in Conventional and Nanocrystalline NiTi Intermetallic Alloy Wire, Journal of Materials Engineering and Performance, vol. 18 (5-6) Aug. 2009, pp. 582-587.

Karaman et al.; Transformation behavior and unusual twinning in a NiTl shape memory alloy ausformed using equal channel angular extrusion, Philosophical Magazine, vol. 85, No. 16 Jun. 1, 2005, pp. 1729-1745.

Sun et al.; Phase transformation in superelastic NiTl polycrystalline micro-tubes under tension and torsion—from localization to homogeneous deformation, International Journal of Solids and Structures 39 (2002), pp. 3797-3809.

Paula et al., Thermomechanical behavior of Ti-rich NiTl shape memory alloys, Materials Science and Engineering A 481-482 (2008), pp. 146-150.

Prokoshkin et al.; Alloy composition, deformation temperature, pressure and post-deformation annealing effects in severely deformed Ti—Ni based shape memory alloys, Acta Materialia 53 (2005), pp. 2703-2714.

Waitz et al.; Martensitic phase transformations in nanocrystalline NiTl studied by TEM, Acta Materialia 52 (2004), pp. 137-147.

Waitz et al.; Martensitic transformation of NiTi nanocrystals embedded in an amorphous matrix, Acta Materialia 52 (2004), pp. 5461-5469.

Siegert et al.; First cycle shape memory effect in the ternary NiTiNb system, Journal of Physics IV, France; 112, 2003, pp. 739-742.

LaGrange et al.; An ion implantation processing technique used to develop shape memory TiNi thin film micro-actuator devices, Journal of Physics IV France; 115, 2004, pp. 47-56.

Montero-Ocampo et al.; Effect of compressive straining on corrosion resistance of a shape memory Ni—Ti alloy in ringer's solution, Journal of Biomedical Materials Reseach, vol. 32 (1996), pp. 583-591.

(56) References Cited

OTHER PUBLICATIONS

Cook et al.; Fundamental aspects of the cold working of metals, Journal of the Institute of Metals, vol. 78, pp. 463-482, Abstract only, Jan. 1951.
Benum et al.; Substructure characteristics of grain boundary regions and nucleation of recrystallisation at grain boundaries in high purity aluminium Texture and anisotrophy of polycrystals, ITAP: International Conference on Texture and Anisotrophy of polycrystals (Ciausthal DEU), vol. 273-275, pp. 327-332, Sep. 22, 1997, Materials science forum, Abstract only.
International Preliminary Report on Patentability dated Feb. 10, 2011 from the International Preliminary Examining Authority in related International Application No. PCT/US2009/062901.
Written Opinion and Internal Search Report dated Jan. 4, 2010 in related International Application No. PCT/ US2009/062901.

\* cited by examiner

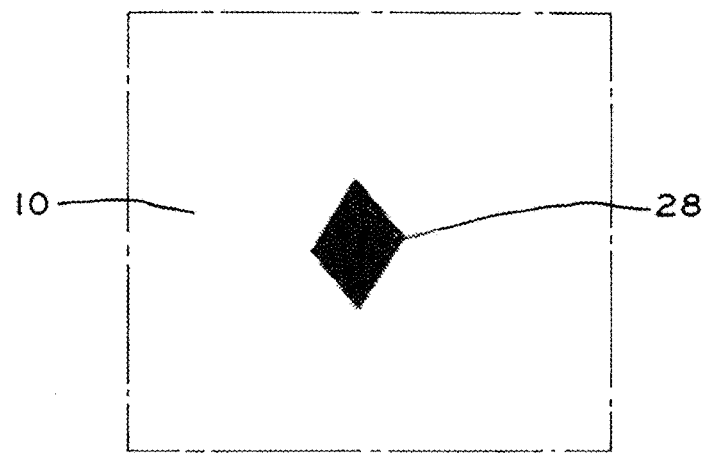
FIG_7(b)
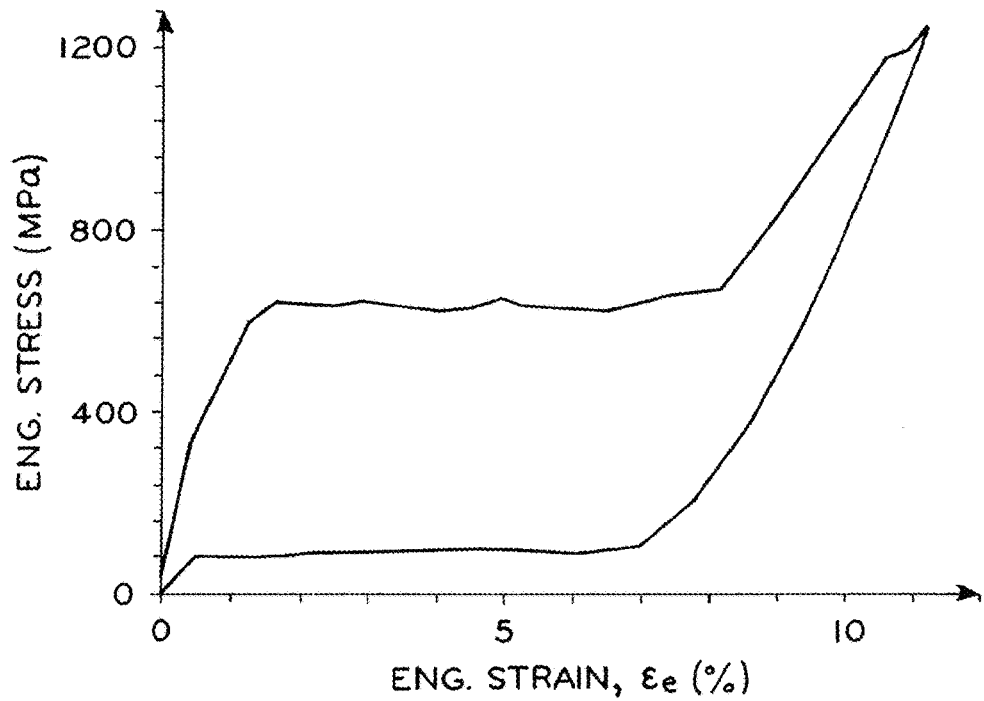
FIG_8

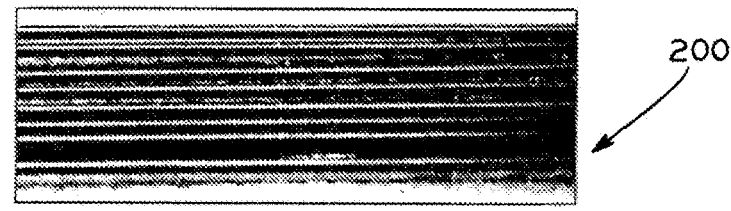
FIG_12(d)
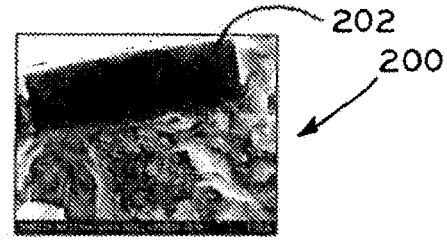
FIG_12(e)
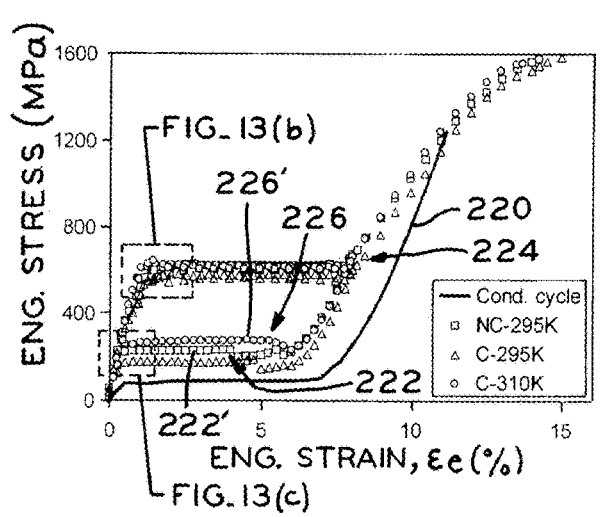
FIG_13(a)
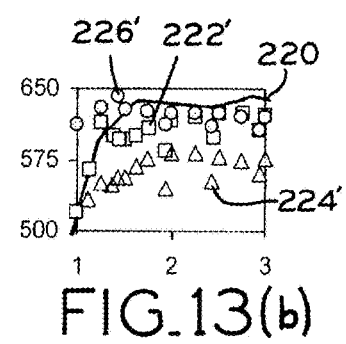
FIG_13(b)
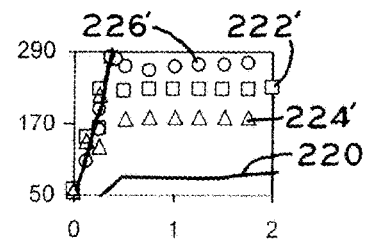
FIG_13(c)

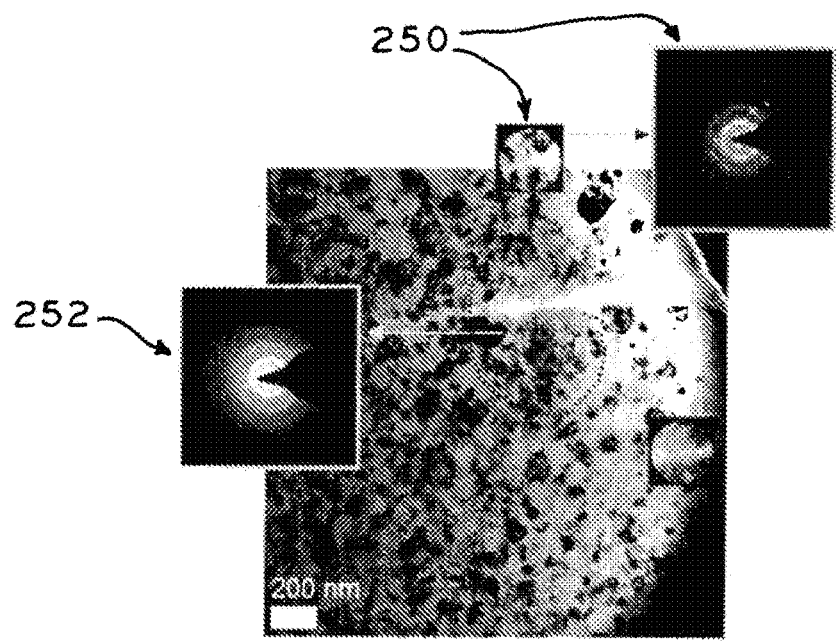
FIG_16
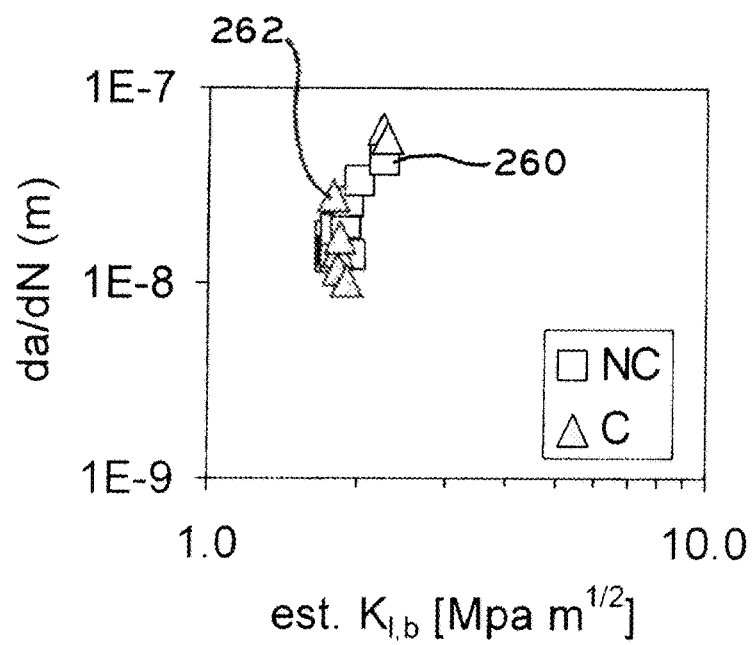
FIG_17

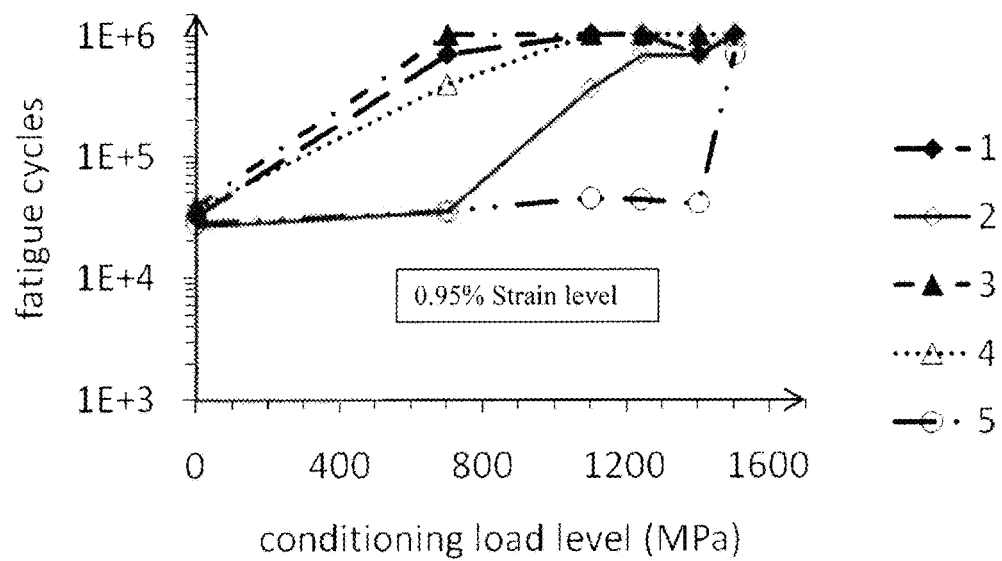
FIG_18(c)
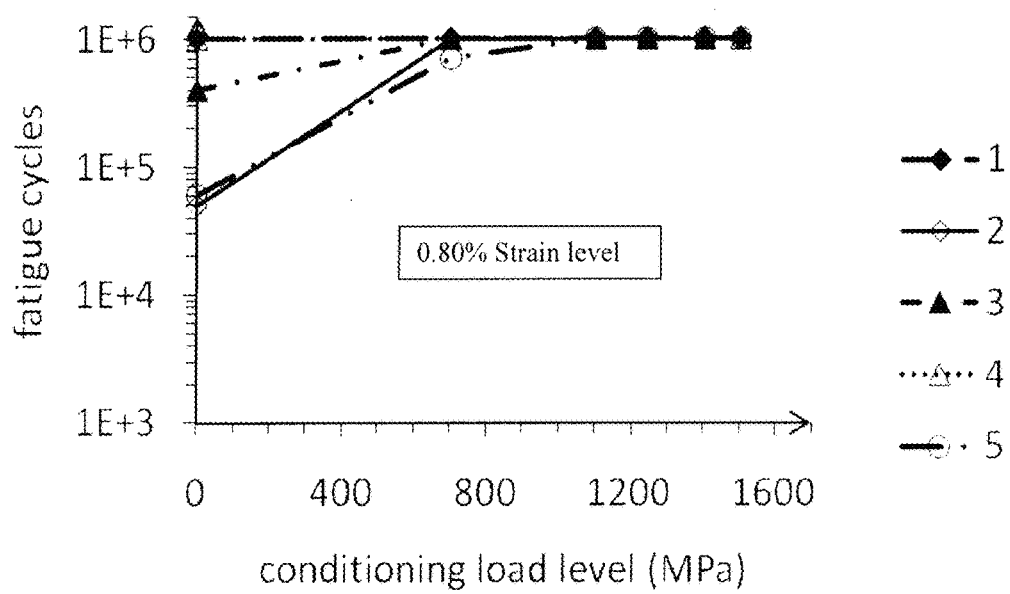
FIG_18(d)

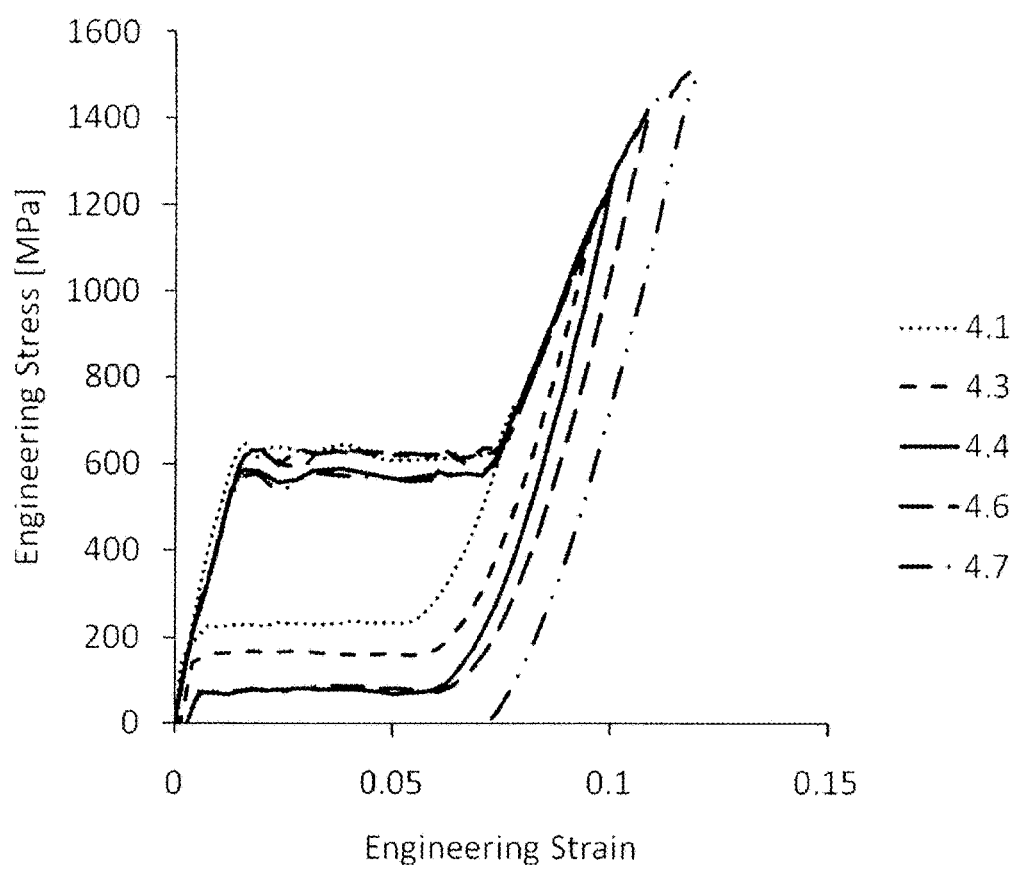
FIG_19(d)

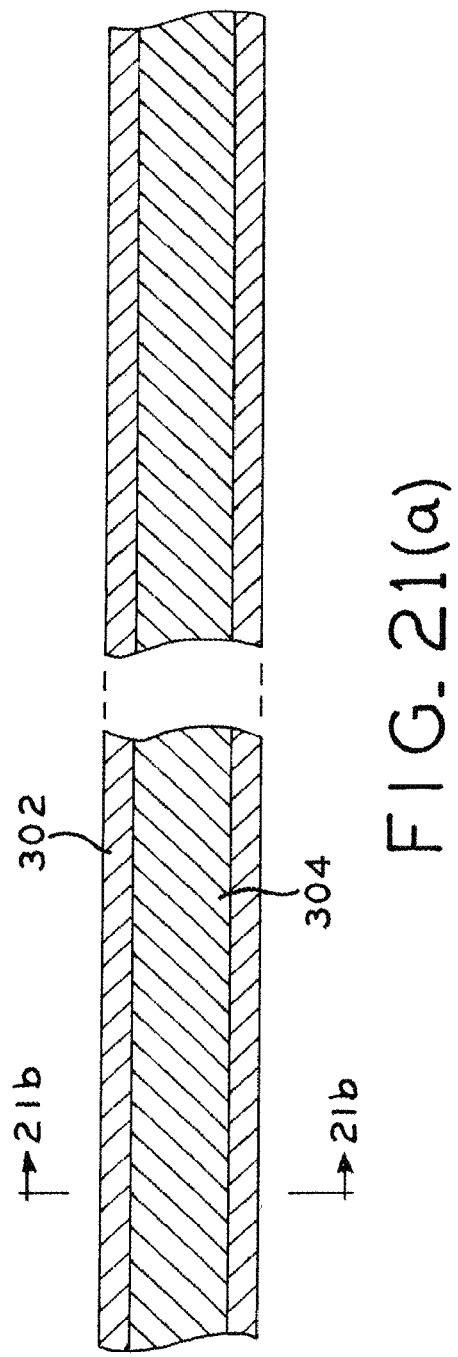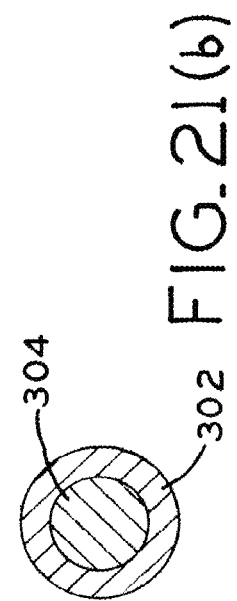

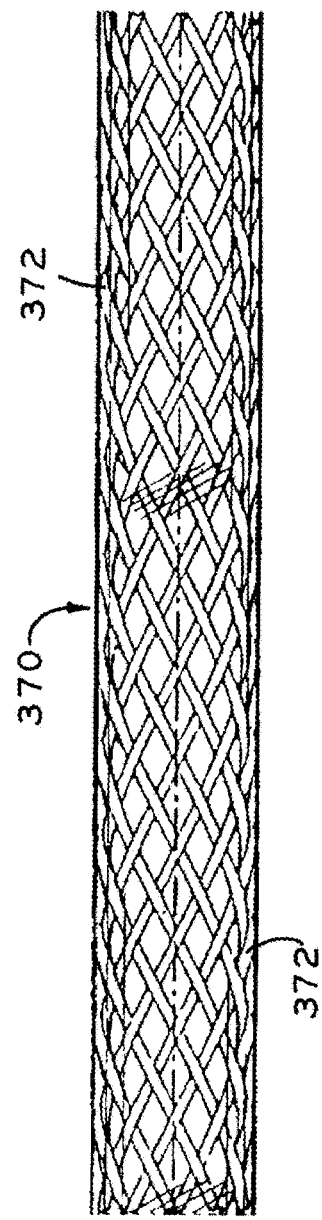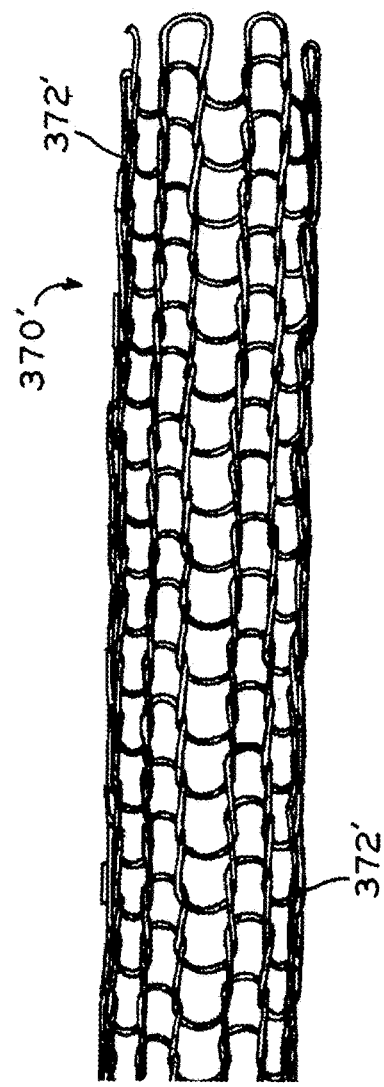
FIG. 22(a)
FIG. 22(b)

METHOD FOR IMPARTING IMPROVED FATIGUE STRENGTH TO WIRE MADE OF SHAPE MEMORY ALLOYS, AND MEDICAL DEVICES MADE FROM SUCH WIRE

CROSS REFERENCE TO RELATED APPLICATIONS

This application is a continuation application of U.S. patent application Ser. No. 13/780,238 filed on Feb. 28, 2013, now U.S. Pat. No. 9,272,323, which is a divisional application of U.S. patent application Ser. No. 12/610,297 filed on Oct. 31, 2009, now U.S. Pat. No. 8,414,714 which issued on Apr. 9, 2013 which claims priority to U.S. Provisional Patent Application Ser. No. 61/110,084, entitled NANOGRAIN DAMAGE RESISTANT WIRE, filed on Oct. 31, 2008, U.S. Provisional Patent Application Ser. No. 61/179,558, entitled NANOGRAIN DAMAGE RESISTANT WIRE, filed on May 19, 2009, and U.S. Provisional Patent Application Ser. No. 61/228,677, entitled NANOGRAIN DAMAGE RESISTANT WIRE, filed on Jul. 27, 2009, the entire disclosures of which are expressly incorporated herein by reference.

BACKGROUND

1. Technical Field

The present disclosure relates to fatigue damage resistant wire and, in particular, relates to a method of manufacturing wire made of a shape memory alloy, which demonstrates improved fatigue strength properties, as well as medical devices made with such wire.

2. Description of the Related Art

Shape memory materials are materials that "remember" their original shape, and which, after being deformed, return to that shape either spontaneously or by applying heat to raise their temperature above a processing and material related threshold known as the transformation temperature. Heating to recover shape is commonly referred to in the art as "shape memory", whereas spontaneous recovery is commonly referred to as pseudoelasticity. Pseudoelasticity, sometimes called superelasticity, is a reversible response to an applied stress, caused by a phase transformation between the austenite or parent phase and the martensite or daughter phase of a crystal. It is exhibited in shape memory alloys. Pseudoelasticity and shape memory both arise from the reversible motion of domain boundaries during the phase transformation, rather than just bond stretching or the introduction of defects in the crystal lattice. A pseudoelastic material may return to its previous shape after the removal of even relatively high applied strains by heating. For example, even if the secondary or daughter domain boundaries do become pinned, for example due to dislocations associated with plasticity, they may be reverted to the primary or parent phase by stresses generated through heating. Examples of shape memory materials include iron-chrome-nickel, iron-manganese, iron-palladium, iron-platinum, iron-nickel-cobalt-titanium, iron-nickel-cobalt-tantalum-aluminum-boron, copper-zinc-aluminum, copper-zinc-aluminum-nickel, copper-aluminum-nickel, and nickel titanium alloys. Shape memory materials can also be alloyed with other materials including zinc, copper, gold, and Iron.

Shape memory materials are presently used in a variety of applications. For example, a variety of military, medical, safety and robotic applications for shape memory materials are known. Medical grade shape memory materials are used for orthodontic wires, guide wires to guide catheters through blood vessels, surgical anchoring devices and stent applications, for example. One shape memory material in wide use, particularly in medical device applications, is a nickel-titanium shape memory material known as "Nitinol".

Many medical grade shape memory wire products are made of biocompatible implant grade materials including "NiTi" materials. As used herein, "nickel-titanium material", "nickel-titanium shape memory material" and "NiTi" refer to the family of nickel-titanium shape memory materials including Nitinol (an approximately equiatomic nickel-titanium, binary shape memory material) as well as alloys including nickel and titanium as primary constituents but which also include one or more additional elements as secondary constituents, such as Nitinol tertiary or quaternary alloys (Nitinol with additive metals such as chromium, tantalum, palladium, platinum, iron, cobalt, tungsten, iridium and gold).

Significant research has been dedicated to understanding how NiTi behaves in the body from the viewpoint of biological host response, but much less has been published that quantitatively correlates structure with mechanical properties.

More particularly, the fatigue properties of NiTi material have been the subject of recent research. The fatigue crack propagation behavior of Nitinol was studied in detail by McKelvey and Ritchie, as published in Fatigue-Crack Growth Behavior in the Superelastic and Shape-Memory Alloy Nitinol, *Metallurgical and Materials Transactions*, 32A, 2001, pgs. 731-743. McKelvey et al. observed that the crack growth propagation rate and $\Delta 1K_{th}$, which denotes the stress-intensity fatigue threshold in a given fatigue-crack growth scenario, were different for equivalent composition at martensite-stable and austenite-stable temperatures where the crack growth rate was generally lower at martensite-stable temperatures. They also observed that, under plane strain conditions, the heavily slipped material near the crack tip at superelastic regime temperatures remained austenitic, presumably inhibited from undergoing volume contractile, stress-induced phase transformation by the triaxial stress state, while plane stress conditions generally resulted in stress-induced martensite near the crack tip.

Wire products made of shape memory materials are manufactured by forming a relatively thick piece of hot-worked rod stock from a melt process. The rod stock is then further processed into wires by drawing the rod stock down to a thin diameter wire. During a drawing process, often referred to as a "cold working" process, a wire is pulled through a lubricated die to reduce its diameter. The deformation associated with wire drawing increases the stress in the material, and the stress eventually must be relieved by various methods of heat treatment or annealing at elevated temperatures to restore ductility, thus enabling the material to be further cold worked to a smaller diameter. Conventional wire annealing typically results in grain growth with a concomitant random crystal orientation, and the various material or fiber "textures" that are generated during cold wire drawing are mostly eliminated during conventional annealing and recrystallization. These iterative processes of cold working and annealing may be repeated several times before a wire of a desired diameter is produced and processing is completed.

Wire materials manufactured by the above processes typically contain microstructural defects, such as pores, inclusions, interstitials, and dislocations. An inclusion comprises a phase which possesses distinct properties from the primary material matrix and is divided from the matrix by a phase boundary. Inclusions may result from oxide or other metallic or non-metallic precipitate formation during primary melting or other high temperature treatment and may include carbides, nitrides, silicides, oxides or other types of particles. Inclusions may also arise from contamination of the primary melt materials or from the mold which contains the molten ingot. In the case of an interstitial, an atom occupies a site in the crystal structure at which there usually is not an atom. The atom may be a part of its host material, such as a base metal or alloying metal, or it may be an impurity. A dislocation is a linear defect around which some of the atoms of the crystal lattice are misaligned and appear as either edge dislocations or screw dislocations. Edge dislocations are caused by the termination of a plane of atoms in the middle of a crystal, while a screw dislocation comprises an internal structure in which a helical path is traced around the linear defect or dislocation line by the atomic planes of atoms in the crystal lattice. Mixed dislocations, combining aspects of screw and edge dislocations, may also occur.

Internal or external defects, such as inclusions, pores, or defects induced during wire processing may weaken the host material at the site of the defect, potentially resulting in failure of a material at the site of that defect. This weakening may be particularly acute where the defect is relatively large and/or of significantly disparate stiffness compared with adjacent dimensions of the material (such as for fine or small diameter wire). Failure of shape memory wires is more likely to occur at the site of the defect. Since inherent defects cannot be completely eliminated from the wire material, management of inherent defects and mitigation of their negative impact on wire properties is desirable.

One previously proposed solution to the problem of inherent defects has been to treat selected regions of a wire that are expected to be subjected to high strain by converting the bulk material in such regions to a different phase than the remainder of the bulk material of the wire. For example, under predetermined operating conditions, such as a predetermined operation temperature, the high strain wire regions are stabilized in a martensite phase while the lesser strain regions remain in an austenite phase. This method is therefore directed to treating predetermined regions of a wire to convert the bulk material in the regions to a more stable phase regardless of the presence, number, and location of any defects in the bulk material.

However, it may not always be possible or practical to predict what regions of a continuous wire will be subjected to high strains when portions of the wire are later incorporated into a medical device. It may also be desirable to leave defect-free portions of wire unaffected by mitigation efforts and, therefore, available to meet other design considerations. For example, a disadvantage of the above process is that for wire made of shape memory material, the regions that are stabilized in the martensite phase will lose the superelastic characteristic.

Although wires made in accordance with foregoing processes may demonstrate excellent fatigue strength, further improvements in fatigue strength are desired, particularly with reference to fatigue damage that propagates from defects.

What is needed is a method of manufacturing a wire that demonstrates improved fatigue strength, and medical devices that include such wire.

SUMMARY

The present disclosure relates to wire products, and medical devices including wire products, such as round and flat wire, strands, cables, coils, and tubing, made from a shape memory material or alloy. Defects within the material are isolated from a primary, or parent, material phase within one or more areas of stabilized secondary, or daughter, material phases that are resistant to failure, such that the wire product demonstrates improved fatigue strength. In one application, a method of mechanical conditioning in accordance with the present disclosure isolates defects in nickel-titanium or NiTi shape memory materials in localized areas or fields of a secondary material phase that are resistant to crack initiation and/or propagation, such as a martensite phase, while the remainder of the surrounding defect-free material remains in a primary material phase, such as an austenite phase, whereby the overall superelastic and/or nature of the material is preserved.

Wire products manufactured in accordance with the present disclosure maintain good mechanical properties in addition to improved fatigue performance. Increases in the strain fatigue limit for both high cycle and low cycle fatigue are observed, while shape memory or superelastic characteristics are preserved.

As discussed below and shown in the Working Examples, the amount of secondary phase material formed about the defects during the mechanical conditioning process is sufficient to either completely isolate the defects or at least partially isolate high stress concentrator areas about the defects in order to the improve fatigue strength of the material and yet, when the bulk of the material reverts back to the primary phase after the mechanical conditioning, the overall amount of remaining secondary phase material that is formed about the defects is not sufficient compromise the shape memory or superelastic characteristic of the material as a whole. In this respect, the amount of mechanical conditioning may be specifically tailored to achieve a desired balance between fatigue strength and material elasticity.

In one form thereof, the present invention provides a medical device including a wire made of a nickel-titanium shape memory material, the wire having a fatigue endurance exceeding 0.95% strain amplitude at greater than $10^6$ cycles.

In other embodiments, the medical device may include a wire having a fatigue endurance exceeding 1.1% strain amplitude at greater than $10^6$ cycles, or a fatigue endurance exceeding 1.1% strain amplitude at greater than $10^9$ cycles. In a further embodiment, the medical device may include a wire having a residual strain of less than 0.25% after being subjected to engineering strain of at least 9.5%.

In another form thereof, the present invention provides a medical device including a wire product made of a shape memory material, the shape memory material having a plurality of defects, the wire product substantially comprised of the shape memory material in a primary phase and including portions of the shape memory material comprising a secondary phase at localized regions disposed proximate respective defects, with at least some of the secondary phase portions separated by the primary phase.

The shape memory material may be a nickel-titanium shape memory material, in which the primary phase is an austenite phase, and the secondary phase portions comprise a martensite phase. The secondary phase portions may together comprise less than 15% of the shape memory material, by volume.

In a further embodiment, the shape memory material may be a nickel-titanium shape memory material, with the wire product having a fatigue endurance exceeding 0.95% strain amplitude at greater than $10^6$ cycles, a fatigue endurance exceeding 1.1% strain amplitude at greater than $10^6$ cycles, or a fatigue endurance exceeding 1.1% strain amplitude at greater than $10^9$ cycles. The wire may also have a residual strain of less than 0.25% after being subjected to engineering strain of at least 9.5%. The wire product may be selected from the group consisting of wire having a circular cross-section, wire having a non-circular cross-section, cable, coil, and tubing.

In a further form thereof, the present invention provides a method, including the steps of: providing a wire product made of a shape-set, shape memory material; mechanically conditioning the wire product by: applying an engineering stress between 700 MPa and 1600 MPa; and releasing the applied engineering stress; and incorporating the wire product into a medical device. The mechanical conditioning step may occur either prior to or after the incorporation step.

In another embodiment, the mechanical conditioning step includes: applying an engineering stress between 900 MPa and 1450 MPa; and releasing the applied engineering stress. In a further embodiment, the mechanical conditioning step includes: applying an engineering stress between 1100 MPa and 1350 MPa; and releasing the applied engineering stress. The method may further include the repeating the mechanically conditioning step at least once.

In one embodiment, the shape memory material may be a nickel-titanium shape memory material, and the mechanical conditioning step may be conducted below a martensite deformation temperature ($M_d$) of the nickel-titanium shape memory material. The mechanical conditioning step may further include: applying the first force to the wire product in an environment having a temperature T, wherein $$T = A_f \pm 50° C.,$$

wherein $A_f$ is the austenite transformation finish temperature of the nickel-titanium shape memory material. The wire product may be selected from the group consisting of wire having a circular cross-section, wire having a non-circular cross-section, cable, coil, and tubing.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 7(b) is an fragmentary view of a defect in the wire of FIG. 7(a);

FIG. 8 is a stress-strain curve for a mechanical conditioning process in accordance with the present disclosure;

FIG. 12(d) is an optical photograph of 150 μm diameter NiTi wires with cue marks evident near centerline;

FIG. 12(e) is a transverse SEM micrograph of a failed fatigue fracture specimen showing the FIB-milled sharp defect (FSD) depth corresponding to FIG. 12(b);

FIG. 13(a) shows graphical representations of cyclic tensile data for samples including overload conditioning cycle, non-conditioned, and conditioned samples, with varying test temperatures;

FIG. 13(b) is an enlarged insets showing a loading region of the graph shown in FIG. 13(a);

FIG. 13(c) is an enlarged insets showing an unloading region of the graph shown in FIG. 13(a);

FIG. 16 is a bright field TEM (BF-TEM) image of an FSD crack root after mechanical conditioning, with the insets showing selected area electron diffraction patterns (SADP) for regions within (left) and outside of (right) the structurally distinct zone demarcated by a dashed line and extending approximately 0.5 μm from the crack tip;

FIG. 17 is a graphical representation of crack growth rate data inferred from high resolution scanning electron microscopy of ductile striation spacing observations and estimated stress intensity at probable crack front location based on a semi-elliptical crack in an infinite rod;

FIG. 18(c) is a graph showing cycles to failure for the five sets of wire samples shown in FIG. 18(a), where a sample from each set of wires has been mechanically conditioned with a given level of engineering stress, and where the wires were tested at a 0.95% strain level;

FIG. 18(d) is a graph showing cycles to failure for the five sets of wire samples shown in FIG. 18(a), where a sample from each set of wires has been mechanically conditioned with a given level of engineering stress, and where the wires were tested at a 0.80% strain level;

FIG. 19(d) is a stress-strain curve for five wire samples, where each wire sample was loaded using the conditioning regime indicated by the legend at the right of the figure and described in Table 2;

FIG. 21(a) is a section view of Drawn Filled Tubing (DFT®) wire manufactured in accordance with an embodiment of the present disclosure (DFT® is a registered trademark of Fort Wayne Metals Research Products Corporation of Fort Wayne, Ind.);

FIG. 21(b) is a cross sectional view taken along line 18B-18B of FIG. 18(a);

FIG. 22(a) is an elevation view of a braided tissue scaffold or stent including a wire made in accordance with the present process; and FIG. 22(b) is an elevation view of a knitted tissue scaffold or stent including a wire made in accordance with the present process.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 1:
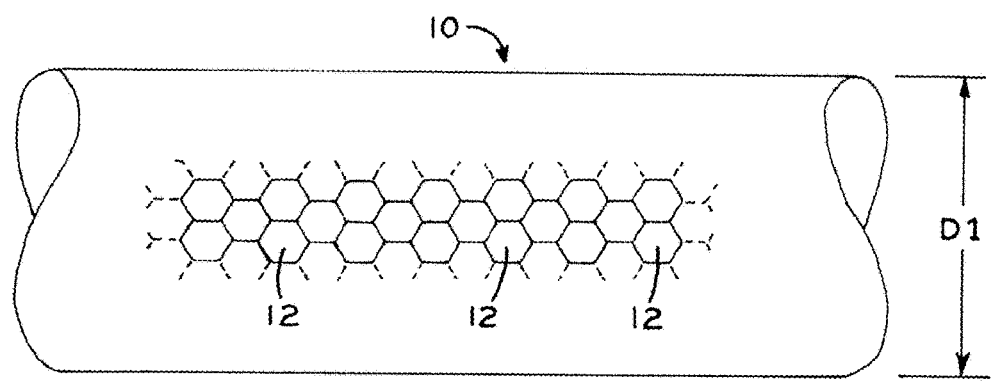
FIG. 1 is a schematic view of a portion of wire having an equiaxed grain structure.

The present disclosure relates to wire products, and medical devices including wire products, such as round and flat wire, strands, cables, coils, and tubing, made from a shape memory material or alloy. Defects within the material are isolated from a primary, or parent, material phase within one or more stabilized secondary, or daughter, material phases that are resistant to failure, such that the wire product demonstrates improved fatigue strength. In one application, a method of mechanical conditioning in accordance with the present disclosure isolates defects in nickel-titanium or NiTi shape memory materials in localized areas or fields of a secondary material phase that are resistant to crack initiation and/or propagation, such as a martensite phase, while the remainder of the surrounding defect-free material remains in a primary material phase, such as an austenite phase, whereby the overall superelastic nature of the material is preserved.

As used herein, a "defect" refers to material defects such as crack-like defects, inclusions, dislocations, and other non-uniformities, as well as any other internal or external defects or stress risers present in a material, as well as melt intrinsic and extrinsic defects such as inclusions, porosity, voids and oxide precipitate formation after melting.

Exemplary manufacturing processes by which wires may be made in accordance with the present disclosure are set forth in Section I below, and general descriptions of the resulting physical characteristics of wires made in accordance with the present process are set forth in Section II below. Working Examples are set forth in Section III below. Applications using wires made in accordance with the present disclosure are set forth in Section IV below.

Several suitable shape memory materials may be used for forming wire products according to the present disclosure. As used herein, "shape memory material" encompasses medical grade shape memory materials including nickel-titanium or NiTi (defined above), as well as medical grade shape memory alloys including beta titanium alloys (such as Beta C that comprise primarily the beta phase at room temperature), and any other medical grade shape memory alloys exhibiting similar superelastic and/or shape memory characteristics such as tantalum-titanium, titanium-niobium, and iron-nickel-cobalt alloys. Additionally, as used herein, "shape memory material" also encompasses non-medical grade shape memory alloys such as iron-chrome-nickel, iron-manganese, iron-palladium, iron-platinum, iron-nickel-cobalt-titanium, iron-nickel-cobalt-tantalum-aluminum-boron, copper-zinc-aluminum, copper-zinc-aluminum-nickel, copper-aluminum-nickel, and nickel-titanium alloys.

Moreover, it is contemplated that various shape-memory materials having either a one-way memory effect or a two-way memory effect, and other related materials, may be subjected to the present mechanical conditioning process to achieve enhanced physical characteristics identified in the discussion below and in the corresponding Working Examples.

As discussed in detail in Section IV below, fatigue damage resistant shape memory wire made in accordance with the present disclosure may be used in medical devices such as, for example, implantable cardiac pacing, shocking and/or sensing leads, implantable neurological stimulating and/or sensing leads, wire-based stents, blood filter devices, or any other medical device application in which high fatigue strength and/or a shape memory or superelastic characteristic is desired. Wire products produced in accordance with the present disclosure may also be used in non-medical device applications in which high fatigue strength and/or a shape memory or superelastic characteristic is desired.

As used herein, "wire" or "wire product" encompasses continuous wire and wire products, such as wire having a round cross section and wire having a non-round cross section, including flat wire, as well as other wire-based products such as strands, cables, coil, and tubing.

I. DESCRIPTION OF THE PRESENT MANUFACTURING PROCESS

1. Wire Preparation

Prior to the mechanical conditioning process of the present disclosure, discussed below, wire made of a shape memory material is subjected to cold work prior to undergoing a shape set annealing process. The shape setting step imparts the primary shape memory and/or superelastic characteristics of the material prior to mechanical conditioning.

Initial preparation of a wire may involve first forming a piece of rod stock, for example, based on conventional melt processing techniques, followed by one or more iterations of conventional cold working and annealing. Referring to FIG. 1, a schematic or exaggerated view of a portion of wire 10 manufactured in accordance with conventional cold working and annealing techniques is shown. Wire 10 has been subjected to one or more, perhaps several or a very large number of, iterations of conventional cold working and annealing, as described above, to form an equiaxed crystal structure within the material of wire 10. Representative equiaxed crystals are depicted in wire 10 at 12. As used herein, "equiaxed" refers to a crystal structure in which the individual crystals 12 have axes that are approximately the same length, such that the crystals 12 collectively have a large number of slip planes, leading to high strength and ductility. However, it is not necessary that the grain structure be equiaxed. The grain structure may, for example, contain deformed grains that have been recovered to the B2 cubic austenite phase through the high temperature shape setting process described below.

Figure 2:
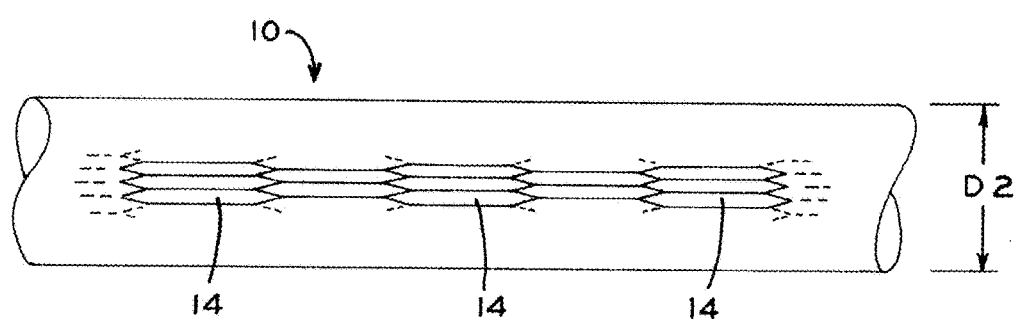
FIG. 2 is a schematic view of the portion of wire of FIG. 1 having an elongated grain structure after cold work conditioning.

Referring now to FIG. 2, prior to the shape-set anneal, wire 10 may optionally subjected to further cold work in the form of a cold work conditioning step if a nanograin microstructure is desired. As used herein, "cold work conditioning" means imparting a relatively large amount of cold work to a material, such as by wire drawing, swaging, or otherwise forming.

Figure 4:
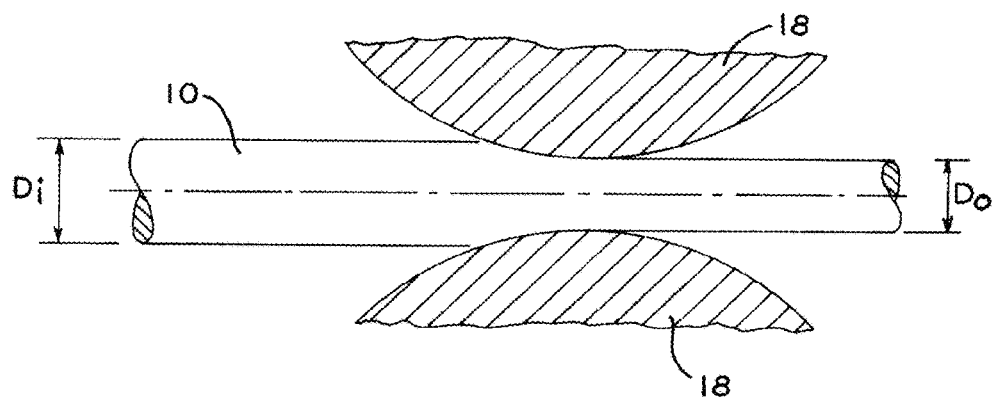
FIG. 4 is a schematic view illustrating an exemplary drawing process using a lubricated die.

Referring to FIG. 4, the cold work conditioning step is performed by drawing wire 10 through a lubricated die 18 (FIG. 4) having a an output diameter $D_2$, which is less than diameter $D_1$ of the undrawn wire 10 shown in FIG. 2. In one exemplary embodiment, the cold work conditioning step by which the diameter of wire 10 is reduced from $D_1$ to $D_2$ is performed in a single draw and, in another embodiment, the cold work conditioning step by which the diameter of wire 10 is reduced from $D_1$ to $D_2$ is performed in multiple draws which are performed sequentially without any annealing step therebetween.

Further discussion of exemplary cold work conditioning processes are presented in U.S. patent application Ser. No. 12/563,062, entitled FATIGUE DAMAGE RESISTANT WIRE AND METHOD OF PRODUCTION THEREOF, filed Sep. 18, 2009, assigned to the present assignee, the disclosure of which is hereby expressly incorporated by reference herein in its entirety. The foregoing reference also discloses methods of limited annealing following the cold work conditioning to create a nanograin microstructure, which may optionally be applied to wires prior to subjecting same to the mechanical conditioning process in accordance with the present disclosure, discussed below.

Figure 3:
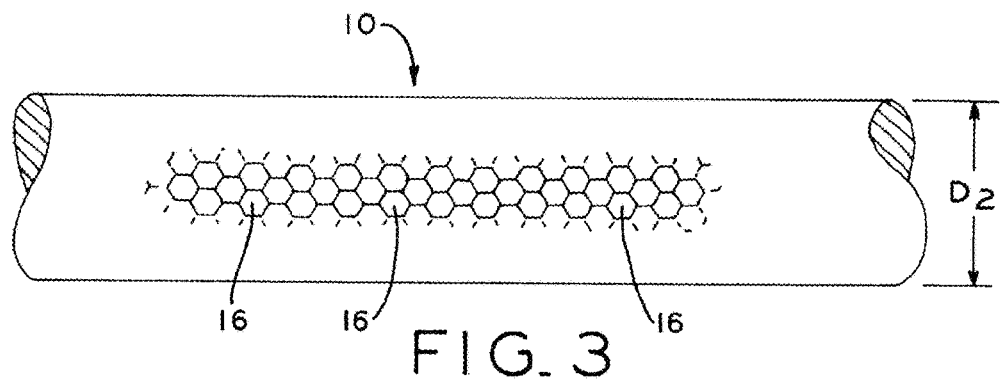
FIG. 3 is a schematic view of the portion of wire of FIG. 2 having an equiaxed grain structure with smaller grains than the equiaxed grain structure of the wire in FIG. 1 after a shape set annealing process.
Figure 5:
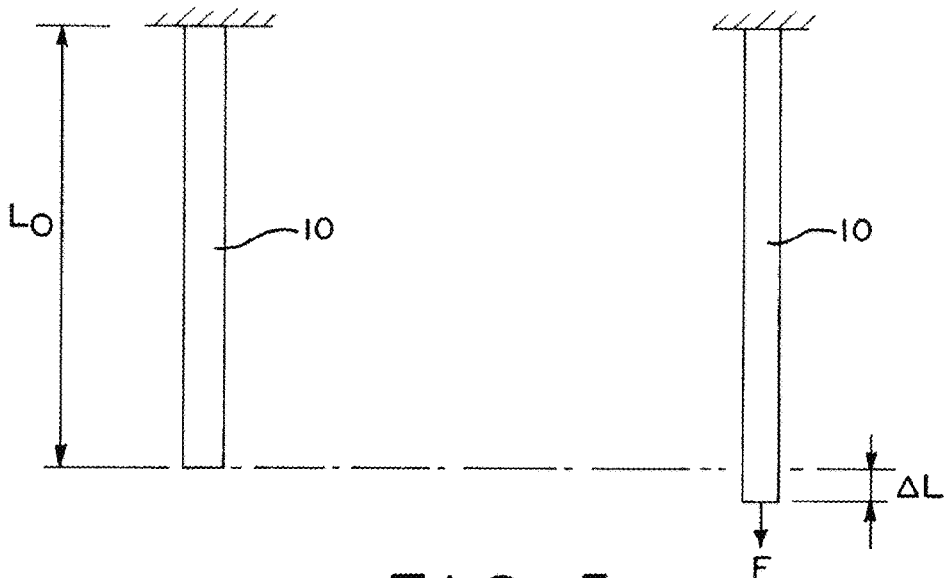
FIG. 5 is a depiction of the processing step of conditioning a wire using a mechanical conditioning method in accordance with the present disclosure.

Regardless of the amount of cold work imparted to the wire and/or whether cold work conditioning is used, once drawn to the desired size, and as shown in FIG. 5, wire 10 undergoes a shape setting annealing process in which it is continuously annealed under constant tension sufficient to hold the wire in a substantially linear configuration during the shape set annealing process. Shape set annealing typically occurs at a temperature between 300° C. (673 K) and 600° C. (1073 K), where the temperature is sufficiently high to restore a majority of the wire material to the primary or austenite phase. The shape setting annealing process may result in the formation of a new crystallographic structure, which may comprise nano-scale equiaxed crystals 16 in wire 10, as shown in FIG. 3. However, as noted above, an equiaxed or nanograin crystal microstructure is not required for the mechanical conditioning process described below.

2. Mechanical Conditioning

In accordance with the present disclosure, wire made of a shape memory material may be subjected to a mechanical conditioning process to improve its resistance to fatigue damage. In the present embodiment, mechanical conditioning is performed by application of a force to the wire in an environment having a temperature range within approximately 50° C. of the austenite transformation finish temperature ($A_f$), i.e., $T = A_f \pm 50°$ C.

Figure 6:
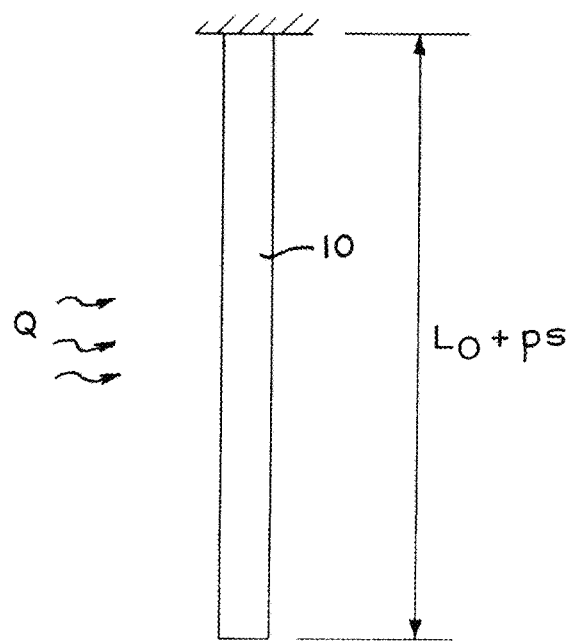
FIG. 6 is a depiction of the processing step of releasing the tension in the wire of FIG. 6.

Referring now to FIGS. 5 and 6, in the mechanical conditioning process, shape memory wire, shown in FIG. 5, in the heat set annealed condition is secured at a first end. Controlled engineering strain is applied in the direction of arrow F to a finished engineering strain, $\varepsilon_C$, of 0.08 to 0.14 units, wherein:

$$\varepsilon_c = \frac{\Delta L}{L_0},$$

with $L_o$ being the initial length, and $\Delta L$ being the length increase imparted by strain.

The range for $\varepsilon_C$ may be from as little as 0.06, 0.08, or 0.10 units to as much as 0.13, 0.14 0.16 units, or within any range encompassed by the foregoing values, to provide the increased benefits to the shape memory wire discussed herein. It is thought that if the end point is lower than 0.08, the mechanical conditioning may not impart the desired physical properties to the wire, as any dislocation or stress-induced secondary phase, such as martensite that is formed, may revert back to the primary or parent phase, such as austenite. In contrast, if the end point is in excess of 0.14, the wire may potentially be strained by the mechanical conditioning beyond its elastic deformation range to the extent that an undesirably large amount of plastic deformation may result.

An alternative characterization of the mechanical conditioning process of the present disclosure may be expressed as the application of engineering stress to the material. For an application of force in a tensile test as described herein, engineering stress is calculated using the following equation:

$$\sigma_e = \frac{P}{A_0}$$

where $\sigma_e$ is the engineering stress, P is the force applied, and $A_0$ is the cross-sectional area of the material before application of force. In engineering stress terms, the range for Ge may be from as little as 700 MPa, 900 MPa or 1100 MPa to as much as 1350 MPa, 1450 MPa or 1600 MPa, or within any range encompassed by the foregoing values, to provide the increased benefits to the shape memory wire discussed herein.

However, it is contemplated that force may be applied to the wire or wire product using alternate stress loading regimes, such as via methods other than a tensile test, that may be more appropriate to the geometry of a particular wire product.

The temperature should be maintained below the martensitic deformation temperature, $M_d$, during the application of force to the wire in the mechanical conditioning process. If the temperature exceeds the martensitic deformation temperature, the bulk of the shape memory wire material will not transform to martensite upon loading, because any plastic deformation will occur in the austenite phase, and therefore the localized phase transformation mechanism would not occur. The entirety of the wire material will remain in a plastically deformed austenite state, with the austenite or primary phase containing significant plasticity and little retained martensite phase.

Referring to FIG. 6, once the desired stress or strain is applied to the wire, the force is removed and the sample is allowed to freely recover and, if the temperature is below the austenitic finish temperature, or if further recovery of the bulk material is required, heat Q is applied to drive the temperature, T to sufficiently greater than the austenitic finish temperature (i.e., $T>A_f$) for recovery of the bulk material, leaving the material in a state wherein defects are still isolated by a dislocation stabilized secondary phase as discussed below.

The steps of applying a controlled engineering stress or strain and subsequently removing the force to allow the sample to freely recover may repeated as few as 1, 2 or 3 times or as many as 6, 8 or 10 times, for example, to increase the amount of dislocation stabilized secondary phase within the wire material, as discussed in detail below. Thus, after one or more applications of load cycles and the attendant recovery of applied strain $\varepsilon_C$, the length of wire 10 is greater than its original length $L_O$. More particularly, the length of wire 10 after load conditioning is $L_O+ps$, where ps is the permanent set or isothermally non-recoverable strain resulting from plastic, pseudoplastic and other deformation mechanisms, as shown in FIG. 6. Some of this isothermally non-recoverable strain can be recovered in the bulk material by slight heating of the material as discussed above.

As discussed in more detail below in Section III, this isothermally non-recoverable strain is indicative of the amount or volume of the wire material that has been converted from the primary phase to the secondary phase and, upon recovery of the wire material, remains stabilized in the secondary material phase. These localized areas of secondary phase material isolate defects and inhibit crack propagation in the primary phase material.

For example, as calculated in Examples 3-7 below, this isothermally non-recoverable strain may be calculated by measuring the difference in wire length after load removal in a tensile test. Known tensile test devices (including the test device used for the present Working Examples) collect wire length data as the test is conducted. This data, not presented herein, is used to generate the permanent set data presented in the tables. This non-recoverable length, with the original length subtracted therefrom, gives a positive value where isothermally non-recoverable deformation has occurred (i.e., "permanent set"). This difference can then be divided by the original length, the product of which is a strain value representing the isothermally non-recoverable strain. This amount arises from a residual volume of altered material within the wire which has accommodated a given amount of strain not recovered upon load removal. The observed isothermally non-recoverable strain may be divided by the load plateau strain length, which is associated with the forward transformation from parent austenite phase to secondary, stress-induced, martensite phase, thereby providing a quantitative indication of the volume fraction of altered material within the wire.

This volume fraction, referred to as "max. volume martensite %" in Tables 3-7 below is calculated using the following formula:

$$V_m = \frac{INRS}{LPSL}$$

wherein $V_M$ is the maximum volume fraction of secondary phase, INRS is the isothermally non-recoverable strain and LPSL is the loading plateau strain length.

The volume fraction sets an upper limit on the amount of wire material that has been converted to the secondary phase from the primary phase and remains stable at the given test temperature after load removal. That is to say, the total volume of material represented by the non-recoverable strain comprises secondary phase material, and may also comprise other non-primary phase material arising from plastically deformed primary phase material or other deformation phenomena.

It is counter-intuitive that the application of stress to a wire product at a level sufficient to initiate plastic deformation according to the present mechanical conditioning process could be beneficial for the use of that wire product in a medical device that utilizes the shape memory or superelastic characteristic of the wire product. One of ordinary skill in the art would consider a wire product made of a shape memory material that has been subjected to a stress level sufficient to induce any amount of plastic deformation to be compromised in its shape memory or superelastic characteristic and therefore unsuitable for use in a medical device in which this characteristic is desired.

II. DESCRIPTION OF MATERIAL PROPERTIES OF WIRE PRODUCTS MADE IN ACCORDANCE WITH THE PRESENT MANUFACTURING PROCESS

Wire products made of shape memory materials or alloys that have been subjected to the mechanical conditioning process of the present disclosure exhibit several novel physical characteristics and/or novel combinations of physical characteristics, including the following:

1. Isolation of Defects

Figure 7A:
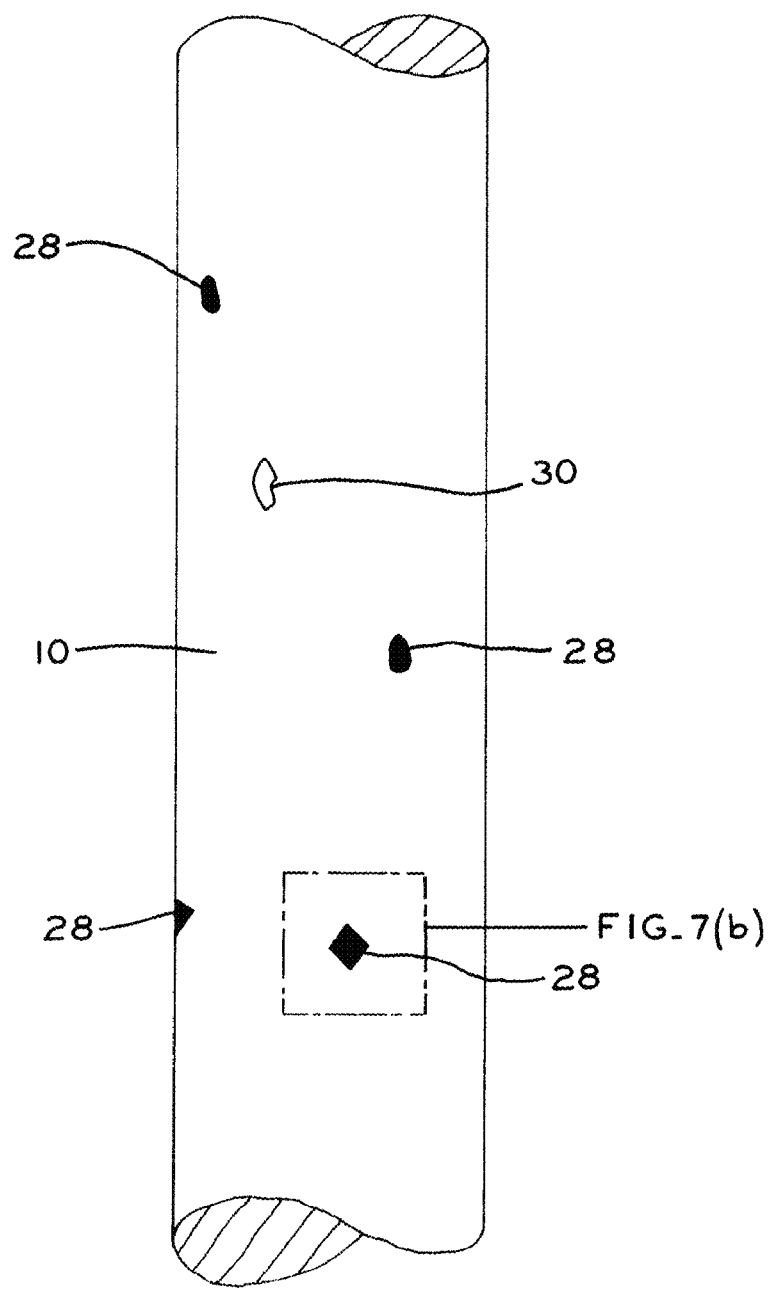
FIG. 7(a) is a view of a portion of a wire having internal and external defects.

Referring to FIGS. 7(a)-(b), shape memory wire 10 may have one or more defects, such as internal defects 28 and/or external defects 30. These defects may include extrinsic defects and/or intrinsic defects such as inclusions or porosity as discussed above, for example.

These defects are isolated in localized fields or areas of secondary phase material by subjecting the wire to mechanical conditioning, as exemplified by the curve shown in FIG. 8. As discussed above, this may be accomplished by applying an engineering stress (and concomitant engineering strain) so that at least some parts of wire 10 experience plastic deformation. In an exemplary embodiment of the present process, however, nearly all of the strain may be recovered upon unloading (FIG. 8).

Figure 9:
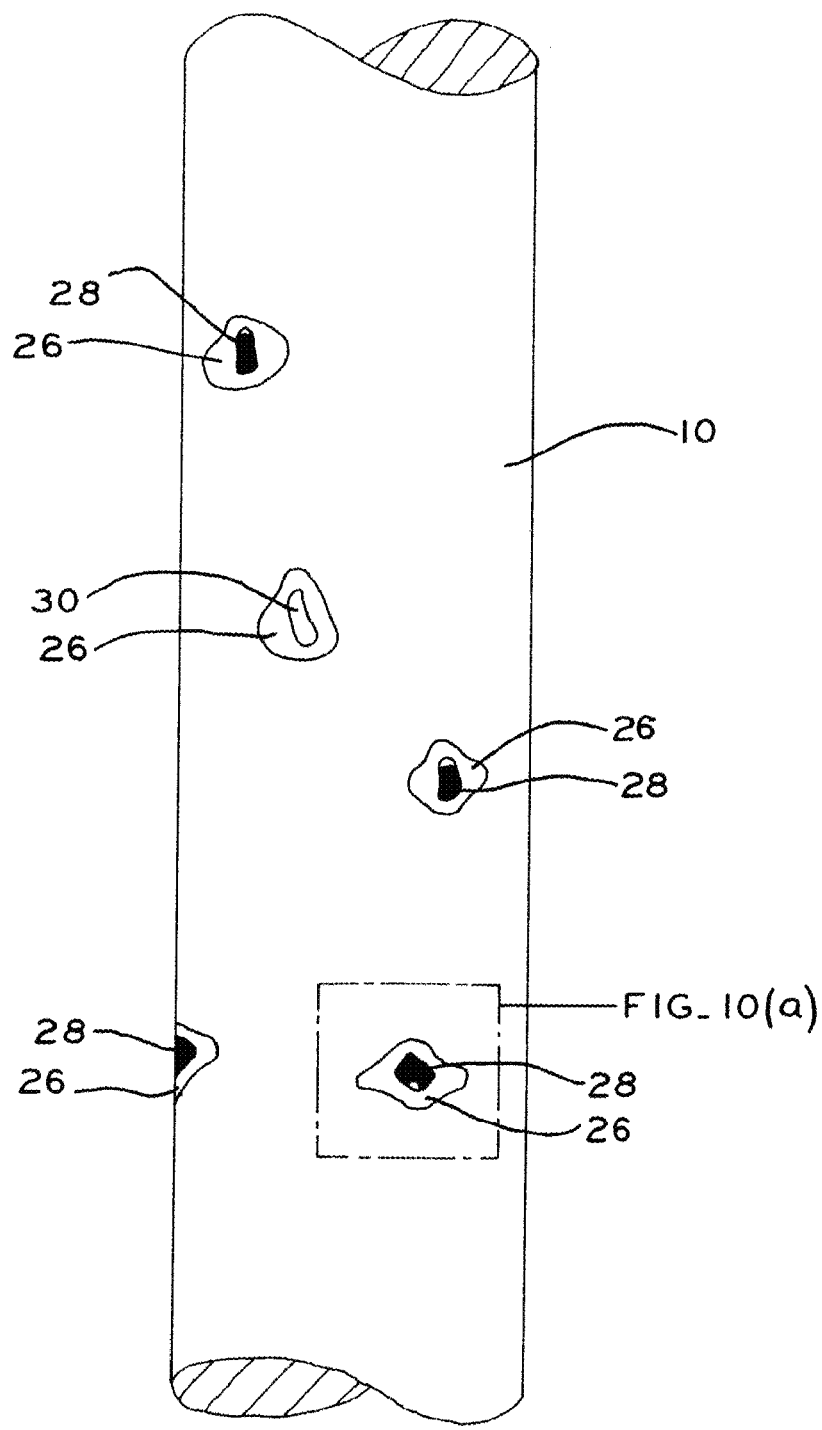
FIG. 9 is a view of a portion of a wire having internal and external defects substantially surrounded by dislocation-stabilized secondary phase.
Figure 10A:
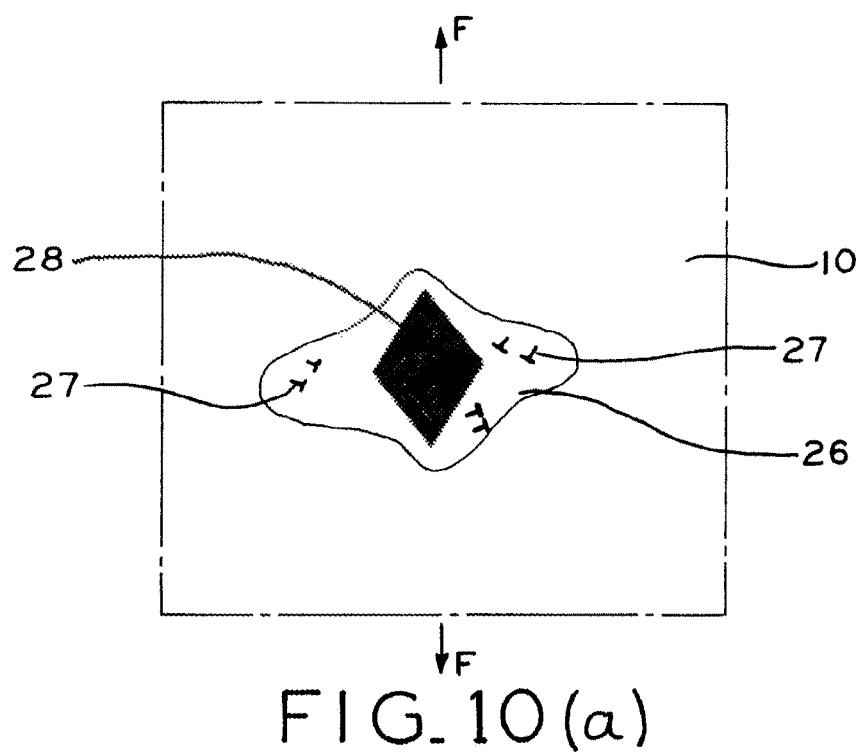
FIG. 10(a) is a fragmentary view of a defect in the wire of FIG. 9 substantially surrounded by dislocation-stabilized secondary phase.
Figure 10B:
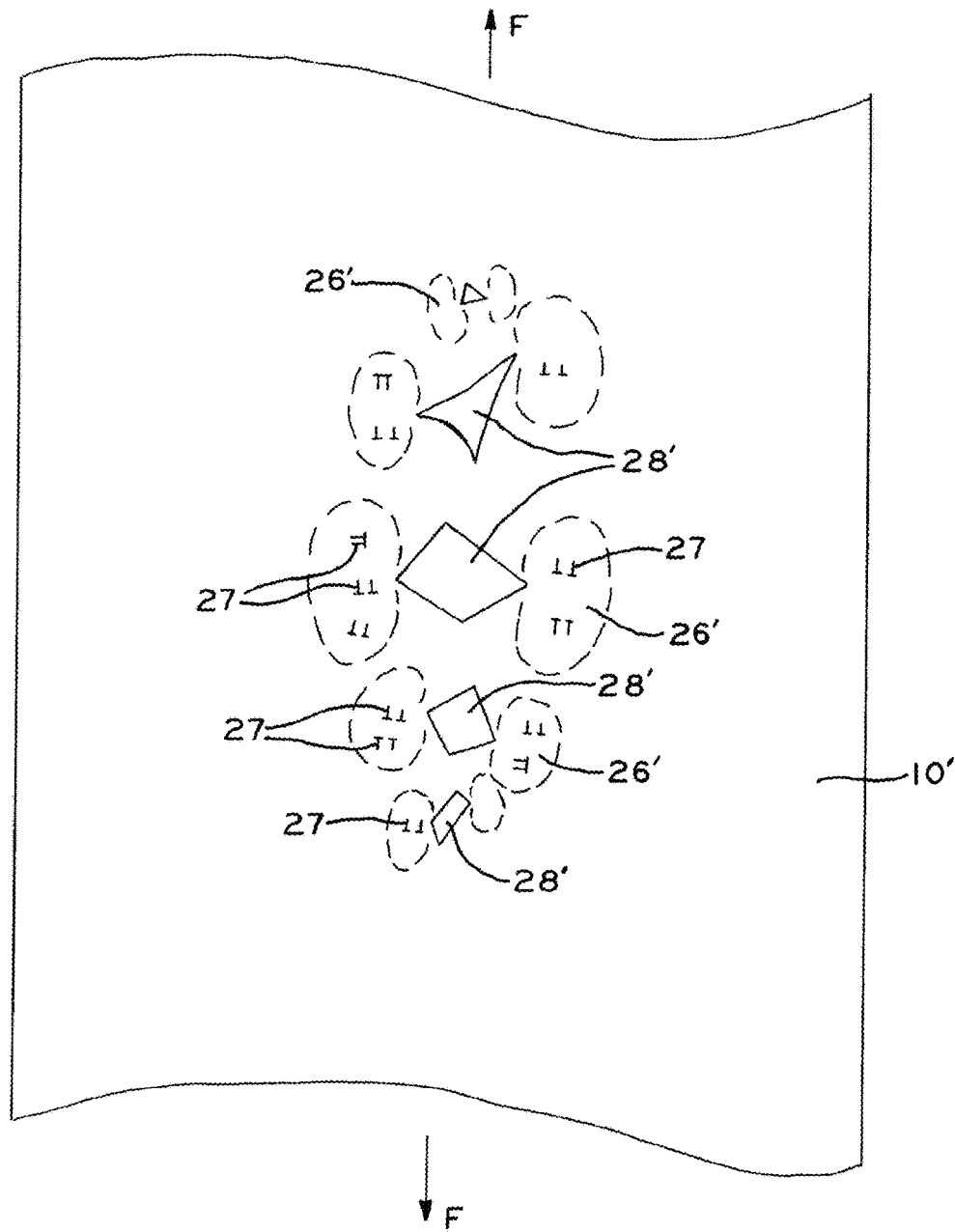
FIG. 10(b) is a view of a portion of a wire having internal and external defects substantially surrounded by dislocation-stabilized secondary phase.
Figure 10C:
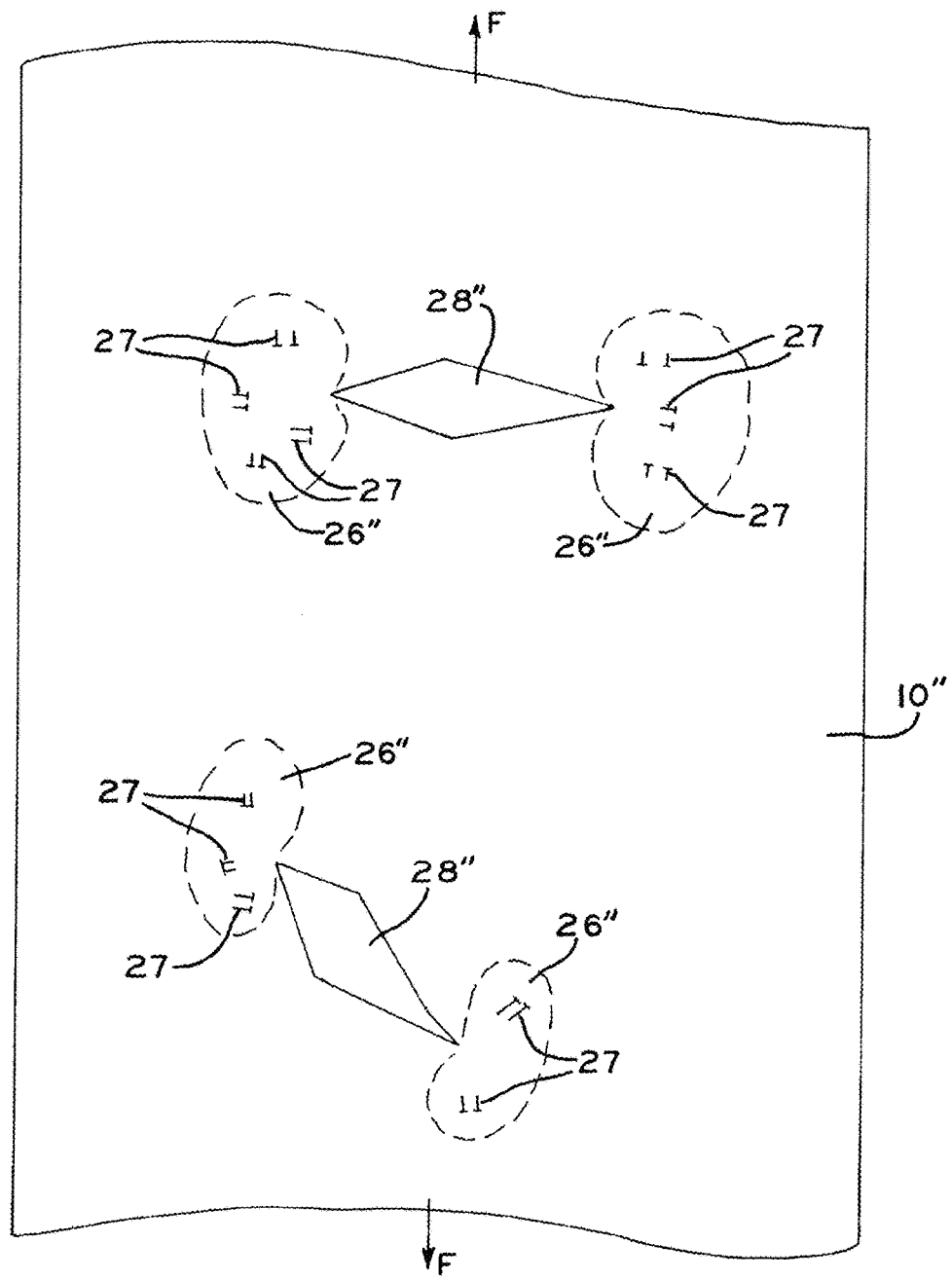
FIG. 10(c) is a view of a portion of a wire having internal and external defects substantially surrounded by dislocation-stabilized secondary phase.

Referring now to FIGS. 9-10(c), mechanical conditioning results in areas of dislocation stabilized B19', R, and/or martensite, shown as secondary phase areas 26 in FIG. 10, forming proximate defects 28 in wire 10. The formation of the secondary phase areas around and/or adjacent defects 28 during mechanical conditioning helps to retard fatigue crack growth in subsequent cyclic loading in a direction emanating from defects 28, as it is known that cracks propagate more slowly in B19', R, and/or martensite than in austenite. However, the bulk of wire 10, where defects are not present, reverts back to the austenite phase after mechanical conditioning, such that the overall wire still exhibits its shape memory or superelastic characteristic while at the same time having an enhanced degree of fatigue strength due to the isolation of defects within the secondary phase material.

Referring still to FIGS. 9-10(c), wires 10, 10' and 10" are shown after mechanical conditioning. As a result of mechanical conditioning in accordance with the present process, areas of dislocation stabilized secondary material phase 26 formed proximate material defects stabilize the defects. That is to say, while the bulk of the wire material reverts back to the primary phase from the secondary phase, localized areas of secondary phase material remain formed proximate material defects. This stabilization of the secondary phase areas 26 is advantageous in that it helps to retard fatigue crack growth in subsequent cyclic loading, for example, as a crack generally propagates more slowly in the secondary (i.e., martensite) phase than in the primary (i.e., austenite) phase.

Stabilization of secondary phase areas 26 is, at least in part, due to plastic deformation 27 comprising dislocations and/or dislocation networks. This plastic deformation acts to stabilize secondary phase 26 after removal of the conditioning mechanical conditioning stress or strain (when primary phase returns to the bulk of the wire material) and during subsequent service. The defect-free portions of the wire material may have less plastic deformation, or may have substantially no plastic deformation. Therefore, this defect-free material will revert back to the primary phase more readily and completely than the localized secondary phase areas near the defects, which have experienced plastic deformation.

As shown in FIGS. 10(a)-(c), the shape, size and/or spatial configuration of secondary phase 26 varies depending upon the characteristics of the defect proximate the localized secondary phase field. In general, the secondary phase field will form around the highest stress areas of the defect, and may not form at lower stress areas. This is because plastic deformation occurs most readily at the site of stress concentrators during the mechanical conditioning process; the dislocation stabilized secondary phase areas, which include some plastic deformation 27, will form at these stress concentration points even though the primary phase portions of the wire are still within a relatively elastic or pseudoelastic (where pseudoelastic is defined as elasticity associated with primary to secondary phase transformation) deformation range. Primary phase material remains present between any pair of defects that are sufficiently far apart, such that their isolation fields to not overlap.

For example, wire 10 shown in FIG. 10(a) has a secondary phase area 26 extending around substantially the entirety of defect 28. The geometry of defect 28, as well as the direction application of force F, determines the overall shape of secondary phase area 26.

As shown in FIG. 10(b), wire 10' has defects 28' with stabilized secondary phase areas 26' at the highest stress concentration areas created by the application of force F. Plastic deformation 27 also occurs within secondary phase areas 26' as discussed above. Some of secondary phase areas 26' are adjacent one another and have overlapping boundaries, so that a defect 28' and another nearby defect 28' will influence one another.

Similarly, wire 10" shown in FIG. 10(c) has multiple defects 28" with stress fields 26" and plastic deformation 27. Again, the stress fields 28" form at the highest stress concentration points, which are a function of the geometry of defects 28" and the direction of application of force F (shown as a longitudinal force along the axis of wire 10") as well as the temperature of the material during force application.

In this manner, shape memory material wire subjected to the present mechanical conditioning process exhibits an enhanced fatigue life and fatigue strain threshold. Moreover, a shape memory wire made in accordance with the present process retains overall material properties consistent with wire in the austenitic phase, while exhibiting inhibition of crack propagation at defect sites consistent with the martensitic phase.

2. Increased High-Cycle Fatigue Resistance

Figure 11:
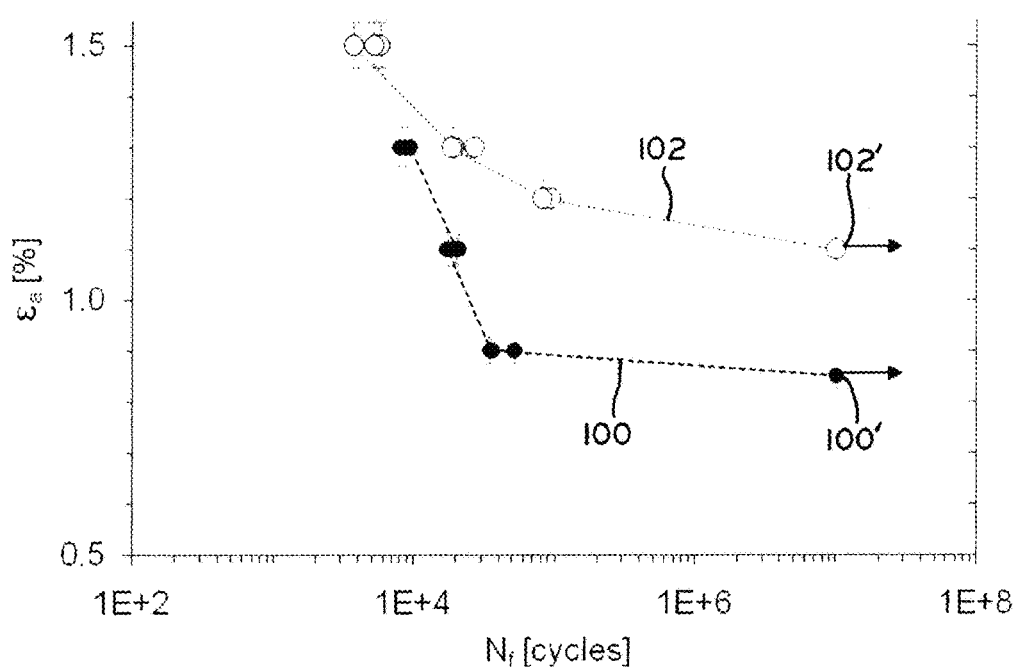
FIG. 11 is a graphical strain-life representation of rotary beam fatigue data generated in accordance with Example 1 under the following test conditions: R=−1, T=298 K, f=60 $s^{-1}$; environment: quiescent air, N=5 at each strain level.
Figure 14:
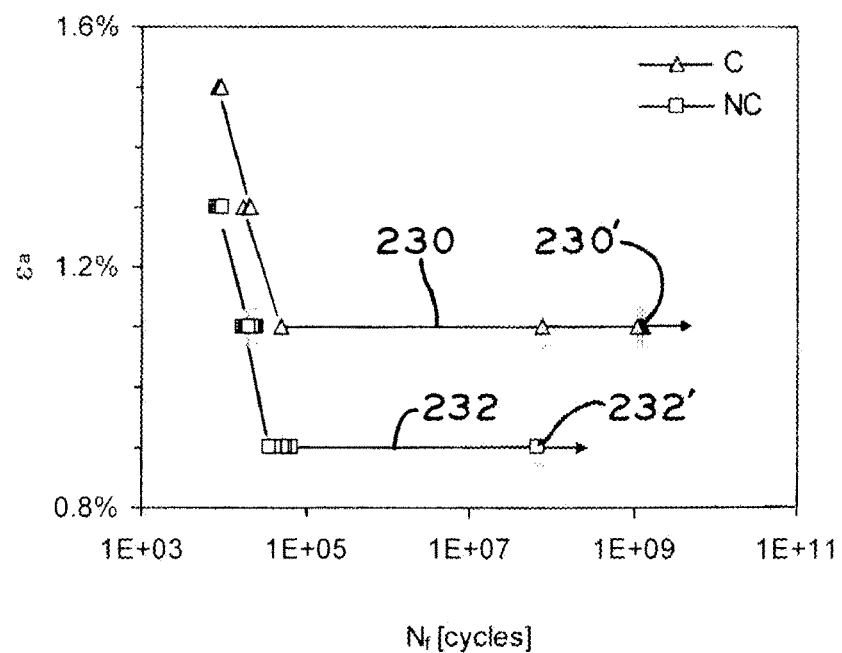
FIG. 14 is a graphical representation of rotary bend fatigue data for conditioned (C) and non-conditioned (NC) samples under the following test conditions: T=300 K, rate=60 $s^{-1}$, R=−1, with a maximum stress error=3% and a maximum cycle count error=0.5%.

As a result of the isolation of defects and/or defect boundaries (i.e. the sites along the defect/primary phase boundary most susceptible to stress concentration and crack propagation) in a secondary phase area or field, mechanical conditioning increases the fatigue life and fatigue-strain threshold of the shape memory wire. As discussed in Section III, wire conditioned in accordance with an embodiment of the present disclosure exhibited a gain in the fatigue strain limit at 100 million ($10^8$ cycles of greater than 25% (FIG. 11). Also, as shown in FIG. 14, conditioned wire demonstrated an upward strain shift of greater than 20% at a 10 million ($10^7$) cycle life (i.e., 1.1% engineering strain versus 0.9% engineering strain). Further, eight samples of this conditioned material survived more than $10^9$ cycles and were still running at the time conclusion of Example I discussed below.

3. Increased Damage Tolerance and Low-Cycle Fatigue Resistance

Figure 15:
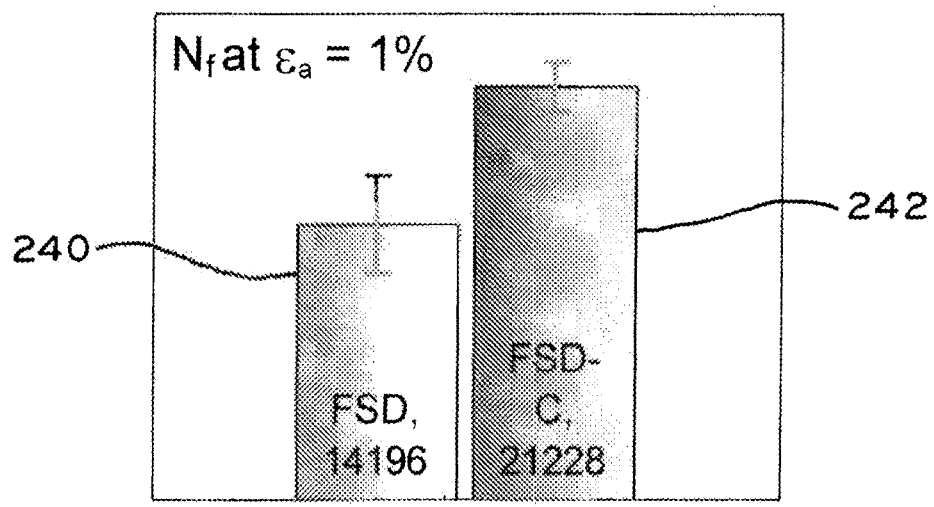
FIG. 15 is a graphical representation of single test level (1% alternating engineering strain) data for FIB-sharp defect (FSD) and FSD-conditioned (FSD-C) samples, with the extension bars in the inset representing the data spread for n=3 samples.
Figure 18A:
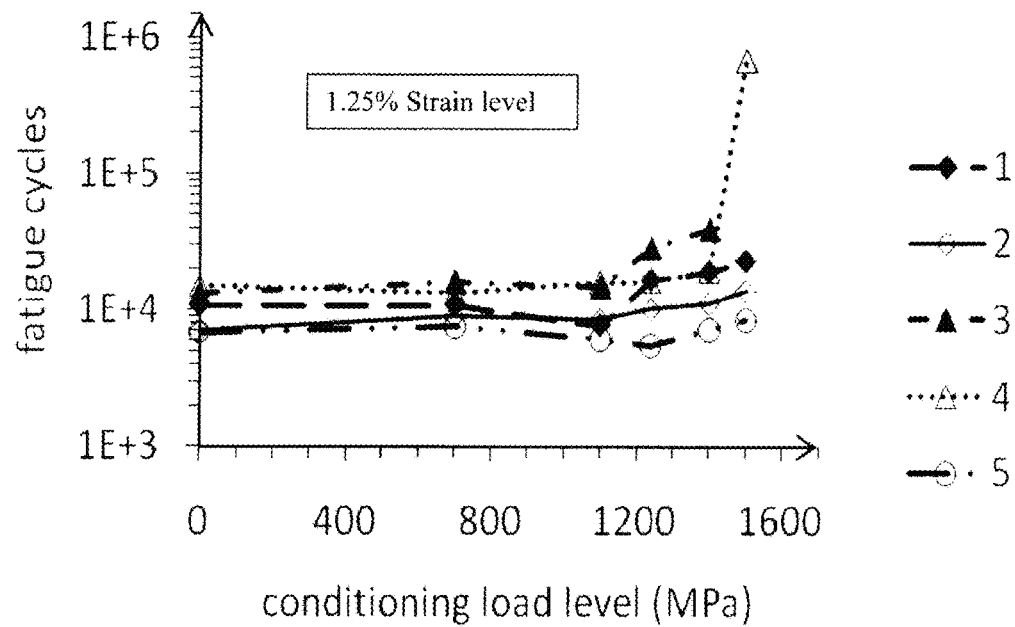
FIG. 18(a) is a graph showing cycles to failure for five sets of wire samples, where a sample from each set of wires has been mechanically conditioned with a given level of engineering stress, and where the wires were tested at a 1.25% strain level.
Figure 18B:
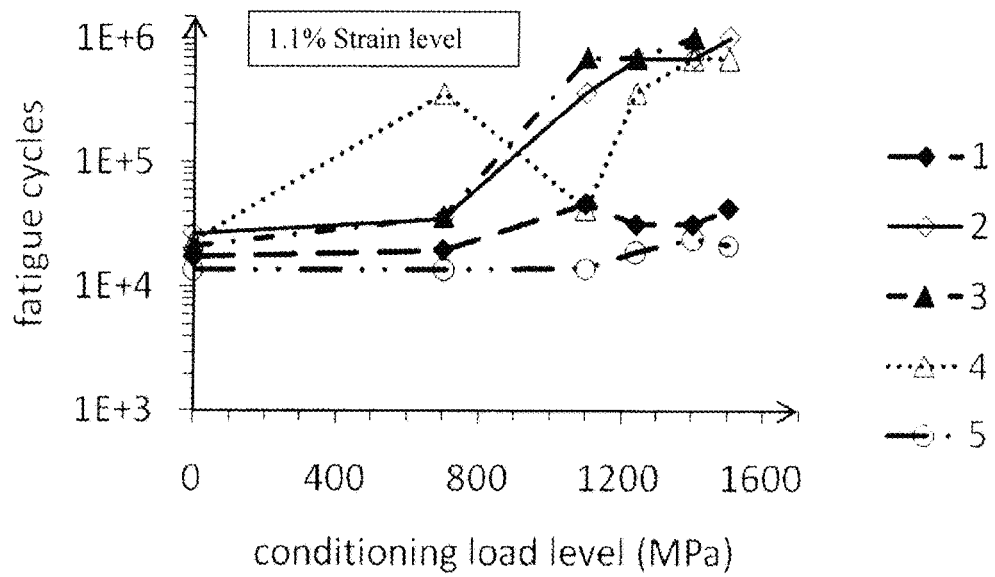
FIG. 18(b) is a graph showing cycles to failure for the five sets of wire samples shown in FIG. 18(a), where a sample from each set of wires has been mechanically conditioned with a given level of engineering stress, and where the wires were tested at a 1.1% strain level.

As discussed in Section III at Example 2, wire conditioning in accordance with an embodiment of the present disclosure demonstrated increased tolerance of damage to the wire. Three specimens with focused ion beam (FIB)-milled sharp defects were tested at an alternating strain of 1% in the conditioned and non-conditioned states. As shown in FIG. 15, Conditioned samples demonstrated a 50% increase in damage tolerance compared with the non-conditioned samples.

4. High Recoverable Strain, Low Residual Strain

As shown in FIGS. 13(a)-(c), greater than 8% recoverable engineering strain was observed with zero residual strain and good plateau stresses at body temperature (i.e., 310 K) after mechanical conditioning.

This recoverable strain renders wire made in accordance with the present disclosure particularly suitable for certain medical device applications. As mentioned above, this is a counter-intuitive result. Typically, wire made of a shape memory or superelastic material which has been subjected to forces sufficient to cause any plastic deformation in the wire material would be considered "damaged", and therefore unsuitable for use in any medical device application. The surprising result of the present process is that, under proper mechanical conditioning parameters as discussed herein, wire subjected to such forces is actually superior for medical device applications.

III. EXAMPLES

The following non-limiting Examples illustrate various features and characteristics of the present invention, which are not to be construed as limited thereto.

The examples offer analysis of the effect of mechanical conditioning in fine (such as less than 250 µm diameter) Nitinol wire, and particularly of the effect of stress riser or defect isolation.

Example 1

Fatigue Resistant Nitinol Intermetallic Wire

Nanocrystalline, nominally Ti-56 wt. % Ni Nitinol wire ("NiTi wire") was manufactured to create a superelastic, precipitate free wire with a median grain size of 50 nm. An exemplary process for creating such a wire is described in U.S. patent application Ser. No. 12/563,062, entitled FATIGUE DAMAGE RESISTANT WIRE AND METHOD OF PRODUCTION THEREOF, filed Sep. 18, 2009, the disclosure of which is hereby expressly incorporated by reference herein in its entirety.

The resulting wire was drawn through diamond drawing dies beginning at a diameter of 0.230 mm and ending at a diameter of 0.177 mm to yield a retained cold work level of about 40% cold work. The wire was then continuously annealed at a temperature of 773K-873K for less than 60 seconds, to yield a 50 nm grain size as verified by TEM electron microscopy scanning. Specifically, field emission scanning electron microscopy or transmission electron microscopy (TEM) is used to gather an image containing, for example, several hundred crystals or grains exhibiting strong grain boundary contrast. Next, the image is converted to a binary format suitable for particle measurement. Resolvable grains are modeled with ellipsoids and subsequently measured digitally yielding statistics regarding the crystal or grain size, such as the average size, maximum size, and minimum size. The resulting average crystal size is taken to be the average crystal size for the material from which the sample was taken. Grain size verification is discussed in detail in U.S. patent application Ser. No. 12/563,062, entitled FATIGUE DAMAGE RESISTANT WIRE AND METHOD OF PRODUCTION THEREOF, filed Sep. 18, 2009, incorporated by reference above.

After annealing, the wire of the present Example was subjected to cyclic tensile testing and was determined to exhibit pseudoelasticity out to greater than 10% engineering strain. A first wire sample was preserved at this point in the process.

The remainder of the wire was then subjected to mechanical conditioning, as described in detail above, by loading the wire to about 12% axial engineering strain (i.e., 0.12 units), completely releasing the load, reloading to about 12% engineering strain, and once again completely releasing the load. A second wire sample was preserved after this point in the process.

The first and second wire samples were subjected to rotary beam fatigue testing. Referring now to FIG. 11, the first, non-mechanically conditioned sample generated data curve 100 exhibiting a 100 M cycle engineering strain limit of about 0.85% at N=10 data points, shown by right most data point 100' of the curve 100. The second, mechanically conditioned sample generated data curve 102 exhibiting a 100 M cycle engineering strain limit of about 1.1% at N=10 data points, exemplifying a greater than 25% gain in the fatigue strain limit at 100 M cycles, shown by right most data point 102' of curve 102.

Example 2

Mechanical Conditioning of Superelastic NiTi Wire for Improved Fatigue Resistance In this example, the effects of mechanical overload conditioning of superelastic wire and the possibility of increased fatigue damage resistance associated with near-defect, plasticity-locked phase transformation were investigated. In thin wires, where plane stress dominates, it is expected that sufficient loading will result in phase transformation near the largest or shape-conducive crack-like defects, such as constituent inclusion particles, before conversion of the bulk, defect-free material.

1. Experimental Technique

Samples for this Example were subjected to a total engineering strain departure, measured by crosshead extension, of about 11.5%. Conditioning was applied by approaching the martensitic yield point at 295 K using strain-rate-controlled loading in order induce some dislocation locking of stress-transformed material in the vicinity of stress concentrators. Referring now to FIG. 8, the conditioning cycle comprises a strain-controlled ramp to a stress level of 1240 MPa engineering stress, resulting in an engineering strain of about 11.5%, followed by a 3 second hold, and finishing with a strain-controlled ramp to zero load.

In order to prepare samples for this Example, Nitinol wire with an ingot austenite start temperature, AS, of 243 K, having Ti-56 wt. % Ni was repetitively drawn and annealed from a diameter of 2 mm to a diameter of 177 µm in accordance with the process described above. At this stage, wires were continuously annealed at 770 to 800 K. Final cold working was completed using diamond dies to draw round wire with a diameter of 150 µm prior to continuous, reel-to-reel annealing at 750 to 780 K under constant engineering stress for less than 60 seconds to effect linear shape setting. The final wire comprised a room-temperature-superelastic Nitinol wire with an active austenitic finish temperature, $A_f$, of 280 K and an approximately 120 nm thick, dark brown oxide layer similar to that disclosed in an article by the present inventor entitled "Structure-Property Relationships in Conventional and Nanocrystalline NiTi Intermetallic Alloy Wire" and published in the *Journal of Materials Engineering and Performance*, February 2008, ISSN 1544-1024, pgs. 1-6, the entire disclosure of which is hereby expressly incorporated by reference herein.

Figure 12A:
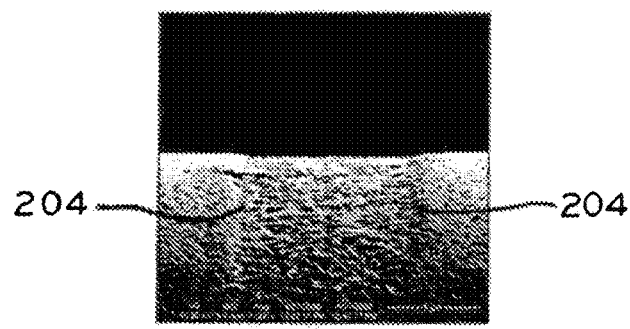
FIG. 12(a) is a secondary electron (SE) image of a 100 nm deep cue mark for optical determination of defect zone.
Figure 12B:
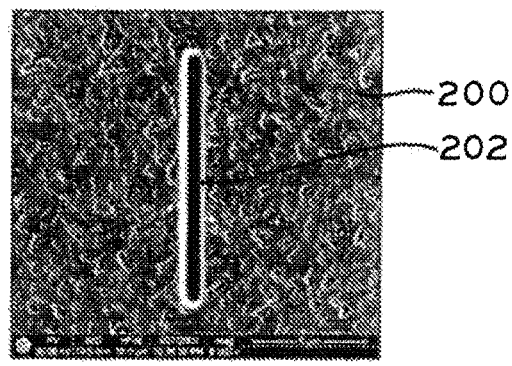
FIG. 12(b) is an image of a transversely oriented, 10×3×0.5 μm (T×R×L) FIB-milled sharp defect.
Figure 12C:
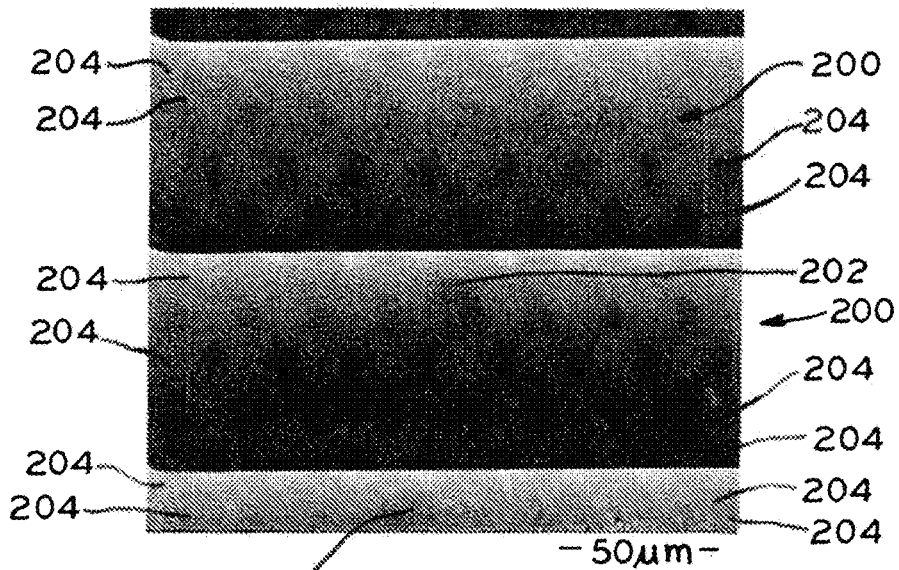
FIG. 12(c) is an image that provides an overall view of a sharp defect zone.

Focused ion beam (FIB)-milled sharp defects 202 ("FSD") were then milled into material 200 of each sample in order to act as preferential sites of incipient fatigue crack formation and to facilitate user-defined damage localization and monitoring. An FEI dual-beam (Nova 200 NanoLab) focused ion beam (FIB) with in situ scanning electron microscopy (SEM) was used to simultaneously monitor samples by SEM during the FIB milling process. A 30 keV Ga+ ion beam was used to precisely mill transverse defects into wire specimens at a 0.50 nA beam current. Defects 202 were of consistent dimension measuring 10 µm transverse length by 3 µm radial depth by 0.5 µm axial surface width, an example of which is shown in FIGS. 12(*a*)-(*e*). Cue lines 204 (FIG. 12(*a*)) were milled into the oxide surface at a depth of about 50 nm on either side of each sharp defect in order to enhance optical detection for accurate placement in fatigue test gages after removal from the SEM chamber. As shown in FIGS. 12(*a*)-(*e*), the cue lines were of sufficient depth to create a visually detectable gradient associated with the reduced oxide thickness, while shallow enough to minimize undesirable mechanical impact.

Electron microscopy of fracture surfaces was carried out using a Hitachi S4800 field emission SEM (FE-SEM) operated at 10 to 20 kV. Transmission electron microscopy samples were extracted and prepared using the FIB/SEM dual beam equipment previously mentioned with an in situ sample manipulator for thin foil removal and transport to TEM grids. Additional details regarding this method can be found in the article by the present inventor, which is incorporated by reference herein above, namely the article entitled "Structure-Property Relationships in Conventional and Nanocrystalline NiTi Intermetallic Alloy Wire" and published in the *Journal of Materials Engineering and Performance*, February 2008, ISSN 1544-1024, pgs. 1-6. TEM imaging and diffraction experiments were carried out on a 200 kV machine equipped with a $LaB_6$ emitter (Tecnai 20, FEI Company, Oregon).

Cyclic and monotonic uniaxial tensile properties were measured at an ambient temperature of 295 K at a strain rate of $10^{-3}$ s$^{-1}$ using an Instron Model 5565 Tensile Test Bench equipped with pneumatic, smooth face grips. Six hundred grit emery-cloth was used to reduce grip-specimen interface slip. Elevated temperature testing was completed on an equivalent tensile bench fitted with an environmental chamber capable of maintaining a temperature of 310±0.5 K.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency. Data have recently been presented by Robertson and Ritchie, in an article entitled "In vitro fatigue-crack growth and fracture toughness behavior of thin-walled superelastic Nitinol tube for endovascular stents: A basis for defining the effect of crack-like defects", published in *Biomaterials* 28, 2007, pgs. 700-709, suggesting that high rate testing may well estimate in vivo fatigue failure lifetimes.

As shown in FIGS. 13(*a*)-13(*c*), specimens from each group, non-conditioned (NC) and conditioned (C), were tested at alternating engineering strain (½ peak-to-peak amplitude) levels ranging from 0.8 to 1.6% to a maximum of about $10^9$ cycles or 200 days test time. Further, specimens with FSD 202 were tested at 1% engineering strain before and after conditioning. The FSD zone was located at the apex of the fatigue bend by optical positioning using the cue marks 204 as guides.

2. Results

The resulting tensile data is shown graphically in FIGS. 13(*a*)-(*c*). As noted above, the conditioning cycle comprised a strain-controlled ramp to a stress level of 1240 MPa engineering stress followed by a 3 second hold, finishing with a strain-controlled ramp to zero load. This conditioning cycle generated data curve 220, shown in FIGS. 13(*a*)-(*c*). The total engineering strain departure for this cycle, measured by crosshead extension, was 11.5%. Conditioning initially resulted in 0.3% residual strain comprising both plastic and pseudo-plastic strain contributions.

The martensite to austenite reversion plateau stress associated with unloading was significantly reduced during unloading from the conditioning cycle, but was observed to elevate in subsequent testing to 8% engineering strain. Some of this effect can be accounted for by strain rate differences: the conditioning cycle was run at a significantly higher strain rate than the 8% test cycles. High strain rates can cause heating during loading and cooling during unloading resulting in increasing stress hysteresis. Further testing of a C sample at body temperature (310 K) generated data curve 226 depicted on FIGS. 13(*a*)-(*c*) by circular marks 226', showing elevation of the unloading plateau stress to levels greater than an NC sample at 295 K, shown as data curve 222 with square-shaped marks 222. This result was consistent with known test temperature-plateau stress relationships.

The conditioned sample at 295 K, shown as curve 224 on FIGS. 13(*a*)-(*c*) with triangle-shaped marks 224', exhibited a downward shift in the unloading plateau stress. This can be attributed to plastic deformation, some of which may be directly beneficial to resistance against subsequent fatigue crack growth. The lack of significant shift in the strain length of the plateaus indicates that plastic deformation to the overall microstructure was minimal during overload conditioning.

FIG. 14 illustrates the observed differences in fatigue performance for conditioned wire specimens, shown as data curve 230 with triangular-shaped marks 230', versus non-conditioned (NC) wire specimens, shown as data curve 232 with triangular-shaped marks 232'. The conditioning resulted in an upward strain shift of greater than 20% at the $10^7$ cycle life (i.e., 1.1% engineering strain versus 0.9% engineering strain). Eight samples of the conditioned material survived more than $10^9$ cycles and were still running at the time conclusion of the experiment.

As shown in FIG. 15, three FSD specimens in each of the NC and C states were tested at an alternating strain of 1%. In this case, the FSD-C group generated data bar graph 242, showing an average of 21,228 cycles to failure with a margin of error indicated at the top of the bar. The FSD-NC group generated data bar graph 240, showing an average of 14,196 cycles to failure with a margin of error indicated at the top of the bar. Thus, the conditioned wire samples outperformed the non-conditioned samples by 50%. All FSD samples failed considerably before the non-FSD samples; this is attributable to the geometry of the FIB-milled defects, which were purposefully milled larger and sharper than the 2-6 µm inclusion particles typically found at fatigue failure sites in this grade of Nitinol wire in order to direct site-specific, locatable failure for study.

A microstructurally distinct region resulting from the mechanical conditioning was found within an approximately 500 nm radius of the approximately 10 nm width FSD crack root. FIG. 16 shows the results of TEM work performed to help elucidate mechanisms giving rise to mechanical property changes associated with the mechanical conditioning. The selected area diffraction patterns 250, 252 in FIG. 16, outside of and within the distinct FSD concentration zone respectively, reveal significant differences in contributing bright field contrast signal. A typical polycrystalline, B2 pattern 250 was observed at approximately 1 µm from the crack tip, while the selected area diffraction pattern adjacent to the root, shown as 252, revealed what appears to be superimposed diffuse rings, B2 polycrystalline reflections, as well as some evidence of ½ (110) reflections associated with the B19' martensitic phase. Also evident is a significant increase in dislocation density and associated contrast.

The diffuse (110) rings observed within the FSD zone, shown in the left and upper-right insets of FIG. 16, may be related to partial amorphization and/or due to (110) reflection splitting and the presence of ½(110) reflections associated with a mixed B2-B19' structure.

The narrowest ductile striations were observed in conditioned samples near the FSD incipient crack front. High resolution SEM (HR-SEM) analysis of fatigue failure sites in NC and C specimens was completed and the stress intensity was estimated based on the probable crack front location at the examined site using assumptions of a semi-elliptical crack in an infinite cylinder. Referring to FIG. 17, a crack growth rate plot as a function of the estimated stress intensity factor (not taking into account crack closure effects) is shown, with square-shaped marks 260 indicating data on non-conditioned material and triangle-shaped marks 262 indicating conditioned material. The difference between the two data sets may suggest martensitic growth rate inhibition.

In this example, it has been demonstrated that mechanical conditioning of superelastic NiTi wire results in improved fatigue performance, while maintaining good mechanical properties. In addition, greater than 8% recoverable engineering strain was observed with zero residual strain and good plateau stresses at body temperature after mechanical conditioning. Further, an increase in the strain fatigue limit of greater than 20% at $10^7$ cycles is observed in conditioned versus non-conditioned wire with an observed increase in low cycle life of 50%. The tensile overload conditioning treatment also resulted in a mixed-phase microstructure in the vicinity of stress concentrators that comprises increased dislocation density and possible plasticity-induced or roughness-induced crack closure.

The presence of plasticity in the FSD region may also contribute to increased fatigue performance due to residual stresses which offset the effective crack-opening stress intensity range. The reduction in the operating stress intensity range can serve to increase the effective $\Delta K_{th}$ fatigue threshold (defined above) thereby elevating the strain load level required to initiate or maintain crack growth. The mixed microstructure may also promote crack front tortuosity thereby precluding crack arrest associated with roughness-induced closure at near-threshold crack growth conditions.

Introduction to Examples 3-7

For examples 3-7, various wire materials were tested in a similar manner for comparison to one another. FIGS. 18(a)-(d) show results for wire materials from each of Examples 3-7, with each Figure representing a different strain condition (as indicated on each respective Figure). Table 1, below, indexes the Example materials:

TABLE 1

Index of Example Materials for Examples 3-6

| Example | Nitinol type | Nominal Composition (weight %) | Actual Diameter (mm) | Shape Set Temperature (K) | Surface Finish Description | Austenitic Finish Temperature Af (K) |
|---|---|---|---|---|---|---|
| 3 | NiTi #1 | 56Ni—Ti | 0.151 | 740-800 | Oxide | 280 |
| 4 | NiTi #2 | 55.8Ni—0.25Cr—Ti | 0.269 | 740-800 | Oxide | 283 |
| 5 | NiTi #4 | 55.8Ni—Ti | 0.302 | 740-800 | Oxide | 298 |
| 6 | NiTi #1 | 56Ni—Ti | 0.076 | 740-800 | Etched | 288 |
| 7 | NiTi #1 | 56Ni—Ti | 0.638 | 740-800 | Polished | 291 |

FIGS. 19(a)-(e) also show results for wire materials from each of Examples 3-7, with each Figure representing a stress-strain curve for a corresponding Example. Table 2, below, indexes the mechanical conditioning regimes applied to each wire product shown in FIGS. 19(a)-(e). The "regime" number corresponds to a given curve on each figure, as indicated by the corresponding number on the legend at the right side of each of FIGS. 19(a)-(e), where, the digit preceding the decimal point in X.X refers to the Example (e.g. 1, 2, 3, 4, and 5 correspond to Examples 3, 4, 5, 6, and 7 respectively), and the digit following the decimal point corresponds to regimes 1, 3, 4, 6, and 7 given below in Table 2.

TABLE 2

Index of Conditioning Regimes for Examples 3-6

| Regime (See also legends at right of FIGS. 19(a)-(e)) | Ramp rate (engineering strain/min) | Hold stress (MPa) (See also X-axes in FIGS. 18(a)-(d)) |
|---|---|---|
| 1 | 0.10 | 700 |
| 3 | 0.10 | 1100 |
| 4 | 0.10 | 1240 |
| 6 | 0.10 | 1400 |
| 7 | 0.10 | 1500 |

Results shown in Tables 3-7 show data used to create FIGS. 19(a)-19(e) respectively. Thus, Tables 3-7 correspond with Examples 3-7, respectively.

Example 3

Mechanical Conditioning of Superelastic NiTi Wire for Improved Fatigue Resistance In this example, the effects of mechanical overload conditioning of superelastic wire and the possibility of increased fatigue damage resistance associated with near-defect, plasticity-locked phase transformation were further investigated over a broader range of loads as compared to Example 2.

1. Experimental Technique

Figure 19A:
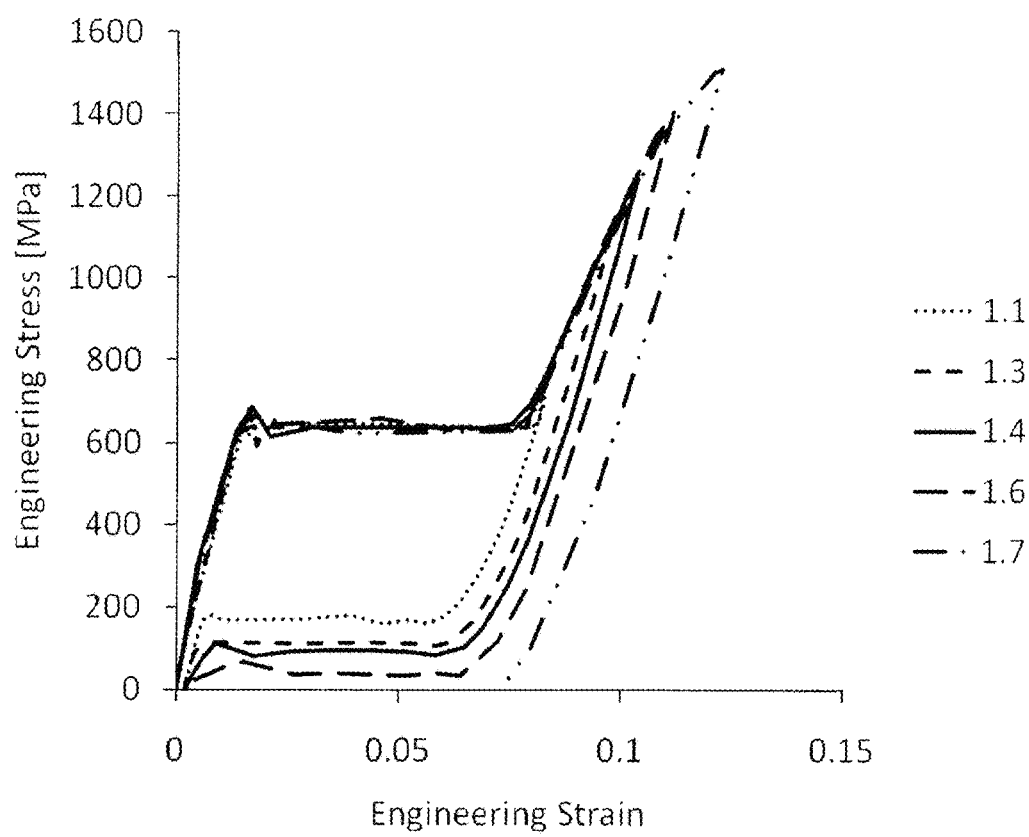
FIG. 19(a) is a stress-strain curve for five wire samples, where each wire sample was loaded using the conditioning regime indicated by the legend at the right of the figure and described in Table 2.

Samples for this Example were subjected to a total engineering strain departure, measured by crosshead extension, ranging from about 8% to 12.5% Conditioning was applied by approaching the martensitic yield point at 295 K using strain-rate-controlled loading in order induce some dislocation locking of stress-transformed material in the vicinity of stress concentrators. Referring now to FIG. 19(a), the conditioning cycle comprises a strain-controlled ramp to five stress levels of 700, 1100, 1240, 1400, and 1500 MPa engineering stress, resulting in an engineering strain of about 8.3%, 9.8%, 10.3%, 11.1% and 12.2% respectively, followed by a 3 second hold, finishing with a strain-controlled ramp to zero load.

In order to prepare samples for this Example, Nitinol wire with an ingot austenite start temperature, As, of 243 K, having Ti-56 wt. % Ni was repetitively drawn and annealed from a diameter of 2 mm to a diameter of 201 µm in accordance with the process described above. At this stage, wires were continuously annealed at 950 to 1000 K. Final cold working was completed using diamond dies to draw round wire with a diameter of 151 µm prior to continuous, reel-to-reel annealing at 750 to 780 K under constant engineering stress for 40 to 80 seconds to effect linear shape setting. The final wire comprised a room-temperature-superelastic Nitinol wire with an active austenitic finish temperature, $A_f$, of 280 K and an approximately 120 nm thick, dark brown oxide layer similar to that disclosed in an article by the present inventor entitled "Structure-Property Relationships in Conventional and Nanocrystalline NiTi Intermetallic Alloy Wire" and published in the *Journal of Materials Engineering and Performance*, February 2008, ISSN 1544-1024, pgs. 1-6, which is incorporated by reference above.

Cyclic and monotonic uniaxial tensile properties were measured at an ambient temperature of 295 K at a strain rate of $10^{-3}$ s$^{-1}$ using an Instron Model 5565 Tensile Test Bench equipped with pneumatic, smooth face grips. Six hundred grit emery-cloth was used to reduce grip-specimen interface slip.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency.

As shown in FIGS. 18(a)-(d), three specimens from each group at each conditioning cycle, ranging from 0 MPa which indicates non-conditioned wire to 1500 MPa which indicates the maximum conditioning load used, were tested at alternating engineering strain (½ peak-to-peak amplitude) levels ranging from 0.80 to 1.25% strain to a maximum of about $10^6$ cycles. The total samples tested for each conditioning load regime for each sample was 12 resulting in a total of 72 fatigue samples tested for this portion of the study. Samples which did not fracture after $10^6$ cycles were stopped and recorded.

2. Results

The resulting tensile data is shown graphically in FIGS. 18(a)-(d) as line 1 on each curve. As noted above, the conditioning cycle comprised a strain-controlled ramp to a stress level of 0, 700, 1100, 1240, 1400 or 1500 MPa engineering stress, as indicated along the horizontal axis of the plot, followed by a 3 second hold, finishing with a strain-controlled ramp to zero load.

This conditioning cycle generated data curves 1.1, 1.3, 1.4, 1.6 and 1.7 shown in FIG. 19(a). The total engineering strain departure for respective cycles, measured by crosshead extension, was about 0%, 8.3%, 9.8%, 10.3%, 11.1% and 12.2% for increasing load levels respectively. Conditioning resulted in residual strains (i.e. isothermally non-recoverable strains) of respectively 0%, 0.19%, 0.20%, 0.24%, 0.17%, ad 7.3% respectively.

FIGS. 18(a) to (d) illustrate the observed differences in fatigue performance for non-conditioned (e.g. 0 load level on x-axis) and conditioned wire specimens (700, 1100, 1240, 1400, and 1500 MPa on the x-axis) The conditioning resulted in an upward cycle life shift of at least 55% and 3000% at the 1.25% and 0.95% alternating strain test levels respectively at a conditioning load level of 1240 MPa. An overall upward trend in lifetime for a given test strain level was observed for increasing conditioning load through 1500 MPa. Most samples of the material conditioned at greater than 1240 MPa survived more than $10^6$ cycles and were still running at the time of conclusion of the experiment for test strain levels below 0.95%.

Figure 20:
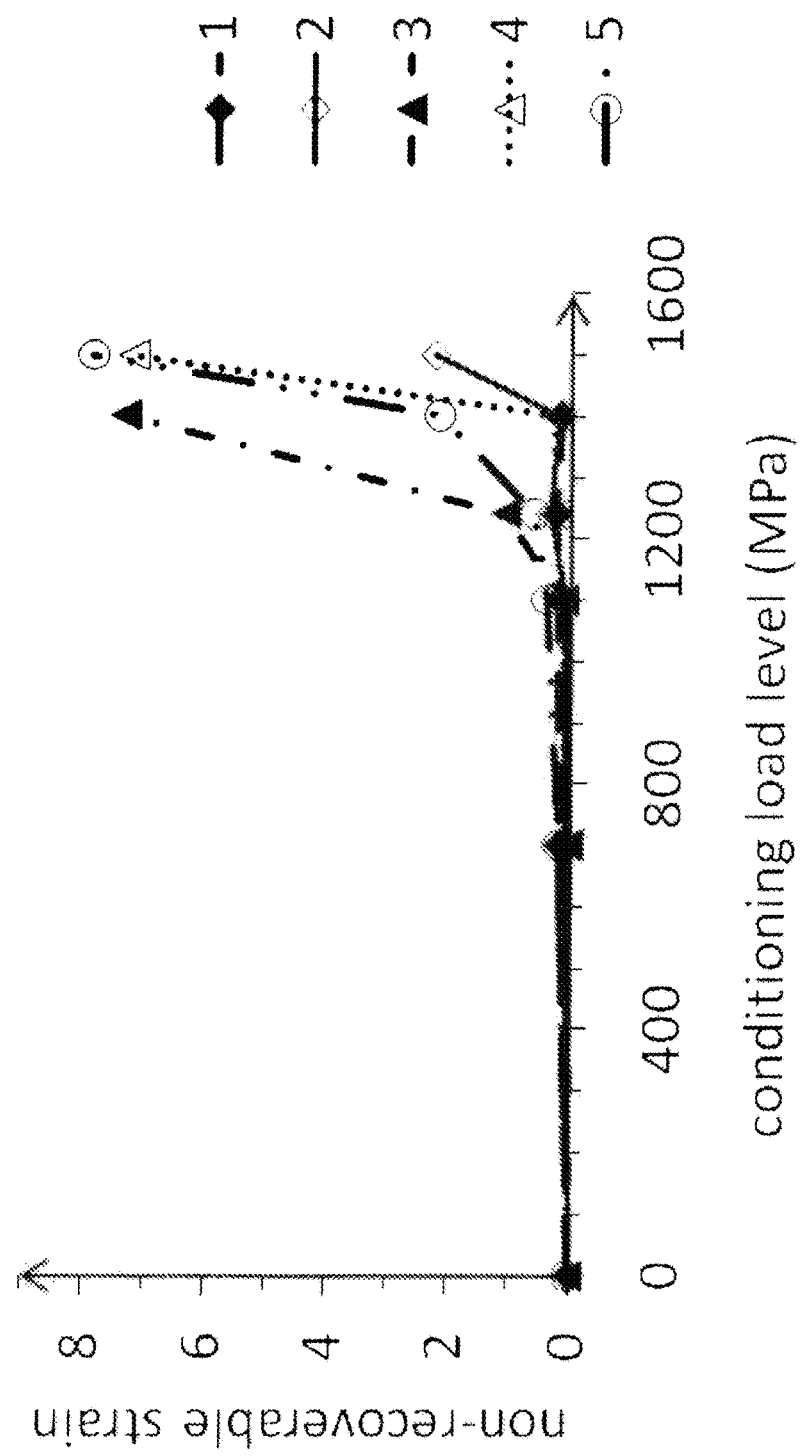
FIG. 20 is a graph showing the percentage of isothermally non-recoverable strain in various wire materials as a function of a mechanical conditioning parameter.

FIG. 19(a) illustrates the observed tensile behavior during load conditioning of each sample. In each case, an upper bound of the maximum volume of retained martensite was calculated as described above based on the ratio of isothermally non-recoverable strain to the strain length of the load plateau. FIG. 20 illustrates the positive correlation between isothermally non-recoverable strain and conditioning load. Non-recoverable strain was less than 0.17% for all samples conditioned below 1400 MPa resulting in a max. volume of retained martensite estimate of 3.7% for the same samples loaded below 1400 MPa.

In this Example, it has been demonstrated that mechanical conditioning of superelastic NiTi wire results in improved fatigue performance, while maintaining good mechanical properties. In addition, less than 3.7% of the matrix was left in the martensite phase after load removal for conditioning below 1400 MPa with a concomitant maximum isothermally non-recoverable strain of 0.17%. Further, an increase in the strain fatigue life of greater than 3000% at $10^6$ cycles is observed in wire conditioned at 1240 MPa versus non-conditioned wire while maintaining good elastic properties suitable for said medical device applications.

Example 4

Mechanical Conditioning of Superelastic NiTi Wire for Improved Fatigue Resistance In this Example, the effects of mechanical overload conditioning of superelastic wire and the possibility of increased fatigue damage resistance associated with near-defect, plasticity-locked phase transformation were further investigated over a broader range of loads as compared to Example 2 using a high strength chromium doped tertiary Nitinol compound.

1. Experimental Technique

Figure 19B:
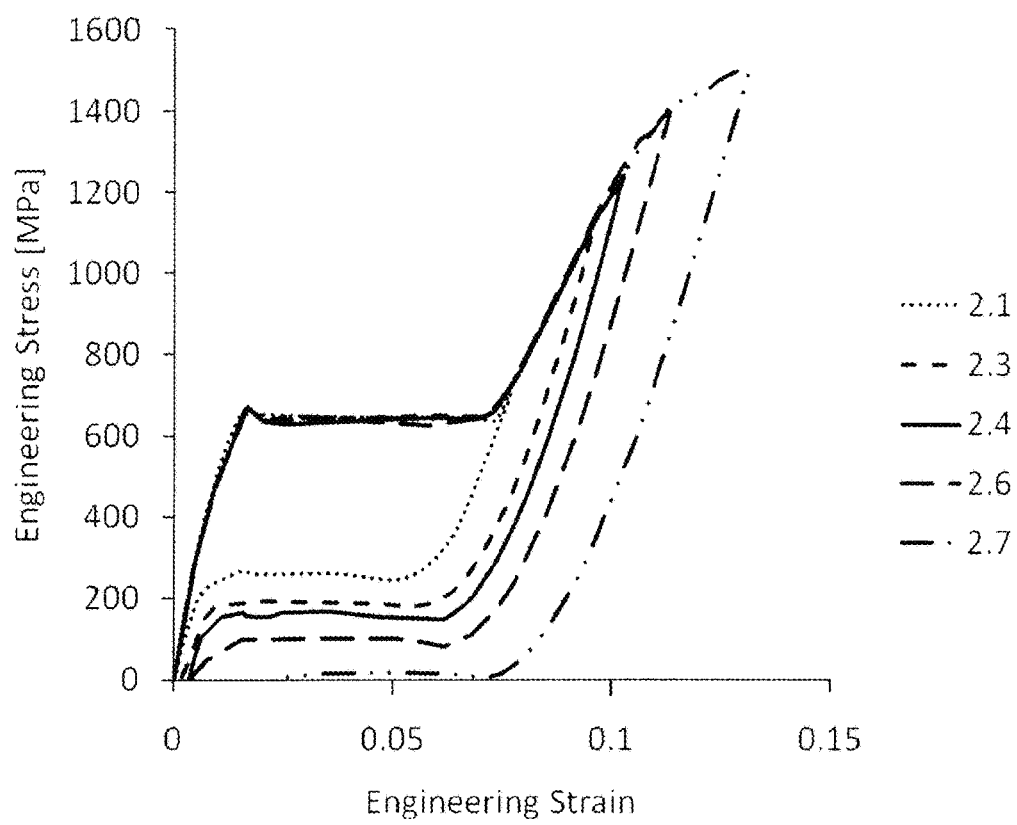
FIG. 19(b) is a stress-strain curve for five wire samples, where each wire sample was loaded using the conditioning regime indicated by the legend at the right of the figure and described in Table 2.

Samples for this Example were subjected to a total engineering strain departure, measured by crosshead extension, ranging from about 7.7% to 13.1% Conditioning was applied by approaching the martensitic yield point at 295 K using strain-rate-controlled loading in order induce some dislocation locking of stress-transformed material in the vicinity of stress concentrators. Referring now to FIG. 19(b), the conditioning cycle comprises a strain-controlled ramp to five stress levels of 0, 700, 1100, 1240, 1400, and 1500 MPa engineering stress, resulting in an engineering strain of about 0%, 7.7%, 9.6%, 10.2%, 11.3%, and 13.1% respectively, followed by a 3 second hold, finishing with a strain-controlled ramp to zero load.

In order to prepare samples for this Example, Nitinol wire with an ingot austenite start temperature, As, of about 235 K, having Ti-55.8 wt. % Ni-0.25 wt % Cr was repetitively drawn and annealed from a diameter of 2 mm to a diameter of 361 µm in accordance with the process described above. At this stage, wires were continuously annealed at 950 to 1000 K. Final cold working was completed using diamond dies to draw round wire with a diameter of 269 µm prior to continuous, reel-to-reel annealing at 750 to 780 K under constant engineering stress for 40 to 80 seconds to effect linear shape setting. The final wire comprised a room-temperature-superelastic Nitinol wire with an active austenitic finish temperature, Af, of 283 K and an approximately 120 nm thick, dark brown oxide layer similar to that disclosed in an article by the present inventor entitled "Structure-Property Relationships in Conventional and Nanocrystalline NiTi Intermetallic Alloy Wire" and published in the *Journal of Materials Engineering and Performance*, February 2008, ISSN 1544-1024, pgs. 1-6, which is incorporated by reference above.

Cyclic and monotonic uniaxial tensile properties were measured at an ambient temperature of 295 K at a strain rate of $10^{-3}$ s$^{-1}$ using an Instron Model 5565 Tensile Test Bench equipped with pneumatic, smooth face grips. Six hundred grit emery-cloth was used to reduce grip-specimen interface slip.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency.

As shown in FIGS. 18(a) to (d), three specimens from each group at each conditioning cycle, ranging from 0 MPa which indicates non-conditioned wire to 1500 MPa which indicates the maximum conditioning load used, were tested at alternating engineering strain (½ peak-to-peak amplitude) levels ranging from 0.80 to 1.25% strain to a maximum of about 10$^6$ cycles. The total samples tested for each conditioning load regime for each sample was 12 resulting in a total of 72 fatigue samples tested for this portion of the study. Samples which did not fracture after 10$^6$ cycles were stopped and recorded.

2. Results

The resulting tensile data is shown graphically in FIG. 19(b). As noted above, the conditioning cycle comprised a strain-controlled ramp to a stress level of 0, 700, 1100, 1240, 1400 or 1500 MPa engineering stress, as indicated along the horizontal axis of the plot, followed by a 3 second hold, finishing with a strain-controlled ramp to zero load. This conditioning cycle generated data curves 2.1, 2.3, 2.4, 2.6 and 2.7 shown in FIG. 19(b). The total engineering strain departure for respective cycles, measured by crosshead extension, was about 0%, 7.7%, 9.6%, 10.2%, 11.3%, and 13.1% for increasing load levels respectively. Conditioning resulted in residual strains (i.e. isothermally non-recoverable strains) of respectively 0%, 0.07%, 0.09%, 0.35%, 0.18%, and 2.23% respectively.

FIGS. 18(a)-(d) illustrate the observed differences in fatigue performance for non-conditioned (e.g. 0 load level on x-axis) and conditioned wire specimens (700, 1100, 1240, 1400, and 1500 MPa on the x-axis) The conditioning resulted in an upward cycle life shift of at least 46% and 2500% at the 1.25% and 0.95% alternating strain test levels respectively at a conditioning load level of 1240 MPa. An overall upward trend in lifetime for a given test strain level was observed for increasing conditioning load through 1500 MPa. Most samples of the material conditioned at greater than 1240 MPa survived more than 10$^6$ cycles and were still running at the time of conclusion of the experiment for test strain levels below 0.95%.

FIG. 19(b) illustrates the observed tensile behavior during load conditioning of each sample. In each case, an upper bound of the maximum volume of retained martensite was calculated as described above based on the ratio of isothermally non-recoverable strain to the strain length of the load plateau. FIG. 20 illustrates the positive correlation between isothermally non-recoverable strain and conditioning load. Non-recoverable strain was less than 0.35% for all samples conditioned below 1400 MPa resulting in a max volume of retained martensite estimate of 5.9% for the same samples loaded below 1400 MPa.

In this Example, it has been demonstrated that mechanical conditioning of superelastic NiTi wire results in improved fatigue performance, while maintaining good mechanical properties. In addition, less than 5.9% of the matrix was left in the martensite phase after load removal for conditioning below 1400 MPa with a concomitant maximum isothermally non-recoverable strain of 0.35%. Further, an increase in the strain fatigue life of greater than 2500% at 10$^6$ cycles is observed in wire conditioned at 1240 MPa versus non-conditioned wire while maintaining good elastic properties suitable for said medical device applications.

Example 5

Mechanical Conditioning of Superelastic NiTi Wire for Improved Fatigue Resistance In this Example, the effects of mechanical overload conditioning of superelastic wire and the possibility of increased fatigue damage resistance associated with near-defect, plasticity-locked phase transformation were further investigated over a broader range of loads as compared to Example 2 using a Nitinol with warmer transformation temperatures as compared to Examples 2 and 3.

1. Experimental Technique

Figure 19C:
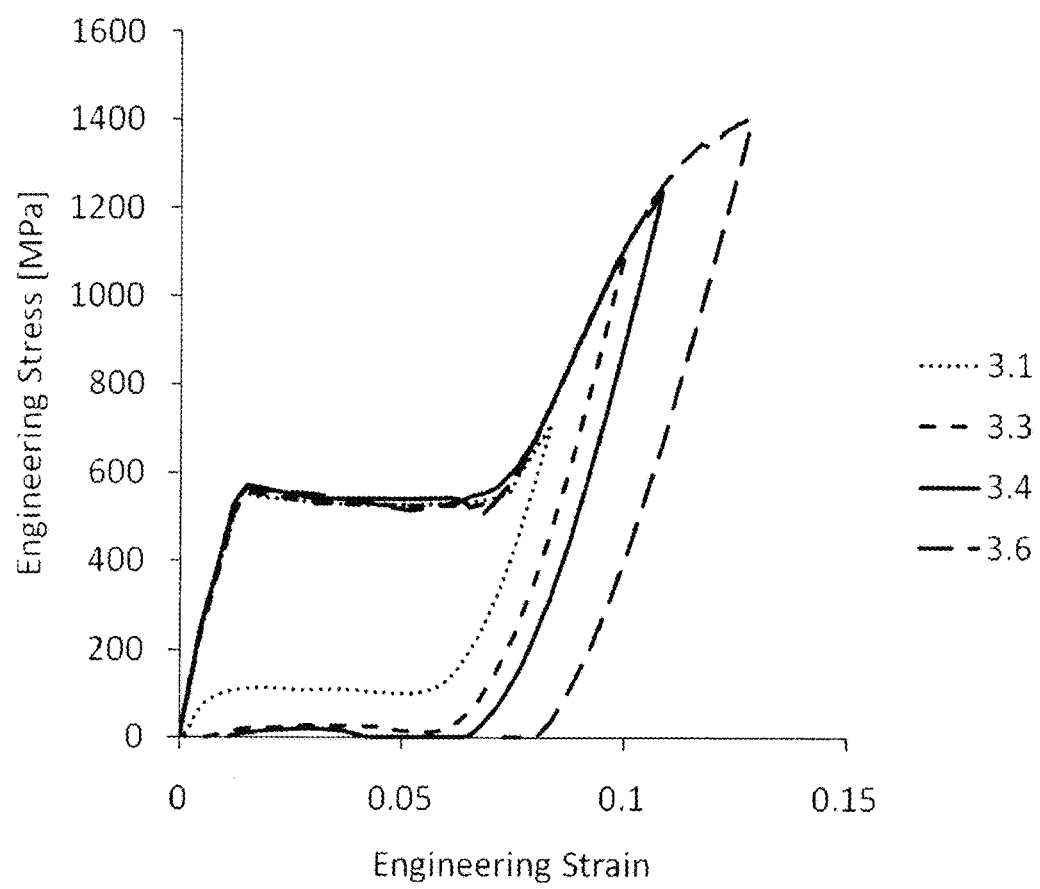
FIG. 19(c) is a stress-strain curve for five wire samples, where each wire sample was loaded using the conditioning regime indicated by the legend at the right of the figure and described in Table 2.

Samples for this Example were subjected to a total engineering strain departure, measured by crosshead extension, ranging from about 8.3% to 12.8% Conditioning was applied by approaching the martensitic yield point at 295 K using strain-rate-controlled loading in order induce some dislocation locking of stress-transformed material in the vicinity of stress concentrators. Referring now to FIG. 19(c), the conditioning cycle comprises a strain-controlled ramp to five stress levels of 0, 700, 1100, 1240, and 1400 MPa engineering stress, resulting in an engineering strain of about 0%, 8.3%, 10%, 10.8%, and 12.8% respectively, followed by a 3 second hold, finishing with a strain-controlled ramp to zero load.

In order to prepare samples for this Example, Nitinol wire with an ingot austenite start temperature, $A_s$, of about 255 K, having Ti-55.8 wt. % Ni was repetitively drawn and annealed from a diameter of 2 mm to a diameter of 380 μm in accordance with the process described above. At this stage, wires were continuously annealed at 950 to 1000 K. Final cold working was completed using diamond dies to draw round wire with a diameter of 302 μm prior to continuous, reel-to-reel annealing at 750 to 780 K under constant engineering stress for 40 to 80 seconds to effect linear shape setting. The final wire comprised a room-temperature-superelastic Nitinol wire with an active austenitic finish temperature, $A_f$, of 298 K and an approximately 120 nm thick, dark brown oxide layer similar to that disclosed in an article by the present inventor entitled "Structure-Property Relationships in Conventional and Nanocrystalline NiTi Intermetallic Alloy Wire" and published in the *Journal of Materials Engineering and Performance*, February 2008, ISSN 1544-1024, pgs. 1-6, which is incorporated by reference above.

Cyclic and monotonic uniaxial tensile properties were measured at an ambient temperature of 295 K at a strain rate of 10$^{-3}$ s$^{-1}$ using an Instron Model 5565 Tensile Test Bench equipped with pneumatic, smooth face grips. Six hundred grit emery-cloth was used to reduce grip-specimen interface slip.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency.

As shown in FIGS. 18(a) to (d), three specimens from each group at each conditioning cycle, ranging from 0 MPa which indicates non-conditioned wire to 1400 MPa which indicates the maximum conditioning load used, were tested at alternating engineering strain (½ peak-to-peak amplitude) levels ranging from 0.80 to 1.25% strain to a maximum of about 10$^6$ cycles. The total samples tested for each conditioning load regime for each sample was 12 resulting in a total of 60 fatigue samples tested for this portion of the study. Samples which did not fracture after $10^6$ cycles were stopped and recorded.

2. Results

The resulting tensile data is shown graphically in FIG. 19(c). As noted above, the conditioning cycle comprised a strain-controlled ramp to a stress level of 0, 700, 1100, 1240, or 1400 MPa engineering stress, as indicated along the horizontal axis of the plot, followed by a 3 second hold, finishing with a strain-controlled ramp to zero load. This conditioning cycle generated curves 3.1, 3.3, 3.4, and 3.6 shown in FIG. 19(c). The total engineering strain departure for respective cycles, measured by crosshead extension, was about 0%, 8.3%, 10%, 10.8%, and 12.8% for increasing load levels respectively. Conditioning resulted in residual strains (i.e. isothermally non-recoverable strains) of respectively 0%, 0.03%, 0.13%, 1.1%, and 7.31% respectively.

FIGS. 18(a) to (d) illustrate the observed differences in fatigue performance for non-conditioned (e.g. 0 load level on x-axis) and conditioned wire specimens (700, 1100, 1240, and 1400 MPa on the x-axis) The conditioning resulted in an upward cycle life shift of at least 116% and 2400% at the 1.25% and 0.95% alternating strain test levels respectively at a conditioning load level of 1240 MPa. An overall upward trend in lifetime for a given test strain level was observed for increasing conditioning load through 1400 MPa. Most samples of the material conditioned at greater than 1240 MPa survived more than $10^6$ cycles and were still running at the time of conclusion of the experiment for test strain levels below 0.95%.

FIG. 19(c) illustrates the observed tensile behavior during load conditioning of each sample. In each case, an upper bound of the maximum volume of retained martensite was calculated as described above based on the ratio of isothermally non-recoverable strain to the strain length of the load plateau. FIG. 20 illustrates the positive correlation between isothermally non-recoverable strain and conditioning load. Non-recoverable strain was less than about 1% for all samples conditioned below 1240 MPa resulting in a max. volume of retained martensite estimate of about 17% for the same samples loaded below 1240 MPa.

In this Example, it has been demonstrated that mechanical conditioning of superelastic NiTi wire results in improved fatigue performance, while maintaining good mechanical properties. In addition, less than about 17% of the matrix was left in the martensite phase after load removal for conditioning below 1240 MPa with a concomitant maximum isothermally non-recoverable strain of about 1%. Further, an increase in the strain fatigue life of greater than 2400% at $10^6$ cycles is observed in wire conditioned at 1240 MPa versus non-conditioned wire while maintaining good elastic properties suitable for said medical device applications.

Example 6

Mechanical Conditioning of Superelastic NiTi Wire with an Etched Surface Finish for Improved Fatigue Resistance In this Example, the effects of mechanical overload conditioning of superelastic wire and the possibility of increased fatigue damage resistance associated with near-defect, plasticity-locked phase transformation were further investigated over a broader range of loads as compared to Example 2 and in a finer diameter using a Nitinol with an etched surface finish comprising a substantially oxide-free surface.

1. Experimental Technique

Samples for this Example were subjected to a total engineering strain departure, measured by crosshead extension, ranging from about 7.8 to 11.9% Conditioning was applied by approaching the martensitic yield point at 295 K using strain-rate-controlled loading in order induce some dislocation locking of stress-transformed material in the vicinity of stress concentrators. Referring now to FIG. 19(d), the conditioning cycle comprises a strain-controlled ramp to five stress levels of 0, 700, 1100, 1240, 1400 and 1500 MPa engineering stress, resulting in an engineering strain of about 0%, 7.8%, 9.5%, 10%, 10.8%, and 11.9% respectively, followed by a 3 second hold, finishing with a strain-controlled ramp to zero load.

In order to prepare samples for this Example, Nitinol wire with an ingot austenite start temperature, $A_s$, of about 246 K, having Ti-56 wt. % Ni was repetitively drawn and annealed from a diameter of 2 mm to a diameter of 102 μm in accordance with the process described above. At this stage, wires were continuously annealed at 950 to 1000 K. Final cold working was completed using diamond dies to draw round wire with a diameter of 76 μm prior to continuous, reel-to-reel annealing at 750 to 780 K under constant engineering stress for 40 to 80 seconds to effect linear shape setting. The final wire comprised a room-temperature-superelastic Nitinol wire with an active austenitic finish temperature, $A_f$, of 288 K and an etched, substantially oxide-free surface finish.

Cyclic and monotonic uniaxial tensile properties were measured at an ambient temperature of 295 K at a strain rate of $10^{-3}$ s$^{-1}$ using an Instron Model 5565 Tensile Test Bench equipped with pneumatic, smooth face grips. Six hundred grit emery-cloth was used to reduce grip-specimen interface slip.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency.

As shown in FIGS. 18(a) to (d), three specimens from each group at each conditioning cycle, ranging from 0 MPa which indicates non-conditioned wire to 1500 MPa which indicates the maximum conditioning load used, were tested at alternating engineering strain (½ peak-to-peak amplitude) levels ranging from 0.80 to 1.25% strain to a maximum of about $10^6$ cycles. The total samples tested for each conditioning load regime for each sample was 12 resulting in a total of 72 fatigue samples tested for this portion of the study. Samples which did not fracture after $10^6$ cycles were stopped and recorded.

2. Results

The resulting tensile data is shown graphically in FIG. 19(d). As noted above, the conditioning cycle comprised a strain-controlled ramp to a stress level of 0, 700, 1100, 1240, 1400 or 1500 MPa engineering stress, as indicated along the horizontal axis of the plot, followed by a 3 second hold, finishing with a strain-controlled ramp to zero load. This conditioning cycle generated curves 4.1, 4.3, 4.4, 4.6 and 4.7 shown in FIG. 19(d). The total engineering strain departure for respective cycles, measured by crosshead extension, was about 0%, 7.8%, 9.5%, 10%, 10.8%, and 11.9% for increasing load levels respectively. Conditioning resulted in residual strains (i.e. isothermally non-recoverable strains) of respectively 0%, 0.09%, 0.14%, 0.29%, 0.26% and 7.2% respectively.

FIGS. 18(a) to (d) illustrate the observed differences in fatigue performance for non-conditioned (e.g. 0 load level on x-axis) and conditioned wire specimens (700, 1100, 1240, 1400 and 1500 MPa on the x-axis) The conditioning resulted in an upward cycle life shift of at least 7.2% and 2600% at the 1.25% and 0.95% alternating strain test levels respectively at a conditioning load level of 1240 MPa. An overall upward trend in lifetime for a given test strain level was observed for increasing conditioning load through 1500 MPa. Most samples of the material conditioned at greater than 1240 MPa survived more than $10^6$ cycles and were still running at the time of conclusion of the experiment for test strain levels below 0.95%.

FIG. 19(d) illustrates the observed tensile behavior during load conditioning of each sample. In each case, an upper bound of the maximum volume of retained martensite was calculated as described above based on the ratio of isothermally non-recoverable strain to the strain length of the load plateau. FIG. 20 illustrates the positive correlation between isothermally non-recoverable strain and conditioning load. Non-recoverable strain was less than about 0.29% for all samples conditioned below 1240 MPa resulting in a max. volume of retained martensite estimate of about 4.7% for the same samples loaded below 1400 MPa.

In this Example, it has been demonstrated that mechanical conditioning of superelastic NiTi wire results in improved fatigue performance, while maintaining good mechanical properties. In addition, less than about 4.7% of the matrix was left in the martensite phase after load removal for conditioning below 1400 MPa with a concomitant maximum isothermally non-recoverable strain of about 0.29%. Further, an increase in the strain fatigue life of greater than 2600% at $10^6$ cycles is observed in wire conditioned at 1240 MPa versus non-conditioned wire while maintaining good elastic properties suitable for said medical device applications.

Example 7

Mechanical Conditioning of Superelastic NiTi Wire with a Polished Surface Finish for Improved Fatigue Resistance In this Example, the effects of mechanical overload conditioning of superelastic wire and the possibility of increased fatigue damage resistance associated with near-defect, plasticity-locked phase transformation were further investigated over a broader range of loads as compared to Example 2 and in a larger diameter using a Nitinol with an etched and mechanically polished surface finish comprising a substantially oxide-free surface.

1. Experimental Technique

Samples for this Example were subjected to a total engineering strain departure, measured by crosshead extension, ranging from about 7.5 to 13.1% Conditioning was applied by approaching the martensitic yield point at 295 K using strain-rate-controlled loading in order induce some dislocation locking of stress-transformed material in the vicinity of stress concentrators. Referring now to FIG. 19(d), the conditioning cycle comprises a strain-controlled ramp to five stress levels of 0, 700, 1100, 1240, 1400 and 1500 MPa engineering stress, resulting in an engineering strain of about 0%, 7.5%, 9.6%, 10.3%, 11.6%, and 13.1% respectively, followed by a 3 second hold, finishing with a strain-controlled ramp to zero load.

In order to prepare samples for this Example, Nitinol wire with an ingot austenite start temperature, $A_s$, of about 249 K, having Ti-56 wt. % Ni was repetitively drawn and annealed from a diameter of 2 mm to a diameter of 813 μm in accordance with the process described above. At this stage, wires were continuously annealed at 950 to 1000 K. Final cold working was completed using diamond dies to draw round wire with a diameter of 638 μm prior to continuous, reel-to-reel annealing at 750 to 780 K under constant engineering stress for 60 to 150 seconds to effect linear shape setting. The final wire comprised a room-temperature-superelastic Nitinol wire with an active austenitic finish temperature, $A_f$, of 291 K and an etched, substantially oxide-free and mechanically polished surface finish.

Cyclic and monotonic uniaxial tensile properties were measured at an ambient temperature of 295 K at a strain rate of $10^{-3}$ s$^{-1}$ using an Instron Model 5565 Tensile Test Bench equipped with pneumatic, smooth face grips. Six hundred grit emery-cloth was used to reduce grip-specimen interface slip.

Fatigue behavior was characterized using rotary beam fatigue test equipment manufactured by Positool, Inc., at a test rate of 60 s$^{-1}$ in ambient 298 K air. The test rate was chosen at a rate significantly higher than physiological loading frequencies to promote expediency.

As shown in FIGS. 18(a) to (d), three specimens from each group at each conditioning cycle, ranging from 0 MPa which indicates non-conditioned wire to 1500 MPa which indicates the maximum conditioning load used, were tested at alternating engineering strain (½ peak-to-peak amplitude) levels ranging from 0.80 to 1.25% strain to a maximum of about $10^6$ cycles. The total samples tested for each conditioning load regime for each sample was 12 resulting in a total of 72 fatigue samples tested for this portion of the study. Samples which did not fracture after $10^6$ cycles were stopped and recorded.

2. Results

Figure 19E:
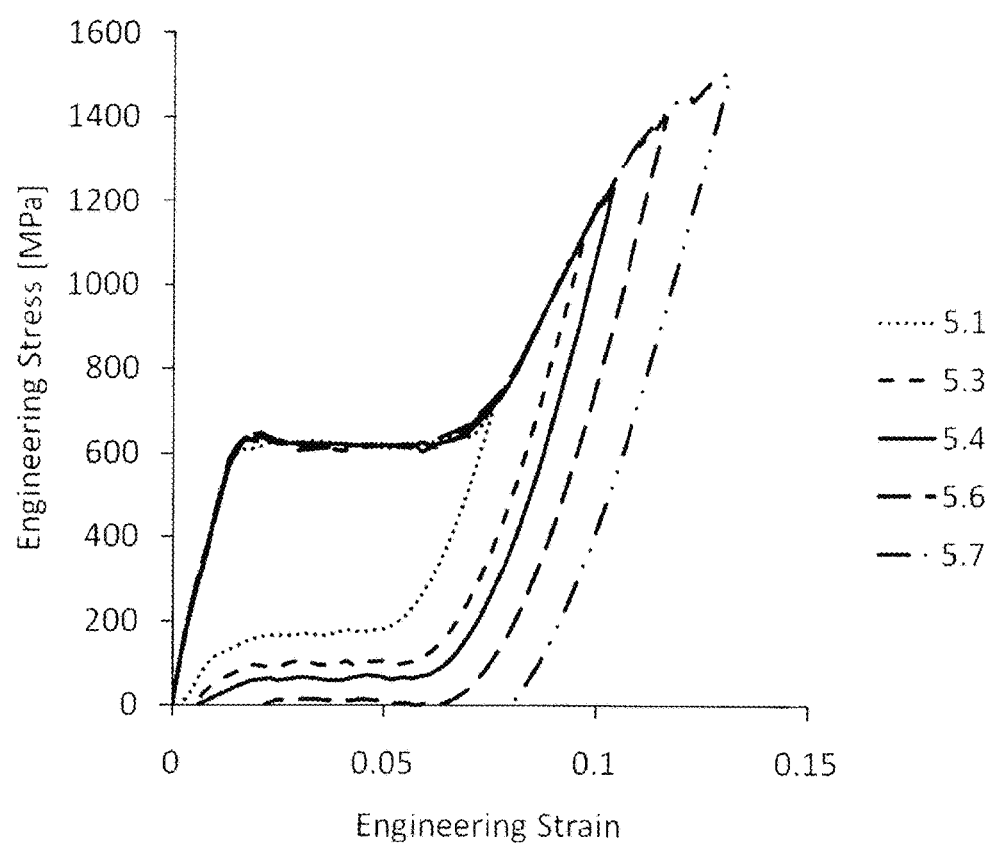
FIG. 19(e) is a stress-strain curve for five wire samples, where each wire sample was loaded using the conditioning regime indicated by the legend at the right of the figure and described in Table 2.

The resulting tensile data is shown graphically in FIG. 19(e). As noted above, the conditioning cycle comprised a strain-controlled ramp to a stress level of 0, 700, 1100, 1240, 1400 or 1500 MPa engineering stress, as indicated along the horizontal axis of the plot, followed by a 3 second hold, finishing with a strain-controlled ramp to zero load. This conditioning cycle generated data curves 5.1, 5.3, 5.4, 5.6 and 5.7 shown in FIG. 19(e). The total engineering strain departure for respective cycles, measured by crosshead extension, was about 0%, 7.5%, 9.6%, 10.3%, 11.6%, and 13.1% for increasing load levels respectively. Conditioning resulted in residual strains (i.e. isothermally non-recoverable strains) of respectively 0%, 0.21%, 0.40%, 0.61%, 2.17%, and 7.84% respectively.

FIGS. 18(a) to (d) illustrate the observed differences in fatigue performance for non-conditioned (e.g. 0 load level on x-axis) and conditioned wire specimens (700, 1100, 1240, 1400 and 1500 MPa on the x-axis) The conditioning resulted in an upward cycle life shift of at least 54% at the 0.95% alternating strain test levels respectively at a conditioning load level of 1240 MPa. An overall upward trend in lifetime for a given test strain level was observed for increasing conditioning load through 1500 MPa. Most samples of the material conditioned at greater than 1240 MPa survived more than $10^6$ cycles and were still running at the time of conclusion of the experiment for test strain levels below 0.80%.

FIG. 19(e) illustrates the observed tensile behavior during load conditioning of each sample. In each case, an upper bound of the maximum volume of retained martensite was calculated as described above based on the ratio of isothermally non-recoverable strain to the strain length of the load plateau. FIG. 20 illustrates the positive correlation between isothermally non-recoverable strain and conditioning load. Non-recoverable strain was less than about 0.61% for all samples conditioned below 1240 MPa resulting in a max. volume of retained martensite estimate of about 11% for the same samples loaded below 1240 MPa.

In this Example, it has been demonstrated that mechanical conditioning of superelastic NiTi wire results in improved fatigue performance, while maintaining good mechanical properties. In addition, less than about 11% of the matrix was left in the martensite phase after load removal for conditioning below 1240 MPa with a concomitant maximum isothermally non-recoverable strain of about 0.61%. Further, an increase in the strain fatigue life of greater than 54% at $10^6$ cycles is observed in wire conditioned at 1240 MPa versus non-conditioned wire while maintaining good elastic properties suitable for said medical device applications.

TABLE 3

Tensile Data for Various Wire Samples, see Examples 3-6, FIG. 19(a)

| | | | | | Strain level | | | | | |
|---|---|---|---|---|---|---|---|---|---|---|
| | 1.1 Engr. Strain | Engr. Stress (MPa) | 1.3 Engr. Strain | Engr. Stress (MPa) | 1.4 Engr. Strain | Engr. Stress (MPa) | 1.6 Engr. Strain | Engr. Stress (MPa) | 1.7 Engr. Strain | Engr. Stress (MPa) |
| | 0 | 0 | 0 | 0 | 0 | 0 | 0 | 0 | 0 | 0 |
| | 0.0019 | 106.7 | 0.0020 | 108.5 | 0.0009 | 51.2 | 0.0016 | 86.8 | 0.0010 | 55.8 |
| | 0.0154 | 655.3 | 0.0132 | 601.7 | 0.0047 | 295.3 | 0.0053 | 315.4 | 0.0048 | 287.4 |
| | 0.0157 | 614.5 | 0.0163 | 680.2 | 0.0134 | 626.4 | 0.0085 | 431.0 | 0.0096 | 461.7 |
| | 0.0201 | 644.5 | 0.0180 | 591.1 | 0.0170 | 686.4 | 0.0139 | 630.5 | 0.0135 | 614.8 |
| | 0.0523 | 643.1 | 0.0195 | 635.8 | 0.0209 | 612.7 | 0.0189 | 642.5 | 0.0160 | 663.5 |
| | 0.0796 | 639.8 | 0.0513 | 636.2 | 0.0305 | 636.1 | 0.0462 | 657.7 | 0.0393 | 621.6 |
| | 0.0817 | 699.7 | 0.0747 | 638.4 | 0.0701 | 634.9 | 0.0612 | 631.2 | 0.0579 | 624.2 |
| | 0.0821 | 716.8 | 0.0784 | 635.4 | 0.0753 | 643.3 | 0.0766 | 642.1 | 0.0787 | 631.7 |
| | 0.0826 | 700.5 | 0.0797 | 669.7 | 0.0793 | 690.4 | 0.0793 | 665.2 | 0.0804 | 680.6 |
| | 0.0746 | 431.8 | 0.0822 | 739.3 | 0.0826 | 755.0 | 0.0824 | 748.1 | 0.0856 | 809.0 |
| | 0.0718 | 360.0 | 0.0899 | 933.9 | 0.0866 | 854.4 | 0.0872 | 870.6 | 0.0948 | 1036.8 |
| | 0.0688 | 293.9 | 0.0968 | 1100.3 | 0.1006 | 1189.9 | 0.0953 | 1082.6 | 0.1083 | 1341.4 |
| | 0.0646 | 222.5 | 0.0974 | 1116.1 | 0.1012 | 1201.9 | 0.1075 | 1351.4 | 0.1209 | 1500.8 |
| | 0.0633 | 206.7 | 0.0976 | 1114.3 | 0.1019 | 1218.4 | 0.1082 | 1353.9 | 0.1223 | 1508.2 |
| | 0.0618 | 190.8 | 0.0969 | 1092.6 | 0.1026 | 1234.8 | 0.1105 | 1400.7 | 0.1202 | 1427.7 |
| | 0.0593 | 171.7 | 0.0921 | 891.0 | 0.1030 | 1245.6 | 0.1113 | 1406.2 | 0.1184 | 1353.7 |
| | 0.0558 | 160.0 | 0.0801 | 460.0 | 0.1033 | 1243.3 | 0.1084 | 1286.7 | 0.1096 | 1012.9 |
| | 0.0526 | 168.1 | 0.0774 | 381.8 | 0.1012 | 1157.5 | 0.1069 | 1225.5 | 0.0940 | 463.0 |
| | 0.0461 | 160.4 | 0.0742 | 303.2 | 0.0985 | 1043.9 | 0.1007 | 970.9 | 0.0798 | 100.3 |
| | 0.0393 | 178.4 | 0.0705 | 225.0 | 0.0887 | 662.5 | 0.0788 | 240.8 | 0.0734 | 4.9 |
| | 0.0288 | 170.2 | 0.0667 | 165.6 | 0.0791 | 358.0 | 0.0725 | 116.4 | 0.0729 | 0.1 |
| | 0.0233 | 169.8 | 0.0615 | 113.5 | 0.0745 | 246.1 | 0.0640 | 33.1 | 0.0727 | 0.0 |
| | 0.0113 | 167.4 | 0.0584 | 106.0 | 0.0691 | 149.6 | 0.0590 | 39.1 | | |
| | 0.0063 | 169.4 | 0.0540 | 111.2 | 0.0651 | 103.4 | 0.0511 | 33.0 | | |
| | 0.0019 | 0.0 | 0.0426 | 113.7 | 0.0585 | 84.8 | 0.0440 | 35.5 | | |
| | | | 0.0309 | 112.0 | 0.0520 | 91.9 | 0.0352 | 38.7 | | |
| | | | 0.0074 | 113.2 | 0.0435 | 93.6 | 0.0265 | 35.2 | | |
| | | | 0.0044 | 92.9 | 0.0335 | 95.8 | 0.0152 | 67.2 | | |
| | | | 0.0030 | 53.3 | 0.0262 | 93.2 | 0.0115 | 56.6 | | |
| | | | 0.0020 | 0.0 | 0.0174 | 81.9 | 0.0048 | 25.7 | | |
| | | | | | 0.0122 | 99.3 | 0.0017 | 0.0 | | |
| | | | | | 0.0089 | 111.8 | | | | |
| | | | | | 0.0062 | 76.2 | | | | |
| | | | | | 0.0029 | 17.0 | | | | |
| | | | | | 0.0024 | 0.0 | | | | |
| load plateau length (strain) → | 0.0663 | | 0.0690 | | 0.0658 | | 0.0654 | | 0.0652 | |
| unload plateau length (strain) → | 0.0627 | | 0.0648 | | 0.0627 | | 0.0623 | | 0.0071 | |
| permanent set (strain) → | 0.0019 | | 0.0020 | | 0.0024 | | 0.0017 | | 0.0727 | |
| max volume fraction martensite (%) → | 2.9% | | 2.8% | | 3.7% | | 2.6% | | 100.0% | |

TABLE 4

Tensile Data for Various Wire Samples, see Examples 3-6, FIG. 19(b)

| | | | Strain level | | | | | | |
|---|---|---|---|---|---|---|---|---|---|
| 2.1 Engr. Strain | Engr. Stress (MPa) | 2.3 Engr. Strain | Engr. Stress (MPa) | 2.4 Engr. Strain | Engr. Stress (MPa) | 2.6 Engr. Strain | Engr. Stress (MPa) | 2.7 Engr. Strain | Engr. Stress (MPa) |
| 0 | 0 | 0 | 0 | 0 | 0 | 0 | 0 | 0 | 0 |
| 0.0052 | 313.2 | 0.0009 | 49.5 | 0.0009 | 51.0 | 0.0007 | 37.9 | 0.0008 | 44.9 |
| 0.0107 | 540.7 | 0.0047 | 278.5 | 0.0047 | 277.4 | 0.0044 | 268.7 | 0.0046 | 274.8 |

TABLE 4-continued

Tensile Data for Various Wire Samples, see Examples 3-6, FIG. 19(b)

| | 2.1 Engr. Strain | Engr. Stress (MPa) | 2.3 Engr. Strain | Engr. Stress (MPa) | 2.4 Engr. Strain | Engr. Stress (MPa) | 2.6 Engr. Strain | Engr. Stress (MPa) | 2.7 Engr. Strain | Engr. Stress (MPa) |
|---|---|---|---|---|---|---|---|---|---|---|
| | 0.0148 | 647.1 | 0.0092 | 470.9 | 0.0093 | 470.0 | 0.0090 | 464.1 | 0.0092 | 469.4 |
| | 0.0152 | 645.2 | 0.0165 | 668.0 | 0.0166 | 668.5 | 0.0163 | 671.1 | 0.0164 | 670.8 |
| | 0.0159 | 650.8 | 0.0205 | 641.1 | 0.0205 | 634.1 | 0.0203 | 632.2 | 0.0204 | 638.9 |
| | 0.0164 | 654.0 | 0.0253 | 640.1 | 0.0253 | 627.5 | 0.0251 | 647.9 | 0.0252 | 647.7 |
| | 0.0170 | 657.3 | 0.0584 | 649.5 | 0.0584 | 644.5 | 0.0582 | 624.2 | 0.0583 | 641.6 |
| | 0.0245 | 650.4 | 0.0694 | 646.7 | 0.0695 | 641.9 | 0.0692 | 642.2 | 0.0694 | 644.0 |
| | 0.0684 | 641.0 | 0.0728 | 655.8 | 0.0728 | 658.1 | 0.0726 | 666.4 | 0.0727 | 656.6 |
| | 0.0734 | 637.0 | 0.0757 | 702.2 | 0.0757 | 701.7 | 0.0755 | 701.9 | 0.0756 | 701.7 |
| | 0.0743 | 652.5 | 0.0782 | 749.1 | 0.0782 | 743.7 | 0.0780 | 747.0 | 0.0781 | 746.1 |
| | 0.0749 | 666.0 | 0.0901 | 1006.6 | 0.0901 | 1000.8 | 0.0899 | 1007.8 | 0.0900 | 999.6 |
| | 0.0763 | 697.5 | 0.0928 | 1059.7 | 0.0941 | 1088.6 | 0.0938 | 1097.3 | 0.0939 | 1084.7 |
| | 0.0767 | 706.1 | 0.0932 | 1061.0 | 0.0970 | 1149.8 | 0.0967 | 1159.7 | 0.0969 | 1145.1 |
| | 0.0767 | 696.1 | 0.0936 | 1070.4 | 0.0992 | 1189.1 | 0.1003 | 1230.4 | 0.1004 | 1213.8 |
| | 0.0653 | 386.6 | 0.0944 | 1087.2 | 0.1000 | 1195.9 | 0.1059 | 1326.9 | 0.1060 | 1310.6 |
| | 0.0603 | 304.9 | 0.0951 | 1103.2 | 0.1007 | 1210.8 | 0.1084 | 1345.7 | 0.1114 | 1384.3 |
| | 0.0553 | 260.5 | 0.0955 | 1109.7 | 0.1014 | 1226.5 | 0.1091 | 1352.0 | 0.1169 | 1440.2 |
| | 0.0506 | 244.2 | 0.0955 | 1104.3 | 0.1021 | 1239.8 | 0.1099 | 1363.8 | 0.1199 | 1442.0 |
| | 0.0446 | 249.3 | 0.0953 | 1098.4 | 0.1022 | 1240.6 | 0.1102 | 1369.1 | 0.1202 | 1438.8 |
| | 0.0361 | 260.2 | 0.0919 | 961.0 | 0.1022 | 1236.0 | 0.1106 | 1377.1 | 0.1219 | 1454.3 |
| | 0.0183 | 258.0 | 0.0877 | 800.9 | 0.1022 | 1231.9 | 0.1112 | 1385.9 | 0.1239 | 1475.3 |
| | 0.0158 | 267.6 | 0.0867 | 762.9 | 0.1016 | 1210.2 | 0.1113 | 1388.1 | 0.1260 | 1488.8 |
| | 0.0086 | 232.7 | 0.0827 | 626.9 | 0.0976 | 1045.7 | 0.1118 | 1396.0 | 0.1279 | 1497.3 |
| | 0.0071 | 218.2 | 0.0792 | 518.0 | 0.0941 | 905.5 | 0.1123 | 1401.5 | 0.1309 | 1499.0 |
| | 0.0053 | 192.6 | 0.0759 | 428.1 | 0.0908 | 780.5 | 0.1128 | 1399.3 | 0.1287 | 1417.2 |
| | 0.0028 | 113.0 | 0.0707 | 313.8 | 0.0856 | 601.6 | 0.1129 | 1397.9 | 0.1252 | 1281.9 |
| | 0.0008 | 22.5 | 0.0671 | 255.5 | 0.0820 | 493.4 | 0.1106 | 1307.1 | 0.1162 | 952.8 |
| | 0.0007 | 0.0 | 0.0634 | 210.8 | 0.0783 | 393.2 | 0.1087 | 1230.3 | 0.1114 | 787.8 |
| | | | 0.0588 | 185.1 | 0.0737 | 291.6 | 0.1041 | 1047.3 | 0.1060 | 614.2 |
| | | | 0.0540 | 179.0 | 0.0689 | 212.5 | 0.0993 | 864.9 | 0.0943 | 298.8 |
| | | | 0.0517 | 180.0 | 0.0666 | 184.7 | 0.0970 | 781.4 | 0.0908 | 222.1 |
| | | | 0.0469 | 186.4 | 0.0618 | 148.3 | 0.0922 | 617.6 | 0.0864 | 141.9 |
| | | | 0.0323 | 190.5 | 0.0472 | 152.9 | 0.0851 | 407.8 | 0.0820 | 78.7 |
| | | | 0.0205 | 191.7 | 0.0354 | 166.8 | 0.0777 | 237.4 | 0.0779 | 35.3 |
| | | | 0.0096 | 180.8 | 0.0245 | 165.2 | 0.0735 | 169.3 | 0.0750 | 14.6 |
| | | | 0.0069 | 148.3 | 0.0218 | 154.2 | 0.0679 | 108.1 | 0.0708 | 3.0 |
| | | | 0.0038 | 55.4 | 0.0187 | 152.5 | 0.0618 | 81.8 | 0.0660 | 10.7 |
| | | | 0.0017 | 0.2 | 0.0166 | 155.5 | 0.0568 | 91.8 | 0.0627 | 14.5 |
| | | | 0.0009 | 0.0 | 0.0158 | 163.8 | 0.0541 | 94.1 | 0.0506 | 16.1 |
| | | | | | 0.0110 | 152.6 | 0.0508 | 101.1 | 0.0335 | 14.0 |
| | | | | | 0.0064 | 104.3 | 0.0324 | 101.4 | 0.0260 | 5.4 |
| | | | | | 0.0049 | 55.6 | 0.0154 | 98.9 | 0.0231 | 1.2 |
| | | | | | 0.0039 | 13.1 | 0.0076 | 49.0 | 0.0223 | 0.0 |
| | | | | | 0.0035 | 0.0 | 0.0039 | 0.2 | | |
| | | | | | | | 0.0018 | 0.0 | | |
| load plateau length (strain) | 0.0601 | | 0.0592 | | 0.0592 | | 0.0592 | | 0.0592 | |
| unload plateau length (strain) | 0.0596 | | 0.0662 | | 0.0654 | | 0.0717 | | 0.0485 | |
| permanent set (strain) | 0.0007 | | 0.0009 | | 0.0035 | | 0.0018 | | 0.0223 | |
| max vol. fraction martensite (%) | 1.2% | | 1.5% | | 5.9% | | 3.1% | | 37.6% | |

TABLE 5

Tensile Data for Various Wire Samples, see Examples 3-6, FIG. 19(c)

| 3.1 Engr. Strain | Engr. Stress (MPa) | 3.3 Engr. Strain | Engr. Stress (MPa) | 3.4 Engr. Strain | Engr. Stress (MPa) | 3.6 Engr. Strain | Engr. Stress (MPa) |
|---|---|---|---|---|---|---|---|
| 0 | 0 | 0 | 0 | 0 | 0 | 0 | 0 |
| 0.0003 | 16.0 | 0.0009 | 52.2 | 0.0007 | 37.7 | 0.0006 | 32.1 |
| 0.0048 | 237.0 | 0.0047 | 230.8 | 0.0044 | 239.5 | 0.0043 | 232.3 |
| 0.0105 | 450.1 | 0.0095 | 406.1 | 0.0092 | 420.0 | 0.0091 | 410.1 |
| 0.0138 | 550.1 | 0.0122 | 509.7 | 0.0119 | 525.8 | 0.0118 | 512.5 |
| 0.0173 | 544.5 | 0.0151 | 556.9 | 0.0149 | 570.7 | 0.0147 | 563.6 |

TABLE 5-continued

Tensile Data for Various Wire Samples, see Examples 3-6, FIG. 19(c)

| | \multicolumn{8}{c|}{Strain level} |
|---|---|---|---|---|---|---|---|---|
| | 3.1 Engr. Strain | Engr. Stress (MPa) | 3.3 Engr. Strain | Engr. Stress (MPa) | 3.4 Engr. Strain | Engr. Stress (MPa) | 3.6 Engr. Strain | Engr. Stress (MPa) |
| | 0.0358 | 527.9 | 0.0305 | 529.6 | 0.0303 | 539.6 | 0.0302 | 550.0 |
| | 0.0618 | 529.2 | 0.0522 | 523.1 | 0.0519 | 538.8 | 0.0518 | 513.0 |
| | 0.0733 | 549.4 | 0.0618 | 523.1 | 0.0615 | 543.5 | 0.0614 | 530.4 |
| | 0.0748 | 571.5 | 0.0630 | 510.2 | 0.0628 | 534.2 | 0.0627 | 539.5 |
| | 0.0785 | 631.8 | 0.0662 | 525.3 | 0.0659 | 548.4 | 0.0658 | 522.6 |
| | 0.0802 | 661.4 | 0.0687 | 529.5 | 0.0684 | 552.7 | 0.0683 | 507.3 |
| | 0.0807 | 664.3 | 0.0716 | 543.2 | 0.0713 | 567.4 | 0.0712 | 536.6 |
| | 0.0813 | 673.7 | 0.0755 | 590.1 | 0.0753 | 609.2 | 0.0752 | 591.3 |
| | 0.0820 | 686.2 | 0.0797 | 668.3 | 0.0794 | 670.0 | 0.0793 | 663.0 |
| | 0.0827 | 700.6 | 0.0841 | 767.6 | 0.0838 | 761.7 | 0.0837 | 758.2 |
| | 0.0832 | 709.6 | 0.0901 | 908.9 | 0.0899 | 899.3 | 0.0897 | 896.7 |
| | 0.0831 | 701.3 | 0.0969 | 1060.2 | 0.0976 | 1069.0 | 0.0975 | 1068.7 |
| | 0.0801 | 591.9 | 0.0973 | 1059.3 | 0.1001 | 1118.4 | 0.1000 | 1118.5 |
| | 0.0746 | 411.1 | 0.0979 | 1070.4 | 0.1043 | 1193.2 | 0.1045 | 1200.1 |
| | 0.0711 | 316.3 | 0.0983 | 1078.4 | 0.1046 | 1184.5 | 0.1075 | 1244.7 |
| | 0.0666 | 219.2 | 0.0988 | 1089.9 | 0.1051 | 1191.0 | 0.1112 | 1293.0 |
| | 0.0601 | 128.9 | 0.0994 | 1103.9 | 0.1059 | 1204.6 | 0.1166 | 1346.2 |
| | 0.0536 | 100.1 | 0.0998 | 1107.3 | 0.1066 | 1218.6 | 0.1186 | 1337.7 |
| | 0.0444 | 100.8 | 0.0992 | 1078.3 | 0.1076 | 1236.3 | 0.1197 | 1345.4 |
| | 0.0424 | 102.4 | 0.0975 | 1004.8 | 0.1077 | 1238.6 | 0.1199 | 1348.3 |
| | 0.0371 | 108.2 | 0.0931 | 821.3 | 0.1079 | 1235.3 | 0.1205 | 1355.8 |
| | 0.0306 | 107.0 | 0.0877 | 611.1 | 0.1080 | 1232.6 | 0.1212 | 1364.3 |
| | 0.0249 | 107.5 | 0.0829 | 445.7 | 0.1034 | 1040.9 | 0.1218 | 1370.6 |
| | 0.0209 | 111.3 | 0.0796 | 343.7 | 0.1001 | 903.4 | 0.1223 | 1374.5 |
| | 0.0159 | 109.8 | 0.0754 | 234.2 | 0.0959 | 738.9 | 0.1228 | 1378.9 |
| | 0.0101 | 100.7 | 0.0706 | 134.6 | 0.0911 | 563.4 | 0.1235 | 1383.3 |
| | 0.0059 | 78.9 | 0.0671 | 80.0 | 0.0876 | 445.1 | 0.1239 | 1386.1 |
| | 0.0031 | 43.4 | 0.0648 | 53.3 | 0.0853 | 374.5 | 0.1242 | 1387.8 |
| | 0.0021 | 17.8 | 0.0640 | 45.1 | 0.0845 | 350.1 | 0.1244 | 1388.4 |
| | 0.0006 | 2.2 | 0.0627 | 34.6 | 0.0832 | 314.7 | 0.1245 | 1389.3 |
| | 0.0003 | 0.0 | 0.0596 | 17.8 | 0.0801 | 233.3 | 0.1249 | 1391.5 |
| | | | 0.0567 | 12.8 | 0.0772 | 167.0 | 0.1253 | 1393.4 |
| | | | 0.0531 | 15.1 | 0.0736 | 100.4 | 0.1258 | 1395.6 |
| | | | 0.0510 | 15.6 | 0.0716 | 68.2 | 0.1261 | 1396.7 |
| | | | 0.0485 | 18.0 | 0.0691 | 36.9 | 0.1264 | 1398.2 |
| | | | 0.0458 | 22.0 | 0.0664 | 11.4 | 0.1267 | 1399.6 |
| | | | 0.0446 | 23.7 | 0.0651 | 2.6 | 0.1269 | 1400.2 |
| | | | 0.0433 | 24.1 | 0.0639 | 2.0 | 0.1271 | 1400.6 |
| | | | 0.0333 | 26.7 | 0.0539 | 2.0 | 0.1281 | 1399.7 |
| | | | 0.0306 | 26.5 | 0.0511 | 2.0 | 0.1256 | 1303.2 |
| | | | 0.0279 | 27.4 | 0.0484 | 2.0 | 0.1229 | 1197.3 |
| | | | 0.0217 | 23.0 | 0.0422 | 2.0 | 0.1166 | 960.1 |
| | | | 0.0167 | 22.8 | 0.0372 | 13.7 | 0.1116 | 779.5 |
| | | | 0.0140 | 18.3 | 0.0345 | 17.6 | 0.1089 | 686.3 |
| | | | 0.0102 | 9.8 | 0.0307 | 19.4 | 0.1052 | 563.2 |
| | | | 0.0063 | 0.4 | 0.0268 | 19.6 | 0.1012 | 441.7 |
| | | | 0.0019 | 0.5 | 0.0224 | 18.1 | 0.0968 | 318.9 |
| | | | 0.0013 | 0.0 | 0.0180 | 14.7 | 0.0924 | 208.9 |
| | | | | | 0.0141 | 8.3 | 0.0885 | 121.9 |
| | | | | | 0.0116 | 3.2 | 0.0860 | 73.7 |
| | | | | | 0.0109 | 0.0 | 0.0837 | 34.4 |
| | | | | | | | 0.0806 | 1.2 |
| | | | | | | | 0.0731 | 0.0 |
| load plateau length (strain) | 0.0664 | | 0.0646 | | 0.0633 | | 0.0675 | |
| unload plateau length (strain) | 0.0598 | | 0.0658 | | 0.0606 | | 0.0075 | |
| permanent set (strain) | 0.0003 | | 0.0013 | | 0.0109 | | 0.0731 | |
| max volume fraction martensite (%) | 0.4% | | 1.9% | | 17.3% | | 100.0% | |

TABLE 6

Tensile Data for Various Wire Samples, see Examples 3-6, FIG. 19(d)

| | | | | Strain level | | | | | |
|---|---|---|---|---|---|---|---|---|---|
| 4.1 Engr. Strain | Engr. Stress (MPa) | 4.3 Engr. Strain | Engr. Stress (MPa) | 4.4 Engr. Strain | Engr. Stress (MPa) | 4.6 Engr. Strain | Engr. Stress (MPa) | 4.7 Engr. Strain | Engr. Stress (MPa) |
| 0 | 0 | 0 | 0 | 0 | 0 | 0 | 0 | 0 | 0 |
| 0.0063 | 344.2 | 0.0037 | 195.8 | 0.0029 | 158.3 | 0.0024 | 127.7 | 0.0022 | 119.3 |
| 0.0108 | 520.9 | 0.0059 | 276.6 | 0.0050 | 239.7 | 0.0046 | 229.8 | 0.0043 | 211.8 |
| 0.0133 | 606.8 | 0.0076 | 335.0 | 0.0066 | 296.5 | 0.0063 | 294.0 | 0.0059 | 270.9 |
| 0.0158 | 644.6 | 0.0098 | 410.4 | 0.0087 | 372.3 | 0.0085 | 367.3 | 0.0080 | 341.4 |
| 0.0188 | 613.0 | 0.0119 | 498.4 | 0.0108 | 461.2 | 0.0106 | 448.9 | 0.0101 | 426.9 |
| 0.0218 | 635.5 | 0.0139 | 574.4 | 0.0127 | 534.1 | 0.0126 | 529.7 | 0.0120 | 503.2 |
| 0.0258 | 633.3 | 0.0161 | 625.0 | 0.0148 | 576.3 | 0.0148 | 596.8 | 0.0140 | 556.0 |
| 0.0308 | 623.0 | 0.0171 | 627.8 | 0.0158 | 585.0 | 0.0158 | 619.5 | 0.0151 | 569.8 |
| 0.0358 | 637.5 | 0.0206 | 631.5 | 0.0191 | 582.2 | 0.0193 | 630.6 | 0.0184 | 576.1 |
| 0.0403 | 638.8 | 0.0249 | 596.2 | 0.0233 | 556.1 | 0.0236 | 596.0 | 0.0226 | 539.8 |
| 0.0485 | 606.7 | 0.0293 | 591.9 | 0.0275 | 561.4 | 0.0280 | 634.6 | 0.0268 | 544.2 |
| 0.0668 | 614.5 | 0.0332 | 631.1 | 0.0312 | 581.7 | 0.0319 | 621.6 | 0.0305 | 578.1 |
| 0.0733 | 626.7 | 0.0403 | 622.8 | 0.0381 | 586.4 | 0.0390 | 628.7 | 0.0374 | 572.2 |
| 0.0745 | 662.3 | 0.0561 | 614.6 | 0.0533 | 559.5 | 0.0548 | 622.2 | 0.0526 | 564.7 |
| 0.0750 | 671.1 | 0.0618 | 621.3 | 0.0587 | 560.3 | 0.0605 | 615.9 | 0.0580 | 571.1 |
| 0.0756 | 687.8 | 0.0633 | 629.5 | 0.0602 | 580.9 | 0.0620 | 627.9 | 0.0595 | 572.1 |
| 0.0762 | 700.6 | 0.0661 | 599.2 | 0.0629 | 571.0 | 0.0648 | 608.4 | 0.0622 | 575.9 |
| 0.0767 | 711.5 | 0.0704 | 633.3 | 0.0670 | 575.6 | 0.0691 | 617.3 | 0.0663 | 573.1 |
| 0.0771 | 720.3 | 0.0741 | 633.6 | 0.0706 | 570.7 | 0.0728 | 623.8 | 0.0699 | 579.1 |
| 0.0776 | 729.8 | 0.0778 | 696.1 | 0.0741 | 619.8 | 0.0765 | 658.5 | 0.0734 | 595.5 |
| 0.0767 | 702.1 | 0.0808 | 771.2 | 0.0770 | 693.4 | 0.0795 | 735.8 | 0.0763 | 669.4 |
| 0.0740 | 605.1 | 0.0847 | 872.9 | 0.0808 | 788.7 | 0.0834 | 834.0 | 0.0801 | 760.8 |
| 0.0700 | 483.3 | 0.0891 | 988.3 | 0.0850 | 892.8 | 0.0878 | 949.9 | 0.0843 | 863.6 |
| 0.0662 | 393.5 | 0.0915 | 1054.0 | 0.0873 | 948.0 | 0.0902 | 1012.6 | 0.0865 | 927.3 |
| 0.0615 | 306.7 | 0.0921 | 1062.2 | 0.0906 | 1042.0 | 0.0936 | 1104.8 | 0.0899 | 1014.4 |
| 0.0572 | 254.7 | 0.0926 | 1072.8 | 0.0937 | 1120.0 | 0.0969 | 1190.8 | 0.0930 | 1093.3 |
| 0.0537 | 231.9 | 0.0931 | 1088.1 | 0.0967 | 1190.4 | 0.1010 | 1290.1 | 0.0970 | 1193.3 |
| 0.0502 | 231.4 | 0.0936 | 1100.9 | 0.0972 | 1193.8 | 0.1042 | 1337.2 | 0.1005 | 1275.6 |
| 0.0452 | 231.0 | 0.0940 | 1111.5 | 0.0976 | 1200.4 | 0.1046 | 1350.1 | 0.1034 | 1335.9 |
| 0.0405 | 235.6 | 0.0943 | 1121.8 | 0.0980 | 1210.2 | 0.1050 | 1355.4 | 0.1063 | 1387.3 |
| 0.0392 | 232.5 | 0.0948 | 1132.9 | 0.0985 | 1223.1 | 0.1055 | 1366.6 | 0.1105 | 1447.9 |
| 0.0372 | 229.3 | 0.0945 | 1124.8 | 0.0990 | 1238.3 | 0.1061 | 1380.9 | 0.1120 | 1440.1 |
| 0.0347 | 228.3 | 0.0934 | 1071.7 | 0.0991 | 1239.9 | 0.1062 | 1382.7 | 0.1122 | 1439.3 |
| 0.0317 | 227.7 | 0.0917 | 997.2 | 0.0993 | 1247.0 | 0.1065 | 1389.6 | 0.1124 | 1442.2 |
| 0.0297 | 228.9 | 0.0895 | 906.9 | 0.0996 | 1251.1 | 0.1068 | 1394.0 | 0.1127 | 1443.3 |
| 0.0255 | 230.4 | 0.0869 | 802.3 | 0.0998 | 1257.5 | 0.1071 | 1400.9 | 0.1130 | 1448.4 |
| 0.0235 | 231.8 | 0.0852 | 736.5 | 0.1000 | 1260.7 | 0.1073 | 1406.4 | 0.1132 | 1451.1 |
| 0.0205 | 223.7 | 0.0815 | 606.5 | 0.0995 | 1240.7 | 0.1077 | 1414.0 | 0.1137 | 1457.8 |
| 0.0182 | 225.8 | 0.0798 | 549.2 | 0.0979 | 1160.1 | 0.1079 | 1419.0 | 0.1139 | 1459.9 |
| 0.0157 | 227.6 | 0.0772 | 472.3 | 0.0954 | 1044.6 | 0.1082 | 1421.9 | 0.1143 | 1467.0 |
| 0.0130 | 225.4 | 0.0752 | 417.1 | 0.0935 | 961.4 | 0.1083 | 1423.1 | 0.1145 | 1469.6 |
| 0.0092 | 222.3 | 0.0731 | 363.5 | 0.0914 | 874.3 | 0.1069 | 1357.3 | 0.1148 | 1474.9 |
| 0.0072 | 222.4 | 0.0707 | 310.6 | 0.0891 | 779.1 | 0.1045 | 1251.5 | 0.1151 | 1478.9 |
| 0.0020 | 150.0 | 0.0674 | 250.9 | 0.0860 | 659.2 | 0.1012 | 1110.7 | 0.1155 | 1484.5 |
| 0.0010 | 75.0 | 0.0657 | 225.5 | 0.0843 | 597.0 | 0.0995 | 1036.4 | 0.1157 | 1486.3 |
| 0.0009 | 0.0 | 0.0629 | 193.1 | 0.0816 | 502.9 | 0.0967 | 919.4 | 0.1161 | 1490.9 |
| | | 0.0607 | 172.9 | 0.0795 | 436.5 | 0.0945 | 834.3 | 0.1164 | 1492.7 |
| | | 0.0579 | 160.3 | 0.0768 | 357.3 | 0.0917 | 725.4 | 0.1167 | 1496.4 |
| | | 0.0542 | 154.2 | 0.0733 | 264.8 | 0.0880 | 593.6 | 0.1172 | 1501.1 |
| | | 0.0494 | 161.9 | 0.0687 | 174.8 | 0.0832 | 439.3 | 0.1178 | 1506.8 |
| | | 0.0458 | 159.4 | 0.0652 | 121.4 | 0.0796 | 335.0 | 0.1182 | 1510.6 |
| | | 0.0427 | 155.4 | 0.0622 | 91.0 | 0.0765 | 261.1 | 0.1186 | 1511.7 |
| | | 0.0395 | 158.5 | 0.0591 | 73.2 | 0.0733 | 197.1 | 0.1187 | 1478.2 |
| | | 0.0375 | 157.3 | 0.0572 | 71.6 | 0.0713 | 163.8 | 0.1168 | 1425.1 |
| | | 0.0341 | 161.1 | 0.0539 | 69.4 | 0.0679 | 118.9 | 0.1134 | 1282.1 |
| | | 0.0302 | 166.9 | 0.0502 | 67.5 | 0.0640 | 85.0 | 0.1097 | 1123.1 |
| | | 0.0269 | 165.2 | 0.0470 | 71.3 | 0.0607 | 70.6 | 0.1066 | 994.2 |
| | | 0.0215 | 164.2 | 0.0418 | 77.9 | 0.0553 | 77.5 | 0.1014 | 788.7 |
| | | 0.0172 | 165.1 | 0.0377 | 75.9 | 0.0510 | 80.4 | 0.0972 | 634.1 |
| | | 0.0130 | 164.5 | 0.0337 | 75.8 | 0.0468 | 79.0 | 0.0932 | 495.0 |
| | | 0.0083 | 160.4 | 0.0291 | 80.2 | 0.0421 | 84.5 | 0.0887 | 350.3 |
| | | 0.0042 | 139.0 | 0.0252 | 77.5 | 0.0380 | 85.2 | 0.0847 | 241.7 |
| | | 0.0014 | 0.0 | 0.0229 | 76.3 | 0.0356 | 84.8 | 0.0824 | 183.3 |
| | | | | 0.0208 | 74.3 | 0.0334 | 83.8 | 0.0803 | 136.0 |
| | | | | 0.0181 | 76.3 | 0.0306 | 79.3 | 0.0776 | 83.7 |
| | | | | 0.0145 | 72.2 | 0.0269 | 80.6 | 0.0741 | 25.2 |
| | | | | 0.0133 | 69.9 | 0.0256 | 75.6 | 0.0728 | 8.4 |
| | | | | 0.0124 | 66.8 | 0.0247 | 72.9 | 0.0720 | 0.0 |
| | | | | 0.0058 | 71.1 | 0.0178 | 79.5 | | |
| | | | | 0.0029 | 0.0 | 0.0148 | 74.8 | | |
| | | | | | | 0.0059 | 69.5 | | |

TABLE 6-continued

Tensile Data for Various Wire Samples, see Examples 3-6, FIG. 19(d)

| | 4.1 Engr. Strain | Engr. Stress (MPa) | 4.3 Engr. Strain | Engr. Stress (MPa) | 4.4 Engr. Strain | Engr. Stress (MPa) | 4.6 Engr. Strain | Engr. Stress (MPa) | 4.7 Engr. Strain | Engr. Stress (MPa) |
|---|---|---|---|---|---|---|---|---|---|---|
| | | | | | | | 0.0035 | 29.8 | | |
| | | | | | | | 0.0026 | 0.0 | | |
| load plateau length (strain) | 0.0617 | | 0.0639 | | 0.0615 | | 0.0639 | | 0.0623 | |
| unload plateau length (strain) | 0.0563 | | 0.0643 | | 0.0623 | | 0.0652 | | 0.0021 | |
| permanent set (strain) | 0.0009 | | 0.0014 | | 0.0029 | | 0.0026 | | 0.0720 | |
| max volume fraction martensite (%) | 1.5% | | 2.1% | | 4.7% | | 4.1% | | 100.0% | |

TABLE 7

Tensile Data for Various Wire Samples, see Examples 3-6, FIG. 19(e)

| 5.1 Engr. Strain | Engr. Stress (MPa) | 5.3 Engr. Strain | Engr. Stress (MPa) | 5.4 Engr. Strain | Engr. Stress (MPa) | 5.6 Engr. Strain | Engr. Stress (MPa) | 5.7 Engr. Strain | Engr. Stress (MPa) |
|---|---|---|---|---|---|---|---|---|---|
| 0 | 0 | 0 | 0 | 0 | 0 | 0 | 0 | 0 | 0 |
| 0.0001 | 2.5 | 0.0002 | 11.8 | 0.0001 | 5.8 | 0.0002 | 11.1 | 0.0002 | 13.5 |
| 0.0036 | 197.0 | 0.0033 | 182.0 | 0.0032 | 174.2 | 0.0033 | 191.0 | 0.0034 | 193.3 |
| 0.0068 | 321.2 | 0.0060 | 293.0 | 0.0059 | 283.2 | 0.0060 | 305.5 | 0.0061 | 307.4 |
| 0.0092 | 420.8 | 0.0081 | 372.7 | 0.0080 | 362.4 | 0.0081 | 384.4 | 0.0082 | 387.0 |
| 0.0113 | 518.3 | 0.0100 | 450.1 | 0.0099 | 439.8 | 0.0100 | 460.9 | 0.0100 | 462.1 |
| 0.0137 | 602.3 | 0.0121 | 539.4 | 0.0120 | 529.9 | 0.0121 | 549.4 | 0.0121 | 550.0 |
| 0.0149 | 606.7 | 0.0131 | 577.0 | 0.0130 | 567.9 | 0.0131 | 588.0 | 0.0132 | 588.3 |
| 0.0187 | 609.1 | 0.0165 | 633.9 | 0.0164 | 628.5 | 0.0165 | 639.8 | 0.0165 | 634.2 |
| 0.0235 | 624.1 | 0.0206 | 623.3 | 0.0205 | 637.6 | 0.0206 | 646.8 | 0.0207 | 639.2 |
| 0.0283 | 620.0 | 0.0248 | 628.6 | 0.0247 | 620.0 | 0.0248 | 625.2 | 0.0248 | 631.3 |
| 0.0329 | 628.2 | 0.0288 | 620.0 | 0.0286 | 624.8 | 0.0287 | 606.2 | 0.0288 | 619.6 |
| 0.0458 | 614.3 | 0.0400 | 606.6 | 0.0399 | 622.1 | 0.0400 | 615.0 | 0.0400 | 615.0 |
| 0.0537 | 612.7 | 0.0469 | 615.0 | 0.0468 | 615.0 | 0.0469 | 620.9 | 0.0469 | 624.5 |
| 0.0647 | 636.0 | 0.0565 | 620.0 | 0.0564 | 620.8 | 0.0565 | 615.0 | 0.0565 | 610.8 |
| 0.0674 | 656.6 | 0.0588 | 626.8 | 0.0586 | 603.6 | 0.0587 | 626.8 | 0.0588 | 611.5 |
| 0.0684 | 646.8 | 0.0623 | 610.0 | 0.0622 | 620.0 | 0.0623 | 634.8 | 0.0623 | 636.4 |
| 0.0694 | 637.6 | 0.0688 | 646.3 | 0.0686 | 640.2 | 0.0687 | 662.6 | 0.0688 | 655.3 |
| 0.0703 | 640.1 | 0.0748 | 705.0 | 0.0747 | 701.0 | 0.0748 | 719.4 | 0.0748 | 715.1 |
| 0.0707 | 642.7 | 0.0777 | 749.6 | 0.0776 | 740.1 | 0.0777 | 755.5 | 0.0777 | 752.3 |
| 0.0712 | 646.6 | 0.0808 | 805.1 | 0.0807 | 795.0 | 0.0808 | 805.0 | 0.0809 | 805.5 |
| 0.0717 | 651.1 | 0.0840 | 868.1 | 0.0839 | 858.0 | 0.0840 | 866.6 | 0.0840 | 867.0 |
| 0.0723 | 658.7 | 0.0879 | 952.9 | 0.0878 | 941.8 | 0.0879 | 947.4 | 0.0880 | 947.7 |
| 0.0730 | 671.6 | 0.0925 | 1052.9 | 0.0924 | 1040.2 | 0.0925 | 1041.5 | 0.0925 | 1043.2 |
| 0.0737 | 682.3 | 0.0934 | 1060.4 | 0.0966 | 1128.3 | 0.0967 | 1125.7 | 0.0967 | 1127.9 |
| 0.0742 | 691.1 | 0.0939 | 1067.1 | 0.0999 | 1195.1 | 0.1004 | 1196.8 | 0.1005 | 1199.4 |
| 0.0748 | 701.8 | 0.0944 | 1077.3 | 0.1004 | 1187.8 | 0.1044 | 1265.3 | 0.1044 | 1268.1 |
| 0.0751 | 703.7 | 0.0949 | 1087.6 | 0.1009 | 1194.8 | 0.1081 | 1324.6 | 0.1082 | 1325.4 |
| 0.0753 | 704.0 | 0.0956 | 1100.8 | 0.1015 | 1205.8 | 0.1109 | 1346.4 | 0.1130 | 1386.1 |
| 0.0754 | 703.6 | 0.0958 | 1103.6 | 0.1021 | 1217.1 | 0.1115 | 1347.3 | 0.1175 | 1432.4 |
| 0.0735 | 637.3 | 0.0959 | 1101.9 | 0.1024 | 1223.2 | 0.1118 | 1350.7 | 0.1196 | 1448.7 |
| 0.0701 | 525.6 | 0.0960 | 1104.0 | 0.1028 | 1230.1 | 0.1122 | 1356.5 | 0.1215 | 1450.5 |
| 0.0679 | 461.5 | 0.0960 | 1102.9 | 0.1030 | 1234.8 | 0.1124 | 1358.8 | 0.1217 | 1440.6 |
| 0.0653 | 391.9 | 0.0961 | 1103.0 | 0.1031 | 1235.8 | 0.1127 | 1363.5 | 0.1221 | 1438.2 |
| 0.0627 | 331.9 | 0.0940 | 1019.0 | 0.1032 | 1233.0 | 0.1130 | 1367.1 | 0.1224 | 1439.4 |
| 0.0603 | 285.9 | 0.0919 | 933.0 | 0.1033 | 1234.5 | 0.1133 | 1372.6 | 0.1226 | 1441.9 |
| 0.0567 | 231.8 | 0.0888 | 809.1 | 0.1034 | 1234.1 | 0.1137 | 1379.2 | 0.1231 | 1446.7 |
| 0.0538 | 200.7 | 0.0863 | 714.9 | 0.1034 | 1234.0 | 0.1141 | 1383.4 | 0.1234 | 1450.9 |
| 0.0507 | 182.2 | 0.0836 | 618.5 | 0.1009 | 1131.5 | 0.1144 | 1388.9 | 0.1237 | 1455.6 |
| 0.0473 | 177.7 | 0.0807 | 522.3 | 0.0980 | 1009.8 | 0.1148 | 1393.5 | 0.1241 | 1458.7 |
| 0.0445 | 174.5 | 0.0782 | 446.6 | 0.0955 | 908.5 | 0.1151 | 1399.1 | 0.1245 | 1463.5 |
| 0.0409 | 177.4 | 0.0751 | 361.8 | 0.0924 | 786.7 | 0.1154 | 1401.2 | 0.1249 | 1467.6 |
| 0.0387 | 171.2 | 0.0732 | 316.3 | 0.0905 | 716.6 | 0.1155 | 1399.1 | 0.1251 | 1470.9 |
| 0.0351 | 164.4 | 0.0701 | 250.1 | 0.0874 | 605.7 | 0.1157 | 1400.1 | 0.1256 | 1474.3 |
| 0.0315 | 169.3 | 0.0669 | 195.9 | 0.0843 | 502.9 | 0.1158 | 1399.5 | 0.1260 | 1479.3 |
| 0.0277 | 164.7 | 0.0636 | 151.1 | 0.0809 | 403.7 | 0.1146 | 1351.2 | 0.1264 | 1483.6 |
| 0.0248 | 165.0 | 0.0611 | 125.9 | 0.0784 | 336.9 | 0.1121 | 1247.1 | 0.1267 | 1485.3 |
| 0.0215 | 162.7 | 0.0582 | 105.2 | 0.0755 | 267.7 | 0.1092 | 1127.3 | 0.1271 | 1489.0 |

TABLE 7-continued

Tensile Data for Various Wire Samples, see Examples 3-6, FIG. 19(e)

| | 5.1 Engr. Strain | Engr. Stress (MPa) | 5.3 Engr. Strain | Engr. Stress (MPa) | 5.4 Engr. Strain | Engr. Stress (MPa) | 5.6 Engr. Strain | Engr. Stress (MPa) | 5.7 Engr. Strain | Engr. Stress (MPa) |
|---|---|---|---|---|---|---|---|---|---|---|
| | 0.0181 | 153.3 | 0.0553 | 100.4 | 0.0726 | 208.4 | 0.1063 | 1009.9 | 0.1275 | 1491.0 |
| | 0.0152 | 139.7 | 0.0528 | 95.4 | 0.0701 | 165.6 | 0.1038 | 911.7 | 0.1279 | 1493.8 |
| | 0.0119 | 123.9 | 0.0499 | 106.2 | 0.0672 | 125.2 | 0.1009 | 800.8 | 0.1282 | 1494.9 |
| | 0.0083 | 98.7 | 0.0467 | 102.2 | 0.0641 | 92.7 | 0.0978 | 687.0 | 0.1287 | 1498.3 |
| | 0.0042 | 28.0 | 0.0432 | 93.8 | 0.0605 | 70.8 | 0.0942 | 565.7 | 0.1291 | 1501.2 |
| | 0.0021 | 0.0 | 0.0413 | 104.6 | 0.0586 | 68.3 | 0.0923 | 505.0 | 0.1294 | 1502.6 |
| | | | 0.0392 | 96.9 | 0.0566 | 64.6 | 0.0903 | 441.0 | 0.1296 | 1503.6 |
| | | | 0.0374 | 96.6 | 0.0547 | 67.4 | 0.0884 | 386.6 | 0.1298 | 1503.4 |
| | | | 0.0344 | 94.9 | 0.0518 | 62.4 | 0.0855 | 308.1 | 0.1301 | 1503.0 |
| | | | 0.0315 | 105.2 | 0.0489 | 69.0 | 0.0826 | 237.9 | 0.1304 | 1503.2 |
| | | | 0.0286 | 103.0 | 0.0459 | 72.7 | 0.0796 | 176.4 | 0.1307 | 1503.1 |
| | | | 0.0257 | 91.7 | 0.0430 | 67.4 | 0.0767 | 124.0 | 0.1289 | 1432.0 |
| | | | 0.0228 | 89.8 | 0.0401 | 59.2 | 0.0738 | 81.0 | 0.1259 | 1317.7 |
| | | | 0.0192 | 96.3 | 0.0366 | 59.5 | 0.0703 | 41.4 | 0.1224 | 1180.7 |
| | | | 0.0165 | 85.6 | 0.0339 | 63.0 | 0.0676 | 20.2 | 0.1197 | 1077.6 |
| | | | 0.0130 | 68.3 | 0.0303 | 67.8 | 0.0640 | 3.5 | 0.1161 | 946.0 |
| | | | 0.0094 | 48.8 | 0.0268 | 60.4 | 0.0605 | 5.2 | 0.1126 | 818.7 |
| | | | 0.0074 | 28.9 | 0.0247 | 59.9 | 0.0584 | 2.3 | 0.1105 | 746.4 |
| | | | 0.0059 | 9.8 | 0.0232 | 64.1 | 0.0569 | 0.6 | 0.1091 | 696.9 |
| | | | 0.0040 | 0.0 | 0.0214 | 62.4 | 0.0551 | 5.8 | 0.1072 | 634.9 |
| | | | | | 0.0189 | 59.6 | 0.0526 | 3.6 | 0.1047 | 555.1 |
| | | | | | 0.0153 | 46.2 | 0.0490 | 12.5 | 0.1024 | 485.2 |
| | | | | | 0.0116 | 27.2 | 0.0453 | 14.5 | 0.0982 | 366.4 |
| | | | | | 0.0061 | 0.0 | 0.0398 | 9.6 | 0.0934 | 244.1 |
| | | | | | | | 0.0342 | 14.2 | 0.0897 | 160.5 |
| | | | | | | | 0.0305 | 13.6 | 0.0861 | 92.3 |
| | | | | | | | 0.0244 | 11.7 | 0.0828 | 38.4 |
| | | | | | | | 0.0217 | 0.0 | 0.0805 | 7.3 |
| | | | | | | | | | 0.0784 | 0.0 |
| load plateau length (strain) | 0.0617 | | 0.0617 | | 0.0556 | | 0.0556 | | 0.0617 | |
| unload plateau length (strain) | 0.0546 | | 0.0596 | | 0.0610 | | 0.0485 | | 0.0021 | |
| permanent set (strain) | 0.0021 | | 0.0040 | | 0.0061 | | 0.0217 | | 0.0784 | |
| max volume fraction martensite (%) | 3.3% | | 6.5% | | 11.1% | | 39.0% | | 100.0% | |

IV. APPLICATIONS

Wires made in accordance with the present disclosure are susceptible of a variety of applications including, but not limited to the applications detailed below. Exemplary applications of wires in accordance with the present disclosure are set forth below, and shown generally in FIGS. 18(a)-19(b).

In some cases, a wire may have no remaining biased curvature, such as in a percutaneous transluminal coronary angioplasty (PTCA), steerable, and torque whip free guidewire application, or for a torque transmission wire for coronary plaque removal, for example.

Wire products used for medical devices as discussed herein will typically be subjected to mechanical conditioning in accordance with the present disclosure prior to integration into a medical device. However, it is contemplated that wire products may alternatively be installed into, or at least partially configured as, a medical device prior to subjecting the wire product to mechanical conditioning, followed by conducting the mechanical conditioning on the wire product after same is installed into, or at least partially configured as, a medical device, in order to impart benefits as disclosed herein.

A. DFT® and Other Composite Wire Materials

Wires disclosed herein may be used for composite wire products, such as shown in FIGS. 21(a)-(b). Composite wire 300 includes an outer shell 302 made of a first material, and a core 304 comprising at least one core segment of a second material, and optionally, additional core segments of third or more materials. Outer shell 302 may be made of a wire in accordance with the present disclosure, and core 304 may have a variety of desired properties, such as resistance, radiopacity, or any other property.

Thus, composite wire 300 may confer the benefits of load-conditioned and therefore fatigue damage resistant outer shell, such as fatigue strength, low or zero permanent set, etc, as described above by applying a suitable conditioning load to the wire product prior to installation within a medical device and/or configuration as a medical device, while also having other properties associated with the second material comprising core 304. An exemplary composite wire product is DFT®, available from Fort Wayne Metals Research Products Corp. of Fort Wayne, Ind.

B. Shape Memory Devices

1. Wire-Based Stents

Referring to FIG. 22(a), a tissue scaffold or vessel stent device 370 is shown which is made from one or more wires 372 made in accordance with the present process, which are braided, knitted, or otherwise formed together to produce the generally cylindrical cross-sectional shape of device 370.

Referring to and FIG. 22(b), a tissue scaffold or vessel stent device 370' is shown which is made from one or more wires 372' made in accordance with the present process, which are knitted together to form the generally cylindrical cross-sectional shape of device 370'.

Upon release from the delivery catheter, stents move to some degree, dependent on the relative vessel and device compliance, with the artery due to fluctuations in blood pressure, arterial vessel smooth muscle contraction and dilation, and due to general anatomical movement. Such mechanical displacement results in cyclic straining of wires 372, 372' comprising the structure of stent 370, 370'.

Non bioerodable tissue scaffolds or stents are generally implanted permanently, and therefore should be able to withstand millions of mechanical load cycles without losing structural integrity due to mechanical fatigue.

Stents 370, 370', which are constructed from wires 372, 372' made in accordance with the present process, possess a high degree of resistance to fatigue damage and thus offer optimized performance as compared to conventional stents made with wires having lower fatigue strength.

2. Blood Filters

Referring still to FIGS. 22(a)-(b), devices 370, 370' may also take the form of a blood filter which is made from one or more wires 372, 372' made in accordance with the present process, which are braided, knitted, or otherwise formed together to produce the generally cylindrical cross-sectional shape of devices 370, 370'. In this respect, many blood filter devices may be similar to braided, knitted, or laser-cut stents, and many interior vena cava (IVC) filters may be shaped as umbrella-shaped devices. In use, the superelastic characteristic of the device is utilized in that the device is inserted into a blood vessel via catheter in a collapsed condition and is deployed by expansion into the blood vessel, where the device captures and/or redirects larger blood clots from critical anatomical organs or regions. In use, particularly in permanent or non-retrievable devices, the device may be subjected to repeated, movements such that high fatigue strength is desired.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical device comprising a wire made of a nickel-titanium shape memory material, said wire having a fatigue endurance such that the wire survives $10^9$ cycles at a 2.2% peak-to-peak strain amplitude.

2. The medical device of claim 1, said nickel-titanium shape memory material having a plurality of defects, said wire substantially comprised of said nickel-titanium shape memory material in a primary phase and including secondary phase portions of said nickel-titanium shape memory material comprising a secondary phase at localized regions disposed proximate respective said defects, with at least some of said secondary phase portions separated by said primary phase, said primary phase is an austenite phase, and said secondary phase portions comprise a martensite phase.

3. The medical device of claim 2, wherein said secondary phase portions together comprise less than 15% of the nickel-titanium shape memory material, by volume.

4. The medical device of claim 1, wherein said wire is selected from the group consisting of wire having a circular cross-section, wire having a non-circular cross-section, cable, coil, and tubing.

5. The medical device of claim 1, wherein said wire has a circular cross-section.

6. The medical device of claim 1, wherein said wire has a non-circular cross-section.

7. The medical device of claim 1, wherein said wire comprises tubing.

8. The medical device of claim 1, wherein said wire has an isothermally non-recoverable strain of less than 1%.

9. The medical device of claim 1, wherein said wire has an isothermally non-recoverable strain of less than 0.35%.

10. The medical device of claim 1, wherein said wire has an isothermally non-recoverable strain of less than 0.25%.

11. The medical device of claim 1, wherein said wire has an isothermally non-recoverable strain of less than 0.20%.

12. A medical device comprising a wire made of a nickel-titanium shape memory material, said wire having a fatigue endurance such that the wire survives $10^6$ cycles at a 1.90% peak-to-peak strain amplitude, wherein said wire has a residual strain of less than 0.25% after being subjected to engineering strain of at least 9.5%.

13. The medical device of claim 12, said nickel-titanium shape memory material having a plurality of defects, said wire substantially comprised of said nickel-titanium shape memory material in a primary phase and including secondary phase portions of said nickel-titanium shape memory material comprising a secondary phase at localized regions disposed proximate respective said defects, with at least some of said secondary phase portions separated by said primary phase, said primary phase is an austenite phase, and said secondary phase portions comprise a martensite phase.

14. The medical device of claim 13, wherein said secondary phase portions together comprise less than 15% of the nickel-titanium shape memory material, by volume.

15. The medical device of claim 12, wherein said wire is selected from the group consisting of wire having a circular cross-section, wire having a non-circular cross-section, cable, coil, and tubing.

16. The medical device of claim 12, wherein said wire has a circular cross-section.

17. The medical device of claim 12, wherein said wire has a non-circular cross-section.

18. The medical device of claim 12, wherein said wire comprises tubing.

19. The medical device of claim 12, wherein said wire has an isothermally non-recoverable strain of less than 1%.

20. The medical device of claim 12, wherein said wire has an isothermally non-recoverable strain of less than 0.35%.

21. The medical device of claim 12, wherein said wire has an isothermally non-recoverable strain of less than 0.25%.

22. The medical device of claim 12, wherein said wire has an isothermally non-recoverable strain of less than 0.20%.

23. A medical device comprising a wire product made of a nickel-titanium shape memory material, said nickel-titanium shape memory material having a plurality of defects, said wire product substantially comprised of said nickel-titanium shape memory material in a primary phase and including secondary phase portions of said nickel-titanium shape memory material comprising a secondary phase at localized regions disposed proximate respective said defects, with at least some of said secondary phase portions separated by said primary phase, and said wire product has a fatigue endurance such that the wire product survives $10^9$ cycles at a 2.2% peak-to-peak strain amplitude.

24. The medical device of claim 23, wherein said wire product has a residual strain of less than 0.25% after being subjected to engineering strain of at least 9.5%.

25. The medical device of claim 23, wherein said wire product is selected from the group consisting of wire having a circular cross-section, wire having a non-circular cross-section, cable, coil, and tubing.

26. The medical device of claim 23, wherein said wire product has a circular cross-section.

27. The medical device of claim 23, wherein said wire product has a non-circular cross-section.

28. The medical device of claim 23, wherein said wire product comprises tubing.

29. The medical device of claim 23, wherein said wire product has an isothermally non-recoverable strain of less than 1%.

30. The medical device of claim 23, wherein said wire product has an isothermally non-recoverable strain of less than 0.35%.

31. The medical device of claim 23, wherein said wire product has an isothermally non-recoverable strain of less than 0.25%.

32. The medical device of claim 23, wherein said wire product has an isothermally non-recoverable strain of less than 0.20%.

33. A medical device comprising a wire product made of a nickel-titanium shape memory material, said nickel-titanium shape memory material having a plurality of defects, said wire product substantially comprised of said nickel-titanium shape memory material in a primary phase and including secondary phase portions of said nickel-titanium shape memory material comprising a secondary phase at localized regions disposed proximate respective said defects, with at least some of said secondary phase portions separated by said primary phase, wherein said wire product has a residual strain of less than 0.25% after being subjected to engineering strain of at least 9.5%.

34. The medical device of claim 33, wherein said wire product has a fatigue endurance such that the wire product survives $10^9$ cycles at a 2.2% peak-to-peak strain amplitude.

35. The medical device of claim 33, wherein said wire product is selected from the group consisting of wire having a circular cross-section, wire having a non-circular cross-section, cable, coil, and tubing.

36. The medical device of claim 33, wherein said wire product has a circular cross-section.

37. The medical device of claim 33, wherein said wire product has a non-circular cross-section.

38. The medical device of claim 33, wherein said wire product comprises tubing.

39. The medical device of claim 33, wherein said wire product has an isothermally non-recoverable strain of less than 1%.

40. The medical device of claim 33, wherein said wire product has an isothermally non-recoverable strain of less than 0.35%.

41. The medical device of claim 33, wherein said wire product has an isothermally non-recoverable strain of less than 0.25%.

42. The medical device of claim 33, wherein said wire product has an isothermally non-recoverable strain of less than 0.20%.

* * * * *